United States Patent
Igawa et al.

(10) Patent No.: US 11,400,157 B2
(45) Date of Patent: Aug. 2, 2022

(54) MULTIPLE ANTIGEN BINDING MOLECULAR FUSION, PHARMACEUTICAL COMPOSITION, METHOD FOR IDENTIFYING LINEAR EPITOPE, AND METHOD FOR PREPARING MULTIPLE ANTIGEN BINDING MOLECULAR FUSION

(71) Applicant: Chugai Seiyaku Kabushiki Kaisha, Tokyo (JP)

(72) Inventors: Tomoyuki Igawa, Shizuoka (JP); Naoka Hironiwa, Shizuoka (JP); Hiroki Kawauchi, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 123 days.

(21) Appl. No.: 15/573,154

(22) PCT Filed: May 13, 2016

(86) PCT No.: PCT/JP2016/064301
§ 371 (c)(1),
(2) Date: Nov. 10, 2017

(87) PCT Pub. No.: WO2016/182064
PCT Pub. Date: Nov. 17, 2016

(65) Prior Publication Data
US 2018/0125972 A1 May 10, 2018

(30) Foreign Application Priority Data
May 13, 2015 (JP) .............................. JP2015-098208

(51) Int. Cl.
| | | |
|---|---|---|
| *A61K 39/395* | (2006.01) |
| *A61K 47/42* | (2017.01) |
| *C07K 16/28* | (2006.01) |
| *C07K 16/32* | (2006.01) |
| *C07K 19/00* | (2006.01) |
| *C07K 14/00* | (2006.01) |
| *C07K 7/00* | (2006.01) |
| *A61K 47/50* | (2017.01) |
| *A61K 51/10* | (2006.01) |
| *A61K 47/68* | (2017.01) |
| *A61P 35/00* | (2006.01) |
| *C12N 15/09* | (2006.01) |
| *C12P 21/00* | (2006.01) |

(52) U.S. Cl.
CPC ...... *A61K 39/39558* (2013.01); *A61K 39/395* (2013.01); *A61K 47/42* (2013.01); *A61K 47/50* (2017.08); *A61K 47/6851* (2017.08); *A61K 51/1042* (2013.01); *A61P 35/00* (2018.01); *C07K 7/00* (2013.01); *C07K 14/00* (2013.01); *C07K 16/28* (2013.01); *C07K 16/32* (2013.01); *C07K 19/00* (2013.01); *C12N 15/09* (2013.01); *C12P 21/00* (2013.01)

(58) Field of Classification Search
None
See application file for complete search history.

(56) References Cited

FOREIGN PATENT DOCUMENTS

| | | |
|---|---|---|
| EP | 3070168 A1 | 9/2016 |
| JP | 2013528569 A | 7/2013 |
| JP | 2014519322 A | 8/2014 |
| JP | 2015509951 A | 4/2015 |
| JP | 2015509952 A | 4/2015 |
| WO | WO-03105757 A2 | 12/2003 |
| WO | WO-2009025846 A2 | 2/2009 |
| WO | WO-2010081173 A2 | 7/2010 |
| WO | WO-2010096868 A2 | 8/2010 |
| WO | WO-2011121110 A1 | 10/2011 |
| WO | WO-2012033953 A1 | 3/2012 |
| WO | WO-2012073985 A1 | 6/2012 |
| WO | WO-2012158818 A2 | 11/2012 |
| WO | WO-2013128027 A1 | 9/2013 |
| WO | WO-2013128194 A1 | 9/2013 |
| WO | WO-2013192546 A1 | 12/2013 |
| WO | WO-2014144722 A2 | 9/2014 |
| WO | WO-2015013671 A1 | 1/2015 |
| WO | WO-2015046554 A1 | 4/2015 |
| WO | WO-2015116933 A2 | 8/2015 |
| WO | WO-2016014974 A2 | 1/2016 |
| WO | WO-2016046778 A2 | 3/2016 |
| WO | WO-2016118629 A1 | 7/2016 |
| WO | WO-2016149201 A2 | 9/2016 |
| WO | WO-2016179003 A1 | 11/2016 |

OTHER PUBLICATIONS

Xu et al. (Cellular Immunology 2000 200: 16-26) (Year: 2000).*
Alley, S. C., et al., "Antibody-drug conjugates: targeted drug delivery for cancer," Curr Opin Chem Biol., 14:529-537 (2010).
Baeuerle, P. A., et al., "BiTE: Teaching antibodies to engage T-cells for cancer therapy," Curr Opin Mol Ther., 11 (1):22-30 (2009).
Chatenoud, L., "CD3-Specific Antibody-Induced Active Tolerance: From Bench to Bedside," Nature Rev Immunol, 3:123-132 (2003).
De Bono, J. S., et al., "ING-1, a Monoclonal Antibody Targeting Ep-CAM in Patients with Advanced Adenocarcinomas," Clin Cancer Res., 10:7555-7565 (2004).
Desjarlais, J. R., et al., "Optimizing engagement of the immune system by anti-tumor antibodies: an engineer's perspective," Drug Discovery Today, 12(21/22):898-910 (2007).
Fernandes, R. A., et al., "T Cell Receptors are Structures Capable of Initiating Signaling in the Absence of large Conformational Rearrangements," J Biol Chem., 287(16):13324-13335 (2012).

(Continued)

*Primary Examiner* — Peter J Reddig
(74) *Attorney, Agent, or Firm* — Nixon & Vanderhye P.C.

(57) ABSTRACT

A multiple antigen-binding molecule fusion molecule containing a multiple antigen-binding molecule (α) having an immune cell antigen-binding region and a cancer antigen-binding region, a cancer tissue-specific protease-cleavable linker (β), and a masking molecule (γ) containing a polypeptide having the amino acid sequence QDGNE (SEQ ID NO: 15), in which the multiple antigen-binding molecule (α) and the masking molecule (γ) are linked via the cancer tissue-specific protease-cleavable linker (β).

12 Claims, 16 Drawing Sheets
Specification includes a Sequence Listing.

(56) References Cited

OTHER PUBLICATIONS

Guthridge, J. M., et al., "Epitope Mapping Using the X-Ray Crystallographic Structure of Complement Receptor Type 2 (CR2)/CD21: Identification of a Highly Inhibitory Monoclonal Antibody That Directly Recognizes the CR2-C3d Interface," J Immunol., 167:5758-5766 (2001).

Igawa, T., "Next Generation Antibody Therapeutics Using Bispecific Antibody Technology," Yakugaku Zasshi, 137(7):831-836 (2017).

International Search Report dated Aug. 16, 2016 in International Application No. PCT/JP2016/064301.

Juszczak, A., et al., "Ipilimumab: a novel immunomodulating therapy causing autoimmune hypophysitis: a case report and review," Eur J Endocrinology 167:1-5 (2015).

Kim, S. J., et al., "Antibody Engineering for the Development of Therapeutic Antibodies," Mol Cells, 20(1):17-29 (2005).

Kjer-Nielsen, L., et al., "Crystal structure of the human T cell receptor CD3εγ heterodimer complexed to the therapeutic mAb OKT3," PNAS 101(20):7675-7680 (2004).

Lewis, G. D., et al., "Differential responses of human tumor cell lines to anti-p185$^{HER2}$ monoclonal antibodies," Cancer Immunol Immunother., 37:255-263 (1993).

Lutterbuese, R., et al., "T cell-engaging BiTE antibodies specific for EGFR potently eliminate KRAS- and BRAF-mutated colorectal cancer cells," PNAS 107(28):12605-12610 (2010).

Nam, J. L., et al., "Current evidence for the management of rheumatoid arthritis with biological disease-modifying antirheumatic drugs: a systemic literature review informing the EULAR recommendations for the management of RA," Ann Rheum Dis., 69:976-986 (2010).

Pavlou, A. K., et al., "The therapeutic antibodies market to 2008," Eur J Pharmaceut Biopharmaceut., 59:389-396 (2005).

Ponomarenko, J., et al., "ElliPro: a new structure-based tool for the prediction of antibody epitopes," BMC Bioinformatics, 9:514 (2008).

Reichert, J. M., et al., "Monoclonal antibody successes in the clinic," Nat Biotechnol., 23(9):1073-1078 (2005).

Reichelmann, H., et al., "Phase I trial with the CD44v6-targeting immunoconjugate bivatuzumab mertansine in head and neck squamous cell carcinoma," Oral Oncol., 44:823-829 (2008).

Satoh, M., et al., "Non-fucosylated therapeutic antibodies as next-generation therapeutic antibodies," Expert Opin Biol Ther., 6(11):1161-1173 (2006).

Takeuchi, T. and Kameda, H., "The Japanese experience with biologic therapies for rheumatoid arthritis," Nat Rev Rheumatol., 6:644-652 (2010).

Trinh, V. A. and Hwu, W-J., "Ipilimumab in the treatment of melanoma," Expert Opin Biol Ther., 12(6):773-782 (2012).

Weiner, L. M., et al., "Monoclonal antibodies: versatile platforms for cancer immunotherapy," Nat Rev Immunol., 10:317-327 (2010).

Laporte, S. L., et al., "Abstract A203: CD3-EGFR bispecific Probody™ therapeutics induced tumor regressions and increased therapeutic window in preclinical studies," Mol Cancer Ther., 14(12 Supp 2):A203 (2015), Proceedings of the AACR-NCI-EORTC International Conference: Molecular Targets and Cancer Therapeutics: Nov. 5-9, 2015; Boston, MA, submitted in Opposition of EP3296395 on Mar. 25, 2022.

Laporte, S. L., et al., "CD3-EGFR bispecific Probody™ T Cell-engaging Bispecific Therapeutic Induces Tumor Regressions and Substantially Increases Safety Window in Preclinical Studies," Poster Presented at the AACR-NCI-EORTC International Conference: Molecular Targets and Cancer Therapeutics: Nov. 5-9, 2015; Boston, MA, submitted in Opposition of EP3296395 on Mar. 25, 2022.

Maynard, J. and Georgiou, G., "Antibody Engineering," Annu Rev Biomed Eng., 2:339-376 (2000), submitted in Opposition of EP3296395 on Mar. 25, 2022.

Pauthner, M., et al., Meeting Report: Antibody engineering and therapeutics, the annual meeting of the antibody society Dec. 7-10, 2015, San Diego, CA, USA, MABS, 8(3):617-652 (2016), submitted in Opposition of EP3296395 on Mar. 25, 2022.

Polu, K. R. and Lowman, H. B., "Probody therapeutics for targeting antibodies to diseased tissue," Expert Opin Biol Ther., 14(8):1049-1053 (2014), submitted in Opposition of EP3296395 on Mar. 25, 2022.

Priority document for WO2016046778, Provisional U.S. Appl. No. 62/055,330, filed Sep. 25, 2014, received by International Bureau on Nov. 10, 2015, submitted in Opposition of EP3296395 on Mar. 25, 2022.

Priority document for WO2016179003, Provisional U.S. Appl. No. 62/155,723, filed May 1, 2015, received by International Bureau on May 21, 2016, submitted in Opposition of EP3296395 on Mar. 25, 2022.

Sequence listing for WO2016179003, Provisional U.S. Appl. No. 62/155,723, filed May 1, 2015, submitted in Opposition of EP3296395 on Mar. 25, 2022.

Slides for presentation of Luc Desnoyers at Antibody Engineering and Therapeutics 2015, "Probody™ Therapeutics Enhance Therapeutic Window in Multiple Antibody Modalities," Presented at the Annual Meeting of the Antibody Society, Dec. 7-10, 2015, San Diego, CA, USA, submitted in Opposition of EP3296395 on Mar. 25, 2022.

Turk, B. E., et al., "Determination of protease cleavage site motifs using mixture-based oriented peptide libraries," Nat Biotechnol., 19:661-667 (2001), submitted in Opposition of EP3296395 on Mar. 25, 2022.

\* cited by examiner

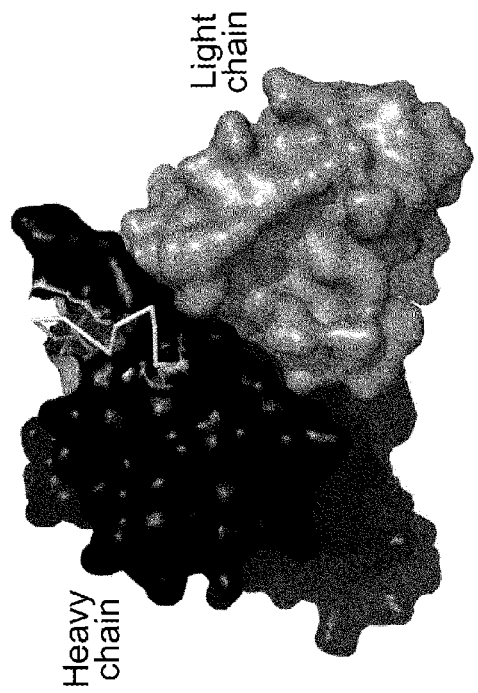
FIG. 6B  9-amino acid linker
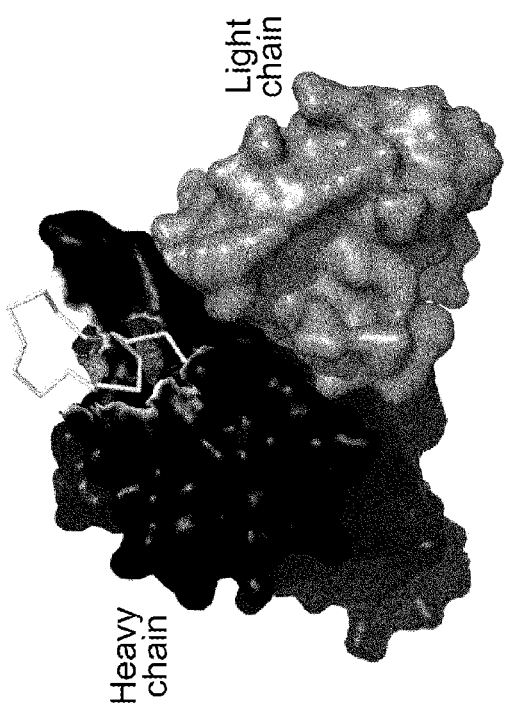
FIG. 6D  16-amino acid linker
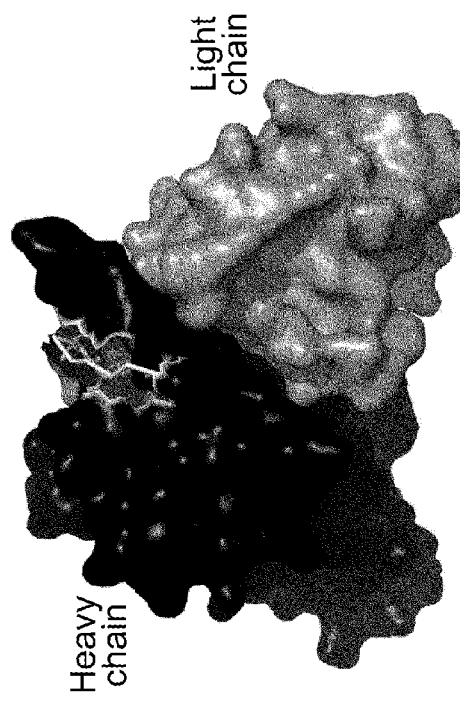
FIG. 6A  6-amino acid linker
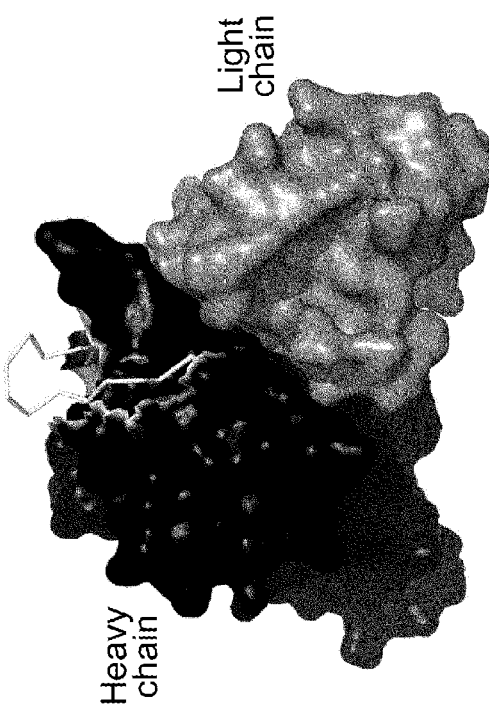
FIG. 6C  12-amino acid linker

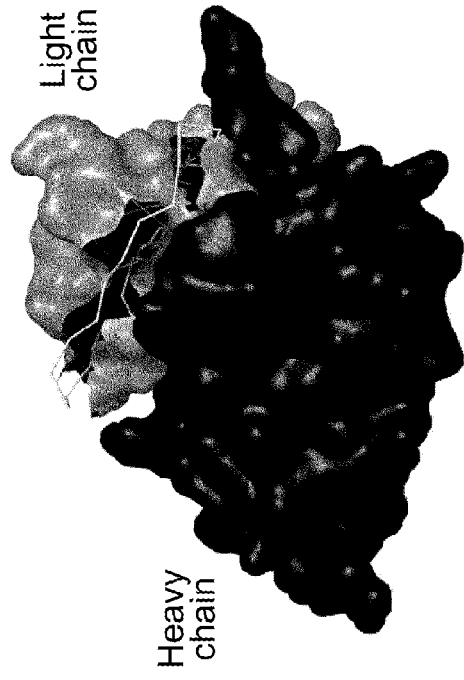
FIG. 7B   12-amino acid linker
FIG. 7D   16-amino acid linker
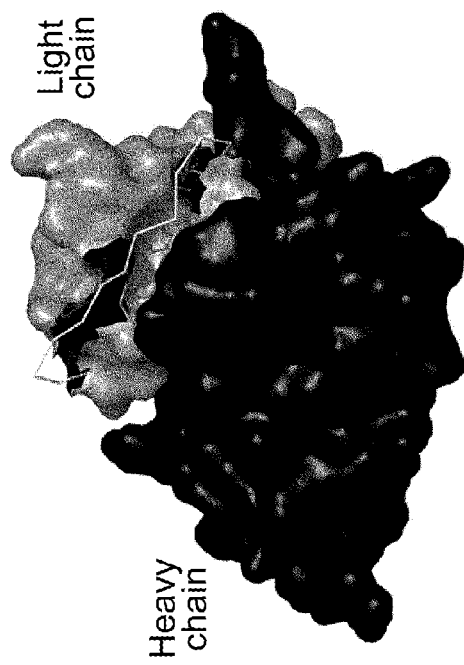
FIG. 7A   11-amino acid linker
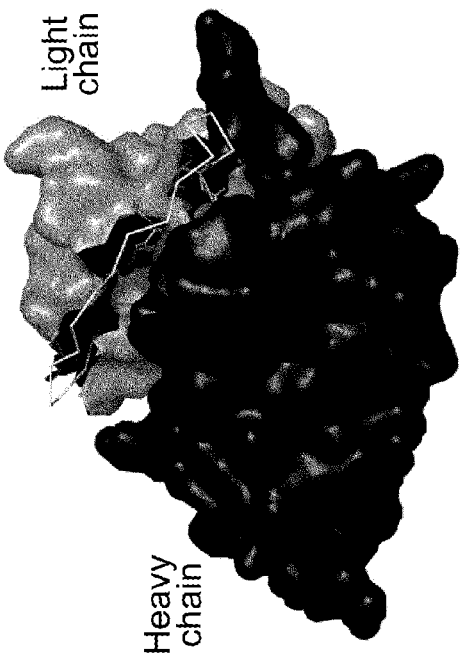
FIG. 7C   14-amino acid linker (i)

| Antibody name | Characteristics of the modifications at the heavy chain N-terminus (SEQ ID NO) | | Protease treatment | Antibody concentration at the time of preparation (μg/mL) | | | | | |
|---|---|---|---|---|---|---|---|---|---|
| | Masking molecule | Protease cleavable linker | | 4 | 1 | 0.25 | 0.0625 | 0.015625 | 0 |
| hCE115HA/GLS One arm | No | No | No | 160.2 | 40.4 | 11.4 | 4.2 | 1.9 | 0.9 |
| | | | Yes | 169.8 | 37.2 | 11.1 | 4.0 | 1.8 | 0.9 |
| hCE115HAGS/GLS One arm | 15 | 52 (noncleavable) | No | 1.5 | 1.0 | 1.0 | 0.9 | 0.9 | 0.9 |
| | | | Yes | 1.4 | 1.1 | 1.0 | 0.9 | 1.0 | 0.9 |
| hCE115HAuPA04/GLS One arm | 49 | 53 | No | 1.2 | 1.0 | 0.9 | 0.9 | 0.9 | 0.8 |
| | | | Yes | 136.2 | 31.7 | 8.6 | 3.3 | 1.6 | 0.9 |
| hCE115HAuPA20/GLS One arm | 50 | 54 | No | 1.2 | 1.0 | 0.9 | 0.9 | 0.9 | 0.8 |
| | | | Yes | 3.8 | 1.3 | 1.1 | 0.9 | 0.9 | 0.8 |
| hCE115HAuPA20L/GLS One arm | 50 | 59 | No | 1.1 | 1.0 | 0.9 | 1.0 | 0.9 | 0.9 |
| | | | Yes | 21.4 | 3.3 | 1.5 | 1.0 | 1.0 | 0.8 |
| hCE115HAuPA27/GLS One arm | 51 | 47 | No | 1.1 | 1.0 | 1.0 | 0.9 | 1.0 | 0.9 |
| | | | Yes | 1.6 | 1.9 | 0.4 | 0.3 | 0.6 | 0.8 |
| hCE115HAMMP/GLS One arm | 15 | 55 | No | 1.1 | 1.1 | 0.9 | 1.0 | 1.0 | 0.9 |
| | | | Yes | 1.0 | 1.0 | 1.0 | 1.0 | 1.0 | 1.0 |

(ii)

| Antibody name | Characteristics of the modifications at the light chain N-terminus (SEQ ID NO) | | Protease treatment | Antibody concentration at the time of preparation (μg/mL) | | | | | |
|---|---|---|---|---|---|---|---|---|---|
| | Masking molecule | Protease cleavable linker | | 4 | 1 | 0.25 | 0.0625 | 0.015625 | 0 |
| hCE115HA/GLS One arm | No | No | No | 612 | 257 | 105 | 43 | 17 | 1 |
| | | | Yes | 726 | 257 | 136 | 53 | 18 | 2 |
| hCE115HA/GLSGS One arm | 15 | 56 (noncleavable) | No | 18 | 6 | 3 | 2 | 2 | 1 |
| | | | Yes | 8 | 3 | 2 | 2 | 2 | 1 |
| hCE115HA/GLSuPA02 One arm | 15 | 54 | No | 76 | 24 | 8 | 4 | 2 | 1 |
| | | | Yes | 109 | 34 | 12 | 6 | 3 | 2 |
| hCE115HA/GLSuPA04 One arm | 49 | 53 | No | 3 | 2 | 2 | 2 | 2 | 2 |
| | | | Yes | 748 | 631 | 260 | 189 | 35 | 2 |
| hCE115HA/GLSuPA20 One arm | 50 | 54 | No | 2 | 1 | 1 | 1 | 1 | 1 |
| | | | Yes | 4 | 2 | 1 | 1 | 1 | 1 |
| hCE115HA/GLSuPA20L One arm | 50 | 59 | No | 1 | 1 | 1 | 1 | 1 | 1 |
| | | | Yes | 1 | 1 | 1 | 1 | 1 | 1 |
| hCE115HA/GLSuPA27 One arm | 51 | 47 | No | 2 | 1 | 1 | 1 | 1 | 1 |
| | | | Yes | 1 | 1 | 1 | 1 | 1 | 1 |
| hCE115HA/GLSMMP One arm | 15 | 55 | No | 1 | 1 | 1 | 1 | 1 | 1 |
| | | | Yes | 2 | 1 | 1 | 1 | 1 | 1 |

FIG. 8-1

(iii)

| Antibody name | Characteristics of the modifications at the light chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 4 | 1 | 0.25 | 0.0625 | 0.015625 | 0 |
| hCE115HA/GLS Two arm | No | No | No | 1169 | 618 | 189 | 45 | 11 | 1 |
| | | | Yes | 887 | 759 | 209 | 52 | 15 | 1 |
| hCE115HA/GLSGS Two arm | 15 | 56 (noncleavable) | No | 54 | 14 | 4 | 2 | 1 | 1 |
| | | | Yes | 18 | 4 | 2 | 1 | 1 | 1 |
| hCE115HA/GLSuPA20 Two arm | 50 | 54 | No | 1 | 1 | 1 | 1 | 1 | 1 |
| | | | Yes | 967 | 468 | 134 | 35 | 11 | 1 |
| hCE115HA/GLSMMP02 Two arm | 15 | 55 | No | 35 | 8 | 3 | 2 | 1 | 1 |
| | | | Yes | 28 | 8 | 1 | 1 | 1 | 1 |

(iv)

| Antibody name | Characteristics of the modifications at the heavy chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 1 | 0.25 | 0.0625 | 0.015625 | 0 | |
| AN/GLS One arm | No | No | No | 274 | 58 | 13 | 4 | 1 | |
| | | | Yes | 224 | 53 | 10 | 3 | 1 | |
| ANGS/GLS One arm | 15 | 52 (noncleavable) | No | 7 | 2 | 1 | 1 | 1 | |
| | | | Yes | 8 | 3 | 1 | 1 | 1 | |
| ANuPA02/GLS One arm | 15 | 57 | No | 4 | 2 | 1 | 1 | 1 | |
| | | | Yes | 219 | 58 | 14 | 4 | 1 | |
| ANuPA04/GLS One arm | 49 | 53 | No | 2 | 1 | 1 | 1 | 1 | |
| | | | Yes | 127 | 31 | 8 | 3 | 1 | |
| ANuPA20/GLS One arm | 50 | 54 | No | 1 | 1 | 1 | 1 | 1 | |
| | | | Yes | 53 | 10 | 3 | 1 | 1 | |
| ANuPA20L/GLS One arm | 50 | 59 | No | 1 | 1 | 1 | 1 | 1 | |
| | | | Yes | 41 | 8 | 2 | 1 | 1 | |
| ANuPA27/GLS One arm | 51 | 47 | No | 1 | 1 | 1 | 1 | 1 | |
| | | | Yes | 7 | 2 | 1 | 1 | 1 | |
| ANMMP/GLS One arm | 15 | 55 | No | 1 | 1 | 1 | 1 | 1 | |
| | | | Yes | 1 | 1 | 1 | 1 | 1 | |

| Antibody name | Characteristics of the modifications at the heavy chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 4 | 1 | 0.25 | 0.0625 | 0.015625 | 0 |
| hCE115HA/GLS One arm | No | No | No | 77 | 20 | 7 | 3 | 2 | 1 |
| | | | Yes | 65 | 19 | 6 | 3 | 2 | 1 |
| hCE115HAGS/GLS One arm | 15 | 52 (noncleavable) | No | 1 | 1 | 1 | 2 | 2 | 1 |
| | | | Yes | 1 | 1 | 1 | 1 | 2 | 1 |
| hCE115HAuPA04/GLS One arm | 49 | 53 | No | 1 | 1 | 1 | 1 | 1 | 1 |
| | | | Yes | 139 | 32 | 12 | 5 | 3 | 1 |
| hCE115HAuPA20/GLS One arm | 50 | 54 | No | 1 | 1 | 1 | 1 | 1 | 1 |
| | | | Yes | 12 | 4 | 2 | 1 | 1 | 1 |
| hCE115HAuPA20L/GLS One arm | 50 | 59 | No | 2 | 1 | 1 | 1 | 1 | 1 |
| | | | Yes | 7 | 2 | 1 | 1 | 1 | 1 |
| hCE115HAuPA27/GLS One arm | 51 | 47 | No | 2 | 1 | 1 | 1 | 1 | 1 |
| | | | Yes | 17 | 4 | 2 | 1 | 1 | 1 |

(ii)

| Antibody name | Characteristics of the modifications at the light chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 4 | 1 | 0.25 | 0.0625 | 0.015625 | 0 |
| hCE115HA/GLS One arm | No | No | No | 140 | 35 | 11 | 4 | 2 | 1 |
| | | | Yes | 114 | 32 | 7 | 3 | 2 | 1 |
| hCE115HA/GLSGS One arm | 15 | 56 (noncleavable) | No | 1 | 1 | 1 | 1 | 1 | 1 |
| | | | Yes | 1 | 1 | 1 | 1 | 1 | 1 |
| hCE115HA/GLSuPA02 One arm | 15 | 54 | No | 3 | 1 | 1 | 1 | 1 | 1 |
| | | | Yes | 11 | 3 | 1 | 1 | 1 | 1 |
| hCE115HA/GLSuPA04 One arm | 49 | 53 | No | 1 | 1 | 1 | 1 | 1 | 1 |
| | | | Yes | 257 | 61 | 18 | 6 | 2 | 1 |
| hCE115HA/GLSuPA20L One arm | 50 | 59 | No | 2 | 1 | 1 | 1 | 1 | 1 |
| | | | Yes | 1 | 1 | 1 | 1 | 1 | 1 |
| hCE115HA/GLSuPA27 One arm | 51 | 47 | No | 1 | 1 | 1 | 1 | 1 | 1 |
| | | | Yes | 8 | 2 | 1 | 1 | 1 | 1 |

| Antibody name | Characteristics of the modifications at the heavy chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 1 | 0.25 | 0.0625 | 0.015625 | 0 |
| hCE115HA/GLS One arm | No | No | No | 255 | 54 | 12 | 3 | 0 |
| | | | Yes | 243 | 32 | 12 | 4 | 1 |
| hCE115HAGS/GLS One arm | 15 | 52 (noncleavable) | No | 3 | 1 | 1 | 1 | 1 |
| | | | Yes | 2 | 1 | 1 | 1 | 1 |
| hCE115HAMMP02/GLS One arm | 15 | 55 | No | 3 | 2 | 1 | 1 | 1 |
| | | | Yes | 45 | 6 | 1 | 1 | 1 |

(ii)

| Antibody name | Characteristics of the modifications at the light chain N-terminus (SEQ ID NO) | | Protease treatment | Antibody concentration at the time of preparation (μg/mL) | | | | | |
|---|---|---|---|---|---|---|---|---|---|
| | Masking molecule | Protease-cleavable linker | | 1 | 0.25 | 0.0625 | 0.015625 | 0 |
| hCE115HA/GLS One arm | No | No | No | 126 | 23 | 7 | 2 | 0 |
| | | | Yes | 56 | 10 | 2 | 2 | 1 |
| hCE115HA/GLSGS One arm | 15 | 56 (noncleavable) | No | 1 | 1 | 1 | 1 | 1 |
| | | | Yes | 1 | 1 | 1 | 1 | 1 |
| hCE115HA/GLSuPA02 One arm | 15 | 54 | No | 1 | 1 | 1 | 1 | 1 |
| | | | Yes | 1 | 1 | 1 | 1 | 1 |
| hCE115HA/GLSMMP02 One arm | 15 | 55 | No | 1 | 1 | 1 | 1 | 1 |
| | | | Yes | 4 | 1 | 1 | 1 | 1 |

FIG. 10

MULTIPLE ANTIGEN BINDING MOLECULAR FUSION, PHARMACEUTICAL COMPOSITION, METHOD FOR IDENTIFYING LINEAR EPITOPE, AND METHOD FOR PREPARING MULTIPLE ANTIGEN BINDING MOLECULAR FUSION

CROSS REFERENCE TO RELATED APPLICATIONS

This application is a U.S. National Phase of International Patent Application No. PCT/JP2016/064301, filed May 13, 2016, which claims priority to Japanese Patent Application No. 2015-098208, filed May 13, 2015, each of which is incorporated herein by reference.

REFERENCE TO SEQUENCE LISTING SUBMITTED ELECTRONICALLY

The content of the electronically submitted sequence listing (Name: 6663_0050 Sequence_Listing.txt; Size: 280,522 bytes; and Date of Creation: Apr. 9, 2020) is incorporated herein by reference in its entirety.

TECHNICAL FIELD

The present invention relates to multiple antigen-binding molecule fusion molecules, pharmaceutical compositions, methods for identifying linear epitopes, and methods for producing multiple antigen-binding molecule fusion molecules.

BACKGROUND ART

Antibodies are drawing attention as pharmaceuticals as they are highly stable in plasma and have few side effects. In particular, a number of IgG-type antibody pharmaceuticals are available on the market, and many antibody pharmaceuticals are currently under development (Non-Patent Documents 1 and 2).

As cancer therapeutic agents using antibody pharmaceuticals, Rituxan (registered trademark) against a CD20 antigen, cetuximab against an EGFR antigen, herceptin (registered trademark) against a HER2 antigen, and such have been approved so far (Non-Patent Document 3). These antibody molecules bind to antigens expressed on cancer cells, and exhibit cytotoxic activity against cancer cells by ADCC and such. Such cytotoxic activity by ADCC and etc. are known to depend on the number of antigens expressed on cells targeted by the therapeutic antibodies (Non-Patent Document 4); therefore, high expression level of the target antigen is preferable from the stand point of the effects of the therapeutic antibodies. However, even if the antigen expression level is high, when antigens are expressed in normal tissues, cytotoxic activity mediated by ADCC etc. will be exerted against normal cells, and therefore side-effects will become a major problem. Therefore, antigens targeted by therapeutic antibodies used as therapeutic agents for cancer are preferably antigens specifically expressed in cancer cells. For example, antibody molecules against the EpCAM antigen which is known as a cancer antigen have been considered to be promising as therapeutic agents for cancer. However, the EpCAM antigen is known to be expressed in the pancreas as well, and in practice, administration of anti-EpCAM antibodies in clinical trials has been reported to cause pancreatitis as a side-effect due to cytotoxic activity towards the pancreas (Non-Patent Document 5).

Following the success of antibody pharmaceuticals that exert cytotoxic activity by ADCC activity, a second generation of improved antibody molecules that exert strong cytotoxic activity through enhancement of ADCC activity by removing fucose of N-type sugar chains in the native human IgG1 Fc region (Non-Patent Document 6), enhancement of ADCC activity by enhancing the binding toward Fcγ receptor IIIa by substitution of amino acids in the native human IgG1 Fc region (Non-Patent Document 7), and such have been reported. As antibody pharmaceuticals that exert cytotoxic activity against cancer cells through a mechanism other than the above-mentioned ADCC activity mediated by NK cells, improved antibody molecules that exert a stronger cytotoxic activity, such as an antibody-drug conjugate (ADC) in which an antibody is conjugated with a drug having potent cytotoxic activity (Non-Patent Document 8), and a low molecular weight antibody that exerts toxic activity against cancer cells by recruiting T cells to cancer cells (Non-Patent Document 9), have been reported as well.

Such antibody molecules exerting a stronger cytotoxic activity can exert cytotoxic activity against cancer cells that do not have much antigen expression, but on the other hand, they will exert similar cytotoxic activity against normal tissues with low antigen expression. In fact, in comparison to cetuximab which is a natural human IgG1 against EGFR, EGFR-BiTE, which is a bispecific antibody against CD3 and EGFR, can exert a potent cytotoxic activity against cancer cells by recruiting T cells to cancer cells and exert antitumor effects. On the other hand, since EGFR is expressed also in normal tissues, when EGFR-BiTE is administered to cynomolgus monkeys, serious side effects have appeared (Non-Patent Document 10). Furthermore, bivatzumab mertansine, an ADC formed by linking mertansine to an antibody against CD44v6 which is highly expressed in cancer cells, has been shown to cause severe skin toxicity and liver toxicity in clinical practice because CD44v6 is expressed also in normal tissues (Non-Patent Document 11).

When antibodies that can exert a potent cytotoxic activity against cancer cells having low antigen expression are used as such, the target antigen needs to be expressed in a highly cancer-specific manner. However, since HER2 and EGFR, which are target antigens of herceptin (registered trademark) and cetuximab, respectively, are also expressed in normal tissues, the number of cancer antigens expressed in a highly cancer-specific manner is thought to be limited. Therefore, while it is possible to strengthen the cytotoxic activity against cancer, the side effects occurring due to cytotoxic actions against normal tissues nay become problematic.

Furthermore, recently, ipilimumab which enhances tumor immunity by inhibiting CTLA4 which contributes to immunosuppression in cancer was shown to prolong overall survival of metastatic melanoma (Non-Patent Document 12). However, since ipilimumab inhibits CTLA4 systemically, while tumor immunity is enhanced, the emergence of autoimmune disease-like severe side effects due to systemic activation of the immune system is becoming a problem (Non-Patent Document 13).

On the other hand, as antibody pharmaceuticals against diseases besides cancer, antibody pharmaceuticals that exert therapeutic effects by inhibiting inflammatory cytokines in inflammatory/autoimmune diseases are known (Non-Patent Document 14). For example, Remicade (registered trademark) and Humira (registered trademark) which target TNF, and Actemra (registered trademark) which targets the IL-6 receptor exhibit high therapeutic effects against rheumatoid arthritis, but on the other hand, systemic neutralization of these cytokines has led to the observation of infection as side effects (Non-Patent Document 15).

Various techniques have been developed as techniques that can be applied to second-generation antibody pharmaceuticals. While techniques for improving effector functions, antigen-binding ability, pharmacokinetics, and stability, or techniques for reducing immunogenic risks have been reported (Non-Patent Document 16), there are hardly any reports on techniques that enable target tissue-specific action of antibody pharmaceuticals to overcome such side effects. For example, regarding lesions such as cancer tissues and inflammatory tissues, pH-dependent antibodies that make use of the acidic pH condition at these target tissues have been reported (Patent Documents 1 and 2). However, the decrease of pH (that is, increase in hydrogen ion concentration) in cancer tissues and inflammatory tissues as compared to normal tissues is slight, and since it is difficult to produce antibodies that act by detecting a slight increase in the concentration of hydrogen ions which have an extremely small molecular weight, and also because acidic pH conditions may be found in normal tissues such as osteoclastic bone resorption region or in tissues other than the lesion of interest, use of pH conditions as a lesion-specific environmental factor was considered to face many challenges.

On the other hand, methods for producing antibodies that exert antigen-binding activity only after they are cleaved by a protease expressed at lesion sites such as cancer tissues and inflammatory tissues have been reported (Patent Documents 3 and 4). In these methods, an artificial peptide having binding activity to an antigen-binding site of an antibody against a target antigen is fused to an antibody via a linker which can be cleaved by a protease, so that, when the linker is cleaved by a protease, the artificial peptide dissociates from the antibody and binding to the target antigen is enabled.

Furthermore, molecules in which a CD3ε partial protein is linked to an anti-CD3ε antibody (OKT3) via a linker to mask the CD3ε binding activity, which is recovered by cleavage of the linker by a protease, have been reported (Patent Document 5).

PRIOR ART DOCUMENTS

Patent Documents

[Patent Document 1] WO 2003/105757
[Patent Document 2] WO 2012/033953
[Patent Document 3] WO 2010/081173
[Patent Document 4] WO 2009/025846
[Patent Document 5] WO 2013/128194

Non-Patent Documents

[Non-Patent Document 1] Janice M Reichert, Clark J Rosensweig, et al., 'Monoclonal antibody successes in the clinic.' Nat Biotechnol., 2005, Vol. 23, pp. 1073-1078.
[Non-Patent Document 2] Pavlou A K, Belsey M J., 'The therapeutic antibodies market to 2008', Eur. J. Pharm. Biopharm., 2005, Vol. 59, No. 3, pp. 389-396.
[Non-Patent Document 3] Weiner L M, Surana R, et al., 'Monoclonal antibodies: versatile platforms for cancer immunotherapy', Nat. Rev. Immunol., 2010, Vol. 10, No. 5, pp. 317-327.
[Non-Patent Document 4] Lewis G D, Figari I, et al., 'Differential responses of human tumor cell lines to anti-p185HER2 monoclonal antibodies', Cancer Immunol. Immunotherapy, 1993, Vol. 37, pp. 255-263.
[Non-Patent Document 5] de Bono J S, Tolcher A W, et al., 'ING-1, a monoclonal antibody targeting Ep-CAM in patients with advanced adenocarcinomas', Clin. Cancer Res., 2004, Vol. 10, No. 22, pp. 7555-7565.
[Non-Patent Document 6] Satoh M, Iida S, et al., 'Non-fucosylated therapeutic antibodies as next-generation therapeutic antibodies', Expert Opin. Biol. Ther., 2006, Vol. 6, No. 11, pp. 1161-1173.
[Non-Patent Document 7] Desjarlais J R, Lazar G A, et al., 'Optimizing engagement of the immune system by antitumor antibodies: an engineer's perspective', Drug Discov. Today, 2007, Vol. 12, No. 21-22, pp. 898-910.
[Non-Patent Document 8] Alley S C, Okeley N M, et al., 'Antibody-drug conjugates: targeted drug delivery for cancer', Curr. Opin. Chem Biol., 2010, Vol. 14, No. 4, pp. 529-537.
[Non-Patent Document 9] Baeuerle P A, Kufer P, et al., 'BiTE: Teaching antibodies to engage T-cells for cancer therapy', Curr. Opin. Mol. Ther., 2009, Vol. 11, No. 1, pp. 22-30.
[Non-Patent Document 10] Lutterbuese R, Raum T, et al., 'T cell-engaging BiTE antibodies specific for EGFR potently eliminate KRAS- and BRAF-mutated colorectal cancer cells', Proc. Natl. Acad. Sci. U.S.A., 2010, Vol. 107, No. 28, pp. 12605-12610.
[Non-Patent Document 11] Riechelmann H, Sauter A, et al., 'Phase I trial with the CD44v6-targeting immunoconjugate bivatuzumab mertansine in head and neck squamous cell carcinoma', Oral Oncol., 2008, Vol. 44, No. 9, pp. 823-829.
[Non-Patent Document 12] Trinh V A, Hwu W J., 'Ipilimumab in the treatment of melanoma', Expert Opin. Biol. Ther., 2012, Apr., 14 (doi:10.1517/14712598.2012.675325).
[Non-Patent Document 13] Juszczak A, Gupta A, et al., 'IPILIMUMAB—A NOVEL IMMUNOMODULATING THERAPY CAUSING AUTOIMMUNE HYPOPHYSITS: A CASE REPORT AND REVIEW' Eur. J. Endocrinol., 2012, Apr., 10 (doi: 10.1530/EJE-12-0167).
[Non-Patent Document 14] Takeuchi T, Kameda H., 'The Japanese experience with biologic therapies for rheumatoid arthritis', Nat. Rev. Rheumatol., 2010, Vol. 6, No. 11, pp. 644-652.
[Non-Patent Document 15] Nam J L, Winthrop K L, et al., 'Current evidence for the management of rheumatoid arthritis with biological disease-modifying antirheumatic drugs: a systematic literature review informing the EULAR recommendations for the management of RA', Ann. Rheum. Dis., 2010 Vol. 69, No. 6, pp. 976-986.
[Non-Patent Document 16] Kim S J, Park Y, et al., 'Antibody engineering for the development of therapeutic antibodies', Mol. Cells., 2005, Vol. 20, No. 1, pp. 17-29.

SUMMARY OF THE INVENTION

Problems to be Solved by the Invention

An objective of the present invention is to generate and provide derivatives (herein, also referred to as "multiple antigen-binding molecule fusion molecules") for generically producing multiple antigen-binding molecules (also called "multispecific antigen-binding molecules") which recognize cancer antigens and CD3 and have reduced side-effects. Further, another objective is to provide pharmaceutical compositions containing multiple antigen-binding molecule fusion molecules; methods for identifying linear epitopes that are useful for multiple antigen-binding molecule fusion molecules; and methods for producing multiple antigen-binding molecule fusion molecules.

Means for Solving the Problems

As a result of dedicated research to accomplish the above-mentioned objectives, the present inventors generated multiple antigen-binding molecule fusion molecules that recognize a cancer antigen and CD3, whose CD3-binding activity is inhibited by a polypeptide having a specific amino acid sequence. This polypeptide is linked to a multiple antigen-binding molecule by a specific linker, and multiple antigen-binding molecule fusion molecules that exhibit activities specifically in cancer tissues upon cleavage of the linker by a cancer tissue-specific protease, were provided. Furthermore, the present inventors generated methods for identifying linear epitopes that are useful for multiple antigen-binding molecule fusion molecules and methods for producing the multiple antigen-binding molecule fusion molecules, and completed the present invention.

More specifically, the present invention provides the following:

[1] a multiple antigen-binding molecule fusion molecule comprising:
- a multiple antigen-binding molecule (α) which comprises an immune cell antigen-binding region which recognizes an antigen that comprises a polypeptide consisting of the amino acid sequence QDGNE (SEQ ID NO: 15) and a cancer antigen-binding region which recognizes a cancer antigen;
- a cancer tissue-specific protease-cleavable linker (β) which comprises a polypeptide consisting of a target sequence of a cancer tissue-specific protease; and
- a masking molecule (γ) which comprises a polypeptide consisting of the amino acid sequence QDGNE (SEQ ID NO: 15);
- wherein the multiple antigen-binding molecule (α) and the masking molecule (γ) are linked via the cancer tissue-specific protease-cleavable linker (β);

[2] the multiple antigen-binding molecule fusion molecule of [1], wherein the immune cell antigen-binding region recognizes at least one type of immune cell antigen other than the antigen that comprises a polypeptide consisting of the amino acid sequence QDGNE (SEQ ID NO: 15);

[3] the multiple antigen-binding molecule fusion molecule of [2], wherein the immune cell antigen-binding region does not recognize two or more immune cell antigens simultaneously,

[4] the multiple antigen-binding molecule fusion molecule of any one of [1] to [3], wherein the multiple antigen-binding molecule (α) is an antibody or an antibody fragment comprising at least two Fv regions, and the cancer antigen-binding region and the immune cell antigen-binding region are formed by different Fv regions;

[5] the multiple antigen-binding molecule fusion molecule of [4], wherein light chains of the antibody or the antibody fragment comprising at least two Fv regions both comprise a same amino acid sequence;

[6] the multiple antigen-binding molecule fusion molecule of [4] or [5], wherein the antibody or antibody fragment comprising at least two Fv regions further comprises an Fc region, and the Fc region is modified so as to lack a function of recognizing an Fcγ receptor;

[7] the multiple antigen-binding molecule fusion molecule of any one of [4] to [6], wherein the cancer tissue-specific protease-cleavable linker (β) is fused to a heavy chain N-terminus or a light chain N-terminus of the Fv region that forms the immune cell antigen-binding region;

[8] the multiple antigen-binding molecule fusion molecule of [7], wherein the cancer tissue-specific protease-cleavable linker (β) and the masking molecule (γ) form a linear fusion polypeptide, and wherein
- the number of amino acids in the fusion polypeptide is eleven or more to 65 or less when the cancer tissue-specific protease-cleavable linker (β) is fused to the heavy chain N-terminus of the Fv region that forms the immune cell antigen-binding region; and
- the number of amino acids in the fusion polypeptide is 16 or more to 65 or less when the cancer tissue-specific protease-cleavable linker (β) is fused to the light chain N terminus of the Fv region that forms the immune cell antigen-binding region;

[9] the multiple antigen-binding molecule fusion molecule of any one of [1] to [8], wherein the target sequence is the amino acid sequence PLGLAG (SEQ ID NO: 9);

[10] a pharmaceutical composition which comprises the multiple antigen-binding molecule fusion molecule of any one of [1] to [9] and a pharmaceutically acceptable carrier;

[11] the pharmaceutical composition of [10], which is for treating cancer;

[12] a method for treating cancer, wherein the method comprises administering the pharmaceutical composition of [10] or [11] to a patient;

[13] a method for identifying a linear epitope, wherein the method comprises identifying a linear epitope comprised in the immune cell antigen and recognized by the immune cell antigen-binding region based on three-dimensional protein structure analysis data obtained by using a protein complex of an immune cell antigen and an immune cell antigen-binding region which recognizes the immune cell antigen;

[14] a method for producing a multiple antigen-binding molecule fusion molecule, wherein the method comprises expressing a fusion protein in which a linear epitope is fused to a multiple antigen-binding molecule (α) which comprises a cancer antigen-binding region that recognizes a cancer antigen and an immune cell antigen-binding region that recognizes an immune cell antigen via a cancer tissue-specific protease-cleavable linker (β) which comprises a region that is cleavable by a protease specifically expressed in a cancer tissue expressing the cancer antigen;

[15] the multiple antigen-binding molecule fusion molecule of any one of [1] to [9] or the pharmaceutical composition of [10] or [11] for use in treating cancer;

[16] use of the multiple antigen-binding molecule fusion molecule of any one of [1] to [9] or the pharmaceutical composition of [10] or [11] for the manufacture of an anticancer agent; and

[17] a method for producing an anticancer agent, wherein the method comprises using the multiple antigen-binding molecule fusion molecule of any one of [1] to [9] or the pharmaceutical composition of [10] or [11].

Effects of the Invention

The present invention enables provision of derivatives (multiple antigen-binding molecule fusion molecules) for generically producing multiple antigen-binding molecules which recognize cancer antigens and CD3 and have reduced side-effects, and further provision of pharmaceutical compositions containing the multiple antigen-binding molecule fusion molecules; methods for identifying linear epitopes useful for the multiple antigen-binding molecule fusion molecules; and methods for producing multiple antigen-binding molecule fusion molecules.

BRIEF DESCRIPTION OF THE DRAWINGS

FIGS. 6A-6D show surface representations of models where the epitope core sequence is linked to the N terminus of the antibody heavy chain variable region via a Gly linker. In the figures, the antibody heavy chain is shown in black, the antibody light chain is shown in gray, and the linker is shown by a thick white line. FIG. 6A shows a model where the linkage is nude by a linker consisting of six amino acid residues. FIG. 6B shows a model where the linkage is nude by a linker consisting of nine amino acid residues. FIG. 6C shows a model where the linkage is made by a linker consisting of twelve amino acid residues. FIG. 6D shows a model where the linkage is made by a linker consisting of 16 amino acid residues.

FIG. 7-D show surface representations of models where the epitope core sequence is linked to the N terminus of the antibody light chain variable region via a Gly linker. In the figures, the antibody heavy chain is shown in black, the antibody light chain is shown in gray, and the linker is shown by a thick white line. FIG. 7A shows a model where the linkage is made by a linker consisting of eleven amino acid residues. FIG. 7B shows a model where the linkage is nude by a linker consisting of twelve amino acid residues. FIG. 7C shows a model where the linkage is made by a linker consisting of 14 amino acid residues. FIG. 7D shows a model where the linkage is made by a linker consisting of 16 amino acid residues.

FIG. 8-1 shows the results of evaluating CD3ε binding activities of anti-CD3 antibody derivatives and non-cleavable antibodies with masked binding to CD3ε after protease (uPA) treatment. The results are shown as a proportion when defining the luminescence value for a well without antigen addition as 1. (i) shows the CD3ε binding activities of antibodies with a peptide attached to their heavy chain N-terminus, and (ii) shows the CD3ε-binding activities of antibodies with a peptide attached to their light chain N-terminus.

FIG. 8-2 shows the results of evaluating CD3ε binding activities of anti-CD3 antibody derivatives and non-cleavable antibodies with masked binding to CD3s after protease (uPA) treatment. The results are shown as a proportion when defining the luminescence value for a well without antigen addition as 1. (iii) shows, similarly to (ii), the CD3ε binding activities of antibodies (TWO arm antibodies) with a peptide attached to their light chain N-terminus. (iv) shows the CD3ε binding activities of antibodies with a peptide attached to the heavy chain N-terminus of AN121.

FIG. 9 shows the results of evaluating CD3ε binding activities of anti-CD3 antibody derivatives and non-cleavable antibodies with masked binding to CD3ε after protease (human MT-SP1) treatment. The results are shown as a proportion when defining the luminescence value for a well without antigen addition as 1. (i) shows the CD3s-binding activities of antibodies with a peptide attached to their heavy chain N-terminus, and (ii) shows the CD3ε binding activities of antibodies with a peptide attached to their light chain N-terminus.

FIG. 10 shows the results of evaluating CD3s-binding activities of anti-CD3 antibody derivatives and non-cleavable antibodies with masked binding to CD3ε after protease (MMP-2) treatment. The results are shown as a proportion when defining the luminescence value for the antibody at 1 μg/mL as 1. (i) shows the CD3ε binding activities of antibodies with a peptide attached to their heavy chain N-terminus, and (ii) shows the CD3s-binding activities of antibodies with a peptide attached to their light chain N-terminus.

FIGS. 11-1 and 11-2 show the results of evaluating CD3ε activation by anti-CD3 antibody derivatives and non-cleavable antibodies with masked binding to CD3s after protease treatment. The derivatives have been prepared based on an antibody in which the heavy chain is hCE115HA and the light chain is GLS3000. FIG. 11-1 shows the results for an unmodified antibody to which no peptide has been attached and an antibody to which a masking molecule (γ) has been attached using a noncleavable GS linker. FIG. 11-2 shows the results for antibodies to which a masking molecule (γ) has been attached using a cancer tissue-specific protease-cleavable linker (β). The masking molecule (γ) of the respective antibodies is composed of a sequence of seven amino acids (since the linker portion includes a GG sequence, the sequence up to the ninth amino acid is the same sequence as the CD3ε N-terminus), 20 amino acids, or 27 amino acids from the N-terminus of CD3ε. In both FIGS. 11-1 and 11-2, the solid lines indicate protease-treated antibodies and the dashed lines indicate antibodies not subjected to protease treatment.

FIGS. 12-1 and 12-2 show the results of evaluating CD3ε activation by anti-CD3 antibody derivatives and non-cleavable antibodies with masked binding to CD3ε after protease treatment. The derivatives have been prepared based on an antibody in which the light chain is GLS3000 and AN121 having hCE115HA with enhanced CD3s binding force. FIG. 12-1 shows the results for an unmodified antibody to which no peptide has been attached and antibody to which a masking molecule (γ) has been attached using a noncleavable GS linker. FIG. 12-2 shows the results for antibodies to which a masking molecule (γ) has been attached using a cancer tissue-specific protease-cleavable linker (β). The masking molecule (γ) of the respective antibodies is composed of a sequence of seven amino acids (since the linker portion includes a GG sequence, the sequence up to the ninth amino acid is the same sequence as the CD3ε N-terminus), 20 amino acids, or 27 amino acids from the N-terminus of CD3ε. In both FIGS. 12-1 and 12-2, the solid lines indicate protease-treated antibodies and the dashed lines indicate antibodies not subjected to protease treatment.

FIGS. 13-1 and 13-2 show the results of evaluating CD3ε activation by anti-CD3 antibody derivatives and non-cleavable antibodies with masked binding to CD3ε after protease treatment. The derivatives have been prepared based on an antibody in which the heavy chain is rCE115H and the light chain is GLS3000. FIG. 13-1 shows the results for an unmodified antibody to which no peptide has been attached and an antibody to which a masking molecule (γ) has been attached using a noncleavable GS linker. FIG. 13-2 shows the results for antibodies to which a masking molecule (γ) has been attached using a cancer tissue-specific protease-cleavable linker (β). The masking molecule (γ) of the respective antibodies is composed of a sequence of seven amino acids (since the linker portion includes a GG sequence, the sequence up to the ninth amino acid is the same sequence as the CD3ε N-terminus), 20 amino acids, or 27 amino acids from the N-terminus of CD3ε. In both FIG. 13-1 and FIG. 13-2, the solid lines indicate protease-treated antibodies and the dashed lines indicate antibodies not subjected to protease treatment.

FIGS. 14-1 and 14-2 show the results of evaluating CD3ε activation by anti-CD3 antibody derivatives and non-cleavable antibodies with masked binding to CD3ε after protease treatment. The derivatives have been prepared based on an antibody in which the heavy chain is rCE115H and the light chain is rCE115L. FIG. 14-1 shows the results for an unmodified antibody to which no peptide has been attached and an antibody to which a masking molecule (γ) has been attached using a noncleavable GS linker. FIG. 14-2 shows the results for antibodies to which a masking molecule (γ) has been added using a cancer tissue-specific protease-cleavable linker (β). The masking molecule (γ) of the respective antibodies is composed of a sequence of seven amino acids (since the linker portion includes a GG sequence, the sequence up to the ninth amino acid is the same sequence as the CD3ε N-terminus), 20 amino acids, or 27 amino acids from the N-terminus of CD3ε. In both FIGS. 14-1 and 14-2, the solid lines indicate protease-treated antibodies and the dashed lines indicate antibodies not subjected to protease treatment.

FIGS. 15-1 and 15-2 show the results of evaluating CD3ε activation by anti-CD3 antibody derivatives and non-cleavable antibodies with masked binding to CD3ε after protease treatment. The derivatives have been prepared based on an antibody in which the heavy chain is hCE115HA and the light chain is GLS3000. FIG. 15-1 shows the results for an unmodified antibody to which no peptide has been attached and an antibody to which a masking molecule (γ) has been added using a noncleavable GS linker. FIG. 15-2 shows the results for antibodies to which a masking molecule (γ) has been attached using a cancer tissue-specific protease-cleavable linker (β). The masking molecule (γ) of the respective antibodies is composed of a sequence of seven amino acids (since the linker portion includes a GG sequence, the sequence up to the ninth amino acid is the same sequence as the CD3ε N-terminus), 20 amino acids, or 27 amino acids from the N-terminus of CD3ε. In both FIGS. 15-1 and 15-2, the solid lines indicate protease-treated antibodies and the dashed lines indicate antibodies not subjected to protease treatment.

MODE FOR CARRYING OUT THE INVENTION

Figure 1:
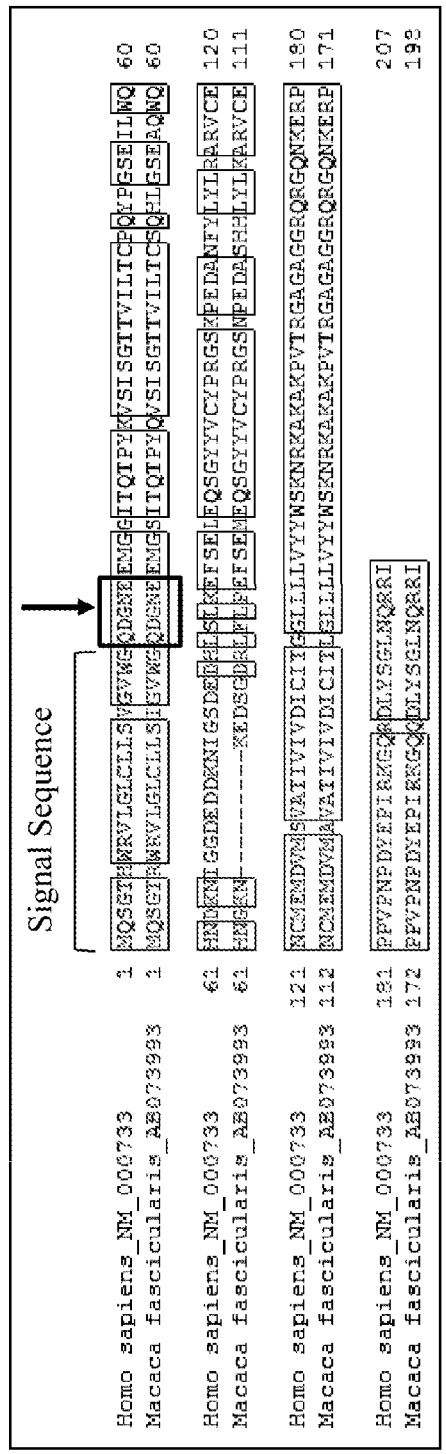
FIG. 1 shows an alignment of the amino acid sequences of human CD3ε (SEQ ID NO: 37) and cynomolgus CD3ε (SEQ ID NO: 38).

Herein, "recognize" means that an antigen-binding region, an antigen-binding molecule, an antibody, an antibody fragment, or such binds to an antigen. "Specifically recognize" means that an antigen-binding region, an antigen-binding molecule, an antibody, an antibody fragment, or such recognizes and binds to a specific three-dimensional structure in an antigen.

Furthermore, "antigen-binding region" indicates a region that is present in a molecule and can recognize an antigen. An antigen-binding region nay be formed by a polypeptide or a low-molecular-weight compound excluding polypeptides. An "immune cell antigen-binding region" can recognize an antigen specifically expressed by immune cells, and a "cancer antigen-binding region" can recognize a cancer antigen.

"Masking effect" indicates the effect of preventing an antigen-binding region from binding to its target antigen through binding of a masking molecule to the antigen-binding region.

"Linear peptide" indicates a polypeptide that does not form higher-order structures, or a polypeptide that, when forming higher-order structures, forms secondary structures such as α-helical structures, β-sheet structures, loops, and turns but does not form tertiary structures and quaternary structures. "Linear epitope" indicates a partial linear peptide in an antigen, which is recognized by an antigen-binding region.

Herein, "heavy chain" may be referred to as "H chain", and "light chain" may be referred to as "L chain".

The three-letter codes and corresponding one-letter codes of amino acids used herein are defined as follows: alanine: Ala and A, arginine: Arg and R, asparagine: Asn and N, aspartic acid: Asp and D, cysteine: Cys and C, glutamine: Gln and Q, glutamic acid: Glu and E, glycine: Gly and G, histidine: His and H, isoleucine: Ile and I, leucine: Leu and L, lysine: Lys and K, methionine: Met and M, phenylalanine: Phe and F, proline: Pro and P, serine: Ser and S, threonine: Thr and T, tryptophan: Trp and W, tyrosine: Tyr and Y, and valine: Val and V.

A. Multiple Antigen-Binding Molecule Fusion Molecules

Multiple antigen-binding molecule fusion molecules of the present invention comprise a multiple antigen-binding molecule (α), a cancer tissue-specific protease-cleavable linker (β), and a masking molecule (γ).

In such multiple antigen-binding molecule fusion molecules, a multiple antigen-binding molecule (α) and a masking molecule (γ) are linked via a cancer tissue-specific protease-cleavable linker (β).

The type of bond between a multiple antigen-binding molecule (α) and a cancer tissue-specific protease-cleavable linker (β), and the type of bond between a cancer tissue-specific protease-cleavable linker (β) and a masking molecule (γ) are not particularly limited. A preferred type of bond is a peptide bond.

Each component of multiple antigen-binding molecule fusion molecules of the present invention is described in detail below.

Multiple Antigen-Binding Molecule (α)

Multiple antigen-binding molecules (α) of the present invention contain immune cell antigen-binding regions and cancer antigen-binding regions. More specifically, a multiple antigen-binding molecule (α) is a molecule containing an immune cell antigen-binding region and a cancer antigen-binding region within the same molecule, and is not particularly limited as long as it has at least one immune cell antigen-binding region and one cancer antigen-binding region within the same molecule.

An embodiment of the multiple antigen-binding molecules (α) is, for example, a molecule containing a single immune cell antigen-binding region and a single cancer antigen-binding region within the same molecule. A specific example is a bispecific antibody.

Another embodiment of the multiple antigen-binding molecules (α) includes, for example, a molecule made by using techniques such as DART (WO2012/162067), Dual-Fab (PCT/JP2014/079785), 2+1 IgG Crossfab (WO2013/026833), and BiTE (Spiess C et al., Mol. Immunol. (2015)67 (2) 95-106).

An immune cell antigen-binding region and a cancer antigen-binding region nay be linked directly, or they nay be linked via a biocompatible linker. However, when an immune cell antigen-binding region is linked to a cancer antigen-binding region via a linker, to enable sufficient induction of cytotoxic activity, the linker is preferably not a cancer tissue-specific protease-cleavable linker (β) described below.

Regarding Immune Cell Antigen-Binding Regions

An immune cell antigen-binding region recognizes an antigen comprising a polypeptide consisting of the amino acid sequence QDGNE (SEQ ID NO: 15). The phrase "recognize an antigen comprising a polypeptide consisting of the amino acid sequence QDGNE (SEQ ID NO: 15)" means that the binding activity to an antigen is decreased or lost when the amino acid sequence QDGNE (SEQ ID NO: 15) is deleted.

A decrease in the binding activity can be confirmed by well-known methods such as FACS, ELISA format, screening by Amplified Luminescent Proximity Homogeneous Assay (ALPHA), and BIACORE method which uses the surface plasmon resonance (SPR) phenomenon. The decrease indicates, when the amino acid sequence QDGNE (SEQ ID NO: 15) is deleted from the antigen comprising a polypeptide consisting of the amino acid sequence QDGNE (SEQ ID NO: 15), the binding activity of 50% or less, preferably 45% or less, 40% or less, 35% or less, 30% or less, 20% or less, 15% or less, or particularly preferably 10% or less, 9% or less, 8% or less, 7% or less, 6% or less, 5% or less, 4% or less, 3% or less, 2% or less, or 1% or less as compared to the binding activity to the antigen before the deletion.

Here, the amino acid sequence QDGNE (SEQ ID NO: 15) is an amino acid sequence present in the extracellular region of human CD3ε, and is shared between human and cynomolgus monkey (seethe arrow in FIG. 1).

An antigen comprising a polypeptide having the amino acid sequence QDGNE (SEQ ID NO: 15) is preferably entirely a partial polypeptide of human CD3ε. Furthermore, human CD3ε partial polypeptides are preferably human CD3ε partial polypeptides comprising the amino acid sequence QDGNE (SEQ ID NO: 15) at its N terminus. The human CD3ε partial polypeptides having the amino acid sequence QDGNE (SEQ ID NO: 15) at its N terminus are preferably a region highly homologous to a corresponding partial polypeptide of cynomolgus CD3ε. The homology is preferably 90% or greater, more preferably 95% or greater, and most preferably 100%. If the homology is high, when a multiple antigen-binding molecule fusion molecule subjected to non-clinical toxicity assays using cynomolgus monkeys is used as it is in clinical trials, the assay results obtained from the non-clinical toxicity assays using cynomolgus monkeys will be likely to reflect the clinical trials.

An antigen comprising a polypeptide having the amino acid sequence QDGNE (SEQ ID NO: 15) may be chemically modified. The chemical modifications may be known modifications. Examples of the chemical modifications include acetylation, alkylation, and pyroglutamylation.

Among the modifications, pyroglutamylation of Q in the amino acid sequence QDGNE (SEQ ID NO: 15) is preferred.

An immune cell antigen-binding region which recognizes an antigen comprising a polypeptide having the amino acid sequence QDGNE (SEQ ID NO: 15) is obtained, for example, by a method that uses a known antibody preparation method.

An antibody obtained by such a preparation method may be used as it is for the immune cell antigen-binding region, or only an Fv region in the obtained antibody may be used. When such an Fv region in the form of a single chain (also referred to as "sc") can recognize the antigen, the single chain alone may be used. Alternatively, a Fab region containing the Fv region may be used.

Specific methods for preparing antibodies are well known to those skilled in the art. For example, monoclonal antibodies may be produced by a hybridoma method (Kohler and Milstein, Nature 256: 495 (1975)) or a recombination method (U.S. Pat. No. 4,816,567). Alternatively, monoclonal antibodies may be isolated from phage-displayed antibody libraries (Clackson et al., Nature 352: 624-628 (1991); and Marks et al., J. Mol. Biol. 222: 581-597 (1991)). Also, monoclonal antibodies may be isolated from single B cell clones (N. Biotechnol. 28 (5): 253-457 (2011)).

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR.

DNAs encoding antibody variable regions comprising three CDRs and four FRs linked and DNAs encoding human antibody constant regions can be inserted into expression vectors such that the variable region DNAs are fused in frame with the constant region DNAs to prepare vectors for humanized antibody expression. These vectors having the inserts are transferred to hosts to establish recombinant cells. Then, the recombinant cells are cultured for the expression of the DNAs encoding the humanized antibodies to produce the humanized antibodies into the cultures of the cultured cells (see European Patent Application Publication No. EP 239400 and WO1996/002576).

If necessary, FR amino acid residue(s) may be substituted such that the CDRs of the reshaped human antibody form an appropriate antigen-binding site. For example, the amino acid sequences of FR can be mutated by the application of the PCR method used in the mouse CDR grafting to the human FRs.

The desired human antibody can be obtained by DNA immunization using transgenic animals having all repertoires of human antibody genes (see WO1993/012227, WO1992/003918, WO1994/002602, WO1994/025585, WO1996/034096, and WO1996/033735) as immunized animals.

In addition, a technique of obtaining human antibodies by panning using human antibody libraries is also known. For example, a human antibody Fv region is expressed as a single-chain antibody (also referred to as "scFv") on the surface of phages by a phage display method. A phage expressing antigen-binding scFv can be selected. The gene of the selected phage can be analyzed to determine a DNA sequence encoding the Fv region of the antigen-binding human antibody. After determination of the DNA sequence of the antigen-binding scFv, the Fv region sequence can be fused in frame with the sequence of the desired human antibody C region and then inserted to appropriate expression vectors to prepare expression vectors. The expression vectors are introduced into preferred expression cells listed above for the expression of the genes encoding the human antibodies to obtain the human antibodies. These methods are already known in the art (see WO1992/001047, WO1992/020791, WO1993/006213, WO1993/011236, WO1993/019172, WO1995/001438, and WO1995/015388).

The binding activity of an immune cell antigen-binding region to an immune cell antigen can be enhanced by panning. The binding activity of an in me cell antigen-binding region to an immune cell antigen is calculated from data from binding assays that use the surface plasmon resonance (SPR) method (for example, using Biacore T200) or such. Binding activity is indicated by KD (M), and a smaller KD (M) indicates a higher binding activity. The KD (M) is preferably smaller than 10-, and more preferably smaller than $10^{-7}$.

For an immune cell antigen-binding region which recognizes an antigen comprising a polypeptide consisting of the amino acid sequence QDGNE (SEQ ID NO: 15), an antibody or antibody fragment newly obtained by an antibody preparation method as described above may be used, or a known antibody or antibody fragment that can recognize the antigen may be used. Examples of the known antibody or antibody fragment that can recognize an antigen comprising a polypeptide having the amino acid sequence QDGNE (SEQ ID NO: 15) include scFvs prepared in the Examples of WO2007/042261 and WO2002008/119567.

In addition to such scFvs, examples include CE115 disclosed in PCT/JP2014/079785. The method for preparing CE115 will be described later in Reference Example 1.

The immune cell antigen-binding regions of the present invention may only recognize antigens comprising a polypeptide having the amino acid sequence QDGNE (SEQ ID NO: 15), or may recognize antigens comprising a polypeptide consisting of the amino acid sequence QDGNE (SEQ ID NO: 15) as well as at least one type of immune cell antigen other than such antigens.

The immune cell antigen-binding regions of the present invention are preferably those that recognize antigens comprising a polypeptide having the amino acid sequence QDGNE (SEQ ID NO: 15) as well as at least one type of immune cell antigen other than such antigens.

Examples of immune cell antigens other than the antigen comprising a polypeptide having the amino acid sequence QDGNE (SEQ ID NO: 15) include T cell surface molecules, NK cell surface molecules, dendritic cell surface molecules, B cell surface molecules, NKT cell surface molecules, MDSC cell surface molecules, and macrophage surface molecules.

Specific examples of T cell surface molecules include CD3 and T cell receptors. However, in the case of CD3, it is a molecule which does not comprise a polypeptide having the amino acid sequence QDGNE (SEQ ID NO: 15). As long as the T cell surface molecules do not comprise a polypeptide having the amino acid sequence QDGNE (SEQ ID NO: 15), for example, in the case of human CD3, they may be those that bind to any epitope as long as the epitope is present in the γ chain, δ chain, or ε chain sequences that constitute human CD3.

Specific examples of immune cell antigens other than T cell surface molecules include Fcγ receptors, TLR, lectins, IgA, immune checkpoint molecules, TNF superfamily molecules, TNF receptor superfamily molecules, and NK receptor molecules.

In particular, in terms of further improvement of the cytotoxic activity against cancer cells by recruiting, in addition to T cells, various immune cells other than T cells such as NK cells to cancer cells, immune cell antigens to be recognized, other than antigens comprising a polypeptide having the amino acid sequence QDGNE (SEQ ID NO: 15), are preferably at least those selected from the group consisting of NK cell surface molecules, dendritic cell surface molecules, B cell surface molecules, NKT cell surface molecules, MDSC cell surface molecules, and macrophage surface molecules.

When an immune cell antigen-binding region is made to recognize an antigen comprising a polypeptide having the amino acid sequence QDGNE (SEQ ID NO: 15) and additionally at least one type of immune cell antigen other than said antigen, it is preferable that the immune cell antigen-binding region does not recognize two or more immune cell antigens simultaneously. By preparing an immune cell antigen-binding region so that it cannot recognize two or more immune cell antigens simultaneously, the multiple antigen-binding molecule fusion molecule becomes a molecule that cannot recognize multiple immune cells simultaneously. If a multiple antigen-binding molecule fusion molecule can recognize several immune cells simultaneously, these several immune cells may interfere with each other and consequently induce abnormal immune responses, and increase the occurrence of side effects. Therefore, by preparing the immune cell antigen-binding region so that it cannot recognize two or more immune cell antigens simultaneously, the possibility of side effects can be decreased.

Techniques of making an immune cell antigen-binding region recognize an antigen comprising a polypeptide having the amino acid sequence QDGNE (SEQ ID NO: 15) and additionally at least one type of immune cell antigen other than said antigen, and making the immune cell antigen-binding region not able to recognize two or more immune cell antigens simultaneously include, for example, the Dual-Fab technology. The Dual-Fab technology is a technology that enables a single Fab to recognize two or more antigens, and is disclosed in PCT/JP2014/079785. A specific example of a method for producing antigen-binding molecules by the Dual-Fab technology is a production method comprising the following steps (i) to (iv):

(i) preparing a library of antigen-binding molecules with at least one amino acid altered in their antibody variable regions each binding to a first antigen or a second antigen, wherein the altered variable regions differ in at least one amino acid from each other;

(ii) selecting, from the prepared library, an antigen-binding molecule containing a variable region that has binding activity against the first antigen and the second antigen, but does not bind to the first antigen and the second antigen at the same time;

(iii) culturing a host cell comprising a nucleic acid encoding the variable region of the antigen-binding molecule selected in the step (ii), to express an immune cell antigen-binding region containing the antibody variable region that can bind to the first antigen and the second antigen but does not bind to the first antigen and the second antigen at the same time; and (iv) recovering the antigen-binding molecule from the host cell culture.

In this production method, the step (ii) may be the following step (v):

(v) selecting, from the prepared library, an antigen-binding molecule containing a variable region that has binding activity against the first antigen and the second antigen, but does not bind to the first antigen and the second antigen each expressed on a different cell, at the same time.

Regarding Cancer Antigen-Binding Regions

Cancer antigen-binding regions recognize cancer antigens. A function of such regions is, for example, to highly concentrate multiple antigen-binding molecule fusion molecules at cancer tissues by their recognition of cancer antigens.

Cancer antigen-binding regions are not particularly limited so long as they can recognize cancer antigens. More specifically, a cancer antigen-binding region may be a polypeptide such as Fv of an antibody that recognizes a cancer antigen, or it may be a low-molecular-weight compound other than polypeptides, such as folic acid. In the case it is a low-molecular-weight compound, a step of linking the cancer antigen-binding region to an immune cell antigen-binding region becomes necessary for producing a multiple antigen-binding molecule ($\alpha$). Therefore, the cancer antigen-binding region is preferably a polypeptide, since in that case, a multiple antigen-binding molecule ($\alpha$) can be produced simply by allowing cells to express it and this will enable an increase in production efficiency.

A cancer antigen is a tumor cell-specific antigen, and includes an antigen expressed in association with the malignant alteration of cells, and also an abnormal sugar chain that appears on the cell surface or on a protein molecule during the malignant transformation of cells.

Specific examples of a cancer antigen include glypican-3 (GPC3), ALK receptor (pleiotrophin receptor), pleiotrophin, KS 1/4 pancreatic cancer antigen, ovary cancer antigen (CA125), prostatic acid phosphate, prostate-specific antigen (PSA), melanoma-associated antigen p97, melanoma antigen gp75, high-molecular-weight melanoma antigen (HMW-MAA), prostate-specific membrane antigen, carcinoembryonic antigen (CEA), polymorphic epithelial mucin antigen, human milk fat globule antigen, colorectal tumor-associated antigen (e.g., CEA, TAG-72, CO17-1A, GICA 19-9, CTA-1, and LEA), Burkitt's lymphoma antigen 38.13, CD19, human B lymphoma antigen CD20, CD33, melanoma-specific antigen (e.g., ganglioside GD2, ganglioside GD3, ganglioside GM2, and ganglioside GM3), tumor-specific transplantation antigen (TSTA), T antigen, virus-induced tumor antigen (e.g., envelope antigens of DNA tumor virus and RNA tumor virus), colon CEA, oncofetal antigen α-fetoprotein (e.g., oncofetal trophoblastic glycoprotein 5T4 and oncofetal bladder tumor antigen), differentiation antigen (e.g., human lung cancer antigens L6 and L20), fibrosarcoma antigen, human T cell leukemia-associated antigen Gp37, newborn glycoprotein, sphingolipid, breast cancer antigen (e.g., EGFR (epithelial growth factor receptor)), NY-BR-16, NY-BR-16 and HER2 antigen (p185HER2), polymorphic epithelial mucin (PEM), malignant human lymphocyte antigen APO-1, differentiation antigen such as I antigen found in fetal erythrocytes, primary endoderm I antigen found in adult erythrocytes, I (Ma) found in embryos before transplantation or gastric cancer, M18 found in mammary gland epithelium, M39, SSEA-1 found in bone marrow cells, VEP8, VEP9, Myl, VIM-D5, D156-22 found in colorectal cancer, TRA-1-85 (blood group H), SCP-1 found in testis and ovary cancers, C14 found in colon cancer, F3 found in lung cancer, AH6 found in gastric cancer, Y hapten, Ley found in embryonic cancer cells, TL5 (blood group A), EGFR found in A431 cells, E1 series (blood group B) found in pancreatic cancer, FC10.2 found in embryonic cancer cells, gastric cancer antigen, CO-514 (blood group Lea) found in adenocarcinoma, NS-10 found in adenocarcinoma, CO-43 (blood group Leb), G49 found in A431 cell EGFR, MH2 (blood group ALeb/Ley) found in colon cancer, 19.9 found in colon cancer, gastric cancer mucin, T5A7 found in bone marrow cells, R24 found in melanoma, 4.2, GD3, D1.1, OFA-1, GM2, OFA-2, GD2, and M1:22:25:8 found in embryonic cancer cells, SSEA-3 and SSEA-4 found in 4-cell to 8-cell embryos, cutaneous T cell lymphoma-associated antigen, MART-1 antigen, sialyl Tn (STn) antigen, colon cancer antigen NY-CO-45, lung cancer antigen NY-LU-12 variant A, adenocarcinoma antigen ART1, paraneoplastic associated brain-testis-cancer antigen (onconeuronal antigen MA2 and paraneoplastic neuronal antigen), neuro-oncological ventral antigen 2 (NOVA2), blood cell cancer antigen gene 520, tumor-associated antigen CO-029, tumor-associated antigen MAGE-C1 (cancer/testis antigen CT7), MAGE-B1 (MAGE-XP antigen), MAGE-B2 (DAM6), MAGE-2, MAGE-4a, MAGE-4b MAGE-X2, cancer-testis antigen (NY-EOS-1), YKL-40, and any fragment of these polypeptides, and modified structures thereof (aforementioned modified phosphate groups, sugar chains, etc.), EpCAM, EREG, CA19-9, CA15-3, sialyl SSEA-1 (SLX), HER2, PSMA, CEA, and CLEC12A. Among the above, GPC3, EGFR, and p185HER2 are preferred, and GPC3 is more preferred.

Furthermore, beside antigens directly expressed by cancer cells such as those presented as examples above, cancer antigens may be antigens that are not expressed by cancer cells but exist inside or near cancer tissues and promote proliferation and metastases of cancer cells.

Cancer antigen-binding regions are obtained, for example, by a method that uses a known antibody preparation method.

An antibody obtained by such a preparation method may be used as it is for the cancer antigen-binding region, or only an Fv region in the obtained antibody may be used. When such an Fv region in the form of a single chain can recognize the antigen, the single chain alone may be used. Alternatively, a Fab region containing the Fv region may be used.

A specific antibody preparation method may be carried out in a similar manner to the specific antibody preparation method for the above-described immune cell antigen-binding region.

Furthermore, similarly to the binding activity of an immune cell antigen-binding region to an immune cell antigen, the binding activity of a cancer antigen-binding region to a cancer antigen can be enhanced by panning. The binding activity of an immune cell antigen-binding region to an immune cell antigen is calculated from data from binding assays that use the surface plasmon resonance (SPR) method (for example, using Biacore T200). Binding activity is indicated by KD (M), and a smaller KD (M) indicates a higher binding activity. The KD (M) is preferably smaller than $10^{-6}$, more preferably smaller than $10^{-7}$, and even more preferably smaller than $10^{-8}$.

An Embodiment of Multiple Antigen-Binding Molecules ($\alpha$)

Examples of an embodiment of multiple antigen-binding molecules ($\alpha$) include antibodies and antibody fragments, and their fusion molecules and complexes, and such.

Herein, "antibody" is used in the broadest sense and also includes any antibody such as monoclonal antibodies (including full-length monoclonal antibodies), polyclonal antibodies, antibody variants, antibody fragments, multispecific antibodies (e.g., bispecific antibodies), chimeric antibodies, and humanized antibodies as long as the antibody exhibits the desired biological activity.

Moreover, the antibody is not limited by the type of its antigen, its origin, or such, and may be any antibody. Examples of the origin of the antibody can include, but are not particularly limited to, human antibodies, mouse antibodies, rat antibodies, and rabbit antibodies.

Among those described above, an example of a preferred antibody is a multispecific antibody. A multispecific antibody is an antibody that can recognize two or more antigens. When a multispecific antibody is used as the multiple antigen-binding molecule (α), the cancer antigen-binding region and the immune cell antigen-binding region are preferably formed by different Fv regions.

Multispecific antibodies can be produced by known production methods. Specifically, the following methods are given as examples.

An amino acid side chain present in the variable region of one antibody H chain is substituted by a larger side chain (knob), and its partner amino acid side chain present in the variable region of the other H chain is substituted by a smaller side chain (hole). The knob can be placed into the hole to efficiently associate polypeptides of the Fc regions differing in amino acid sequence (WO1996/027011; Ridgway J B et al., Protein Engineering (1996) 9, 617-621; and Merchant A M et al. Nature Biotechnology (1998) 16, 677-681).

The association of polypeptides having different sequences can be efficiently triggered by complementary association of CH3 using strand-exchange engineered domain CH3, in which a portion of CH3 of one H chain of an antibody is changed to a sequence derived from IgA corresponding to that portion, and a complementary portion of CH3 of the other H chain is introduced with a sequence derived from IgA corresponding to that portion (Protein Engineering Design & Selection, 23: 195-202, 2010).

Alternatively usable techniques are, for example, an antibody preparation technique using antibody CH1-CL association and H chain variable region (hereinafter abbreviated as "VH")-L chain variable region (hereinafter abbreviated as "VL") association as described in WO2011/028952, WO2014/018572, and Nat. Biotechnol. 2014 February; 32(2):191-8, a technique of preparing a bispecific antibody using separately prepared monoclonal antibodies (Fab Arm Exchange (also abbreviated as "FAE")) as described in WO2008/119353 and WO2011/131746, a technique of controlling the association between antibody heavy chain CH3 as described in WO2012/058768 and WO2013/063702, a technique of preparing a bispecific antibody constituted by two types of light chains and one type of heavy chain as described in WO2012/023053, or a technique of preparing a bispecific antibody using two bacterial cell lines each expressing an antibody half-molecule consisting of one H chain and one L chain as described in Christoph et al. (Nature Biotechnology Vol. 31, p. 753-758 (2013)).

Further, the CrossMab technique, a known hetero light chain association technique of associating a light chain forming a variable region binding to a first epitope and a light chain forming a variable region binding to a second epitope to a heavy chain forming a variable region binding to the first epitope and a heavy chain forming a variable region binding to the second epitope, respectively (Scaefer et al., Proc. Natl. Acad. Sci. U.S.A. (2011) 108, 11187-11192), can also be used for preparing a multispecific antibody.

Among these methods for producing multispecific antibodies, FAE is preferred. Examples of FAE include the methods described in WO2006/106905 and WO2015/046467, in which undesired association between H chains is suppressed by introducing electric charge repulsion at the interface of the second constant region of the antibody H chain (CH2) or the third constant region of the antibody H chain (CH3). In FAE which uses naturally-occurring IgG, re-association occurs randomly, and therefore bispecific antibodies can only be obtained at a theoretical efficiency of 50%; however, by the above-mentioned method, bispecific antibodies can be produced in high yield. This method is described in detail below.

In the technique of suppressing the unintended association between H chains by introducing electric charge repulsion to the CH2 or CH3 interface, examples of amino acid residues contacting with each other at the interface between the H chain constant regions can include a residue at EU numbering position 356, a residue at EU numbering position 439, a residue at EU numbering position 357, a residue at EU numbering position 370, a residue at EU numbering position 399, and a residue at EU numbering position 409 in one CH3 region, and their partner residues in another CH3 region.

More specifically, for example, in an antibody containing two types of H chain CH3 regions, one to three pairs of amino acid residues selected from the following amino acid residue pairs (1) to (3) in the first H chain CH3 region may be made to carry the same electric charge:
(1) the amino acid residues contained in the H chain CH3 region at position 356 and position 439 as indicated by EU numbering;
(2) the amino acid residues contained in the H chain CH3 region at position 357 and position 370 as indicated by EU numbering; and
(3) the amino acid residues contained in the H chain CH3 region at position 399 and position 409 as indicated by EU numbering.

Moreover, the antibody can be an antibody in which one to three pairs of amino acid residues in the second H chain CH3 region different from the above first H chain CH3 region are selected from the amino acid residue pairs shown in (1) to (3) above, correspond to the amino acid residue pairs shown in (1) to (3) above carrying the same electric charge in the first H chain CH3 region, and have opposite electric charge from the corresponding amino acid residues in the first H chain CH3 region.

The amino acid residues described in (1) to (3) above approach each other upon association. Those skilled in the art would be able to find positions corresponding to the amino acid residues described in (1) to (3) mentioned above for a desired H chain CH3 region or H chain constant region by homology modeling and such using commercially available software, and to suitably modify the amino acid residues at those positions.

In the antibody described above, each of the "amino acid residues carrying electric charge" is preferably selected from, for example, amino acid residues included in any of the following groups (a) and (b):
(a) glutamic acid (E) and aspartic acid (D); and
(b) lysine (K), arginine (R), and histidine (H).

In the antibody described above, the phrase "carrying the same electric charge" means that, for example, any two or more amino acid residues have amino acid residues that are contained in either one group of (a) and (b) mentioned above. "Having an opposite charge" means that, for example, when at least one amino acid residue among two or more amino acid residues is an amino acid residue contained in either one group of (a) and (b) mentioned above, the other amino acid residue(s) is an amino acid residue(s) contained in a different group.

In a preferred embodiment of the antibody as described above, the first H chain CH3 region and the second H chain CH3 region nmy be cross-linked by disulfide bonds.

An amino acid residue subjected to modification is not limited to an amino acid residue of the antibody variable region or antibody constant region mentioned above. Those skilled in the art would be able to find amino acid residues that form an interface in a polypeptide variant or heteromeric multimer by homology modeling and the like using commercially available software, and to modify amino acid residues at those sites so as to regulate association.

A plurality of, for example, two or more of these techniques for producing multispecific antibodies may be used in combination. Also, these techniques can be appropriately applied separately to the two H chains to be associated.

If a multispecific antibody cannot be formed efficiently, a multispecific antibody of interest can also be separated and purified from produced multispecific antibodies. For example, the previously reported method involves introducing amino acid substitutions to the variable regions of two types of H chains to impart thereto a difference in isoelectric points so that two types of homodimers and a heterodimerized antibody of interest can be purified by ion-exchanged chromatography (WO2007/114325). A method using protein A to purify a heterodimerized antibody consisting of a mouse IgG2a H chain that binds to protein A and a rat IgG2b H chain that does not bind to protein A has previously been reported as a method for purifying heterodimers (WO98/050431 and WO95/033844). Further, H chains in which amino acid residues at EU numbering positions 435 and 436 that constitute the protein A-binding site of IgG may be substituted with amino acids, such as Tyr and His, which offer the different binding force toward protein A, is used to change the interaction of each H chain with protein A, and only heterodimerized antibodies can be efficiently purified by using a protein A column.

Antibody fragments, when used as the multispecific antigen binding molecule (α) of the present embodiment, include those that contain both of a heavy chain and a light chain in a single polypeptide chain but lack a constant region. Specific examples of such antibody fragments include diabodies (db), single-chain antibodies, and sc(Fab')2.

A db is a dimer constituted by two polypeptide chains (e.g., Holliger P et al., Proc. Natl. Acad. Sci. USA 90: 6444-6448 (1993); EP404,097; and WO93/11161). The polypeptide chains are linked through a linker as short as, for example approximately 5 residues, such that a VL and a VH on the same polypeptide chain cannot be paired with each other.

Because of this short linker, VL and VH encoded on the same polypeptide chain cannot form a single-chain variable region fragment and form two antigen binding sites by dimerization.

Examples of the single-chain antibody include sc(Fv)2. An sc(Fv)2 is a single-chain antibody having one chain constituted by four variable regions, i.e., two VLs and two VHs, linked via linkers such as peptide linkers (J Immunol. Methods (1999) 231 (1-2), 177-189). These two VHs and VLs may be derived from different monoclonal antibodies. Preferred examples thereof include bispecific sc(Fv)2, which recognizes two types of epitopes present in the same antigen, as disclosed in Journal of Immunology (1994) 152 (11), 5368-5374. The sc(Fv)2 may be prepared by a method known to those skilled in the art. For example, the sc(Fv)2 can be prepared by connecting two scFvs via a linker such as a peptide linker.

Examples of the configuration of the antigen-binding domains constituting an sc(Fv)2 include an antibody in which two VHs and two VLs are aligned as VH, VL, VH, and VL (i.e., [VH]-linker-[VL]-linker-[VH]-linker-[VL]) in this order starting from the N-terminus of the single-chain polypeptide. The order of two VHs and two VLs is not particularly limited to the configuration described above and may be any order of arrangement. Examples include the following arrangements:

[VL]-linker-[VH]-linker-[VH]-linker-[VL],
[VH]-linker-[VL]-linker-[VL]-linker-[VH],
[VH]-linker-[VH]-linker-[VL]-linker-[VL],
[VL]-linker-[VL]-linker-[VH]-linker-[VH], and
[VL]-linker-[VH]-linker-[VL]-linker-[VH].

The molecular form of the sc(Fv)2 is also described in detail in WO2006/132352. On the basis of the description therein, those skilled in the art can appropriately prepare a desired sc(Fv)2 in order to prepare the multispecific antigen binding molecule (α) of the present embodiment.

An arbitrary peptide linker that can be introduced by genetic engineering or a synthetic compound linker (e.g., a linker disclosed in Protein Engineering, 9 (3), 299-305, 1996) can be used as the linker to link the variable regions. In the present embodiment, a peptide linker is preferred. The length of the peptide linker is not particularly limited and can be appropriately selected by those skilled in the art according to the purpose. The length is preferably 5 amino acids or more (the upper limit is not particularly limited and is usually 30 amino acids or less, preferably 20 amino acids or less), and particularly preferably 15 amino acids. When the sc(Fv)2 contains three peptide linkers, all of these peptide linkers used may have the same lengths or may have different lengths.

Examples of the peptide linker can include:

```
Ser,

Gly-Ser,

Gly-Gly-Ser,

Ser-Gly-Gly,

Gly-Gly-Gly-Ser (SEQ ID NO: 1),

Ser-Gly-Gly-Gly (SEQ ID NO: 2),

Gly-Gly-Gly-Gly-Ser (SEQ ID NO: 3),

Ser-Gly-Gly-Gly-Gly (SEQ ID NO: 4),

Gly-Gly-Gly-Gly-Gly-Ser (SEQ ID NO: 5),

Ser-Gly-Gly-Gly-Gly-Gly (SEQ ID NO: 6),

Gly-Gly-Gly-Gly-Gly-Gly-Ser (SEQ ID NO: 7),

Ser-Gly-Gly-Gly-Gly-Gly-Gly (SEQ ID NO: 8), (Gly-Gly-Gly-Gly-Ser (SEQ ID NO: 3))n,
and (Ser-Gly-Gly-Gly-Gly (SEQ ID NO: 4))n,
``` wherein n is an integer of 1 or larger.
However, the length and sequence of the peptide linker can be appropriately selected by those skilled in the art according to the purpose.

A synthetic compound linker (chemical cross-linking agent) is a cross-linking agent usually used in the cross-linking of peptides, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), or bis[2-(sulfosuccinimidoxycarbonyloxy) ethyl]sulfone (sulfo-BSOCOES).

These cross-linking agents are commercially available.

Three linkers are usually necessary for linking four antibody variable regions. All of these linkers used may be the same linkers or may be different linkers.

An F(ab')2 comprises two light chains and two heavy chains containing a constant region composed of a CH1 domain and a portion of the CH2 domain so as to form the interchain disulfide bonds between these two heavy chains. The F(ab')2 constituting a multispecific antigen binding molecule (α) can be suitably obtained by the partial digestion of, for example, a full-length monoclonal antibody having the desired antigen-binding domains with a proteolytic enzyme such as pepsin, followed by the removal of Fc fragments by adsorption on a protein A column. Such a proteolytic enzyme is not particularly limited as long as it is capable of digesting full-length antibodies to restrictively form F(ab')₂ by appropriately setting the enzymatic reaction conditions such as the pH. Examples thereof include pepsin and ficin.

From the viewpoint of obtaining superior cytotoxicity, antibody fragments preferably comprise at least two Fv fragments, and the cancer antigen-binding region and the immune cell antigen-binding region are preferably formed by different Fv regions.

Antibody fragments may or may not comprise an Fc region.

An Fc region may be, for example, an Fc region derived from a naturally occurring IgG or may be an Fc region prepared by artificial introduction of mutations into an Fc region derived from a naturally occurring IgG.

In this context, a naturally occurring IgG means a polypeptide that contains an amino acid sequence identical to that of IgG found in nature and belongs to the class of antibodies substantially encoded by an immunoglobulin gamma gene. A naturally occurring human IgG means, for example, a naturally occurring human IgG1, a naturally occurring human IgG2, a naturally occurring human IgG3, or a naturally occurring human IgG4. A naturally occurring IgG also includes variants or the like that are spontaneously derived therefrom. Examples of the variants include, for example, a plurality of allotype sequences based on gene polymorphism (Sequences of proteins of immunological interest, NIH Publication No. 91-3242). In particular, the sequence of human IgG1 may have DEL or EEM as an amino acid sequence at EU numbering positions 356 to 358.

A multiple antigen-binding molecule (α) preferably does not have an Fc region from the viewpoint of preventing occurrence of side effects due to abnormalities such as overly enhanced activity of immune cells caused by an interference between immune cells recruited by an immune cell antigen-binding region and immune cells recruited by an Fc region. However, even if it has an Fc region, the above-mentioned side effects can be reduced if the Fc region is modified so as to lack the function of recognizing Fcγ receptors.

Amino acid sequences can be modified according to various methods known in the art Examples of these methods include, but are not limited to, site-directed mutagenesis (Hashimoto-Gotoh, T., Mizuno, T., Ogasahara, Y. and Nakagawa, M. (1995) An oligodeoxyribonucleotide-directed dual amber method for site-directed mutagenesis, Gene 152, 271-275; Zoller, M. J. and Smith, M. (1983) Oligonucleotide-directed mutagenesis of DNA fragments cloned into M13 vectors, Methods Enzymol. 100, 468-500; Kramer, W., Drutsa, V., Jansen, H. W., Kramer, B., Pflugfelder, M. and Fritz, H. J. (1984) The gapped duplex DNA approach to oligonucleotide-directed mutation construction, Nucleic Acids Res. 12, 9441-9456; Kramer, W. and Fritz, H. J. (1987) Oligonucleotide-directed construction of mutations via gapped duplex DNA, Methods Enzymol. 154, 350-367; Kunkel, T. A. (1985) Rapid and efficient site-specific mutagenesis without phenotypic selection, Proc. Natl. Acad. Sci. USA 82, 488-492), PCR mutagenesis, cassette mutagenesis, etc.

Whether or not the Fc region is modified so as to lack the function of recognizing an Fcγ receptor can be confirmed by well-known methods such as FACS, ELISA format, ALPHAScreen (Amplified Luminescent Proximity Homogeneous Assay), and the BIACORE method which uses the surface plasmon resonance (SPR) phenomenon (Proc. Natl. Acad. Sci. USA (2006) 103 (11), 4005-4010).

ALPHAScreen is carried out, according to the following principle, based on the ALPHA technology which uses two types of beads (donor and acceptor): molecules bound to the donor beads biologically interact with molecules bound to the acceptor beads, and only when these two beads are located in proximity, a luminescence signal is detected. A laser-excited photosensitizer in the donor beads converts ambient oxygen to singlet oxygen in an excited state. The singlet oxygen diffuses around the donor beads, reaches the acceptor beads located in proximity thereto to thereby cause a chemiluminescent reaction in the beads which finally emit light. In the absence of the interaction between the molecule bound to the donor beads and the molecule bound to the acceptor beads, singlet oxygen produced by the donor beads does not reach the acceptor beads; thus, no chemiluminescent reaction occurs.

For example, a biotin-labeled antigen-binding molecule is allowed to bind to the donor beads, while a glutathione S-transferase (GST)-tagged Fcγ receptor is allowed to bind to the acceptor beads. In the absence of a competing antigen-binding molecule having a mutated Fc region, an antigen-binding molecule having a wild-type Fc region interacts with the Fcγ receptor to generate signals of 520 to 620 nm. The untagged antigen-binding molecule having a mutated Fc region competes with the antigen-binding molecule having a wild-type Fc region for the interaction with the Fcγ receptor. Decrease in fluorescence caused as a result of the competition can be quantified to thereby determine relative binding affinity. Biotinylation of an antigen-binding molecule (e.g., antibody) using sulfo-NHS-biotin or the like is known in the art. An Fcγ receptor can be tagged with GST, by suitably using a method which involves, for example, fusing a polynucleotide encoding the Fcγ receptor in frame with a polynucleotide encoding GST and allowing the resulting fusion gene to be expressed in cells harboring a vector capable of expression thereof or such, followed by purification using a glutathione column. The obtained signals are preferably analyzed using, for example, software GRAPHPAD PRISM (GraphPad Software, Inc., San Diego) adapted to a one-site competition model based on nonlinear regression analysis.

One of the substances between which the interaction is to be observed (ligand) is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other of the substances between which the interaction is to be observed (analyte) is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, bond dissociation gets the signal back to the original position). The Biacore system plots on the ordinate the amount of the shift, i.e., change in mass on the sensor chip surface, and displays time-dependent change in mass as assay data (sensorgram). Kinetics, i.e., the association rate constant (ka) and dissociation rate constant (kd), can be determined from the curve of the sensorgram, while affinity (KD) can be determined from the ratio between these constants. Inhibition assay is also suitably used in the BIACORE method. Examples of the inhibition assay are described in Proc. Natl. Acad. Sci. USA (2006) 103 (11), 4005-4010.

An Fc region lacking the function of recognizing an Fcγ receptor means, for example, an Fc region to be tested having Fcγ receptor-binding activity of 50% or lower, preferably 45% or lower, 40% or lower, 35% or lower, 30% or lower, 20% or lower, or 15% or lower, particularly preferably 10% or lower, 99% or lower, 8% or lower, 7% or lower, 6% or lower, 5% or lower, 4% or lower, 3% or lower, 2% or lower, or 1% or lower as compared with that of a control Fc region based on the analysis method described above.

The control Fc region is, for example, the above-mentioned naturally-occurring IgG-derived Fc region. Furthermore, when an Fc region to be tested is a mutant of an Fc region of a specific isotype antibody, whether or not the mutant lacks the function of recognizing an Fcγ receptor can be examined by using such an Fc region of a specific isotype antibody as the control Fc region.

As such, Fc regions verified to lack the function of recognizing an Fcγ receptor are suitably used as antibody fragments.

Regarding Commonly Shared Light Chains

Preferably, both light chains in an antibody or an antibody fragment having at least two Fv regions have a same amino acid sequence. When both light chains in an antibody or an antibody fragment having at least two Fv regions have a same amino acid sequence, the number of heavy and light chain combinations is decreased; therefore, the step of removing antibodies or antibody fragments having undesired combinations can be facilitated during production. Accordingly, efficiency of production of multiple antigen-binding molecule fusion molecules can be enhanced.

Cancer Tissue-Specific Protease-Cleavable Linker (β)

A cancer tissue-specific protease-cleavable linker (β) comprises a polypeptide containing a sequence targeted by a cancer tissue-specific protease. A cancer tissue-specific protease-cleavable linker (β) nay have only a target sequence for a cancer tissue-specific protease, or it may have, in addition to the target sequence, a peptide linker fused thereto. An example of such a peptide linker is a linker that is the same as the above-mentioned linker that links the variable regions.

Cancer tissue-specific protease-cleavable linkers (β) are hydrolyzed by cancer tissue-specific proteases in cancer tissues. When cancer tissue-specific protease-cleavable linkers (β) are hydrolyzed, masking molecules (γ) become dissociable from multiple antigen-binding molecules (α). Upon dissociation of the masking molecules (γ) from the multiple antigen-binding molecules (α), the immune cell antigen-binding regions in the multiple antigen-binding molecules (α) become capable of binding to immune cells.

Furthermore, the cancer tissue-specific protease-cleavable linkers (β) have a function of serving as a spacer so that the masking molecules (γ) can mask the immune cell antigen-binding regions in the multiple antigen-binding molecules (α).

Regarding Target Sequences for Cancer Tissue-Specific Proteases

Examples of cancer tissue-specific proteases include proteases specifically expressed in cancer tissues as disclosed in WO2013/128194, WO2010/081173, WO2009/025846, and such. While not construed as being limited thereto, specific examples of the proteases include cysteine proteases (including the cathepsin family B, L, S, etc.), aspartyl proteases (including cathepsin D, E, K, O, etc.), serine proteases (including cathepsin A and G, thrombin, plasmin, urokinase (uPA), tissue plasminogen activator (tPA)), metalloproteinases (metalloproteinases (MMP1-28) including both membrane-bound form (MMP14-17 and MMP24-25) and secreted form (MMP1-13 and MMP18-23 and MMP26-28), a-disintegrin-and-metalloproteinase (ADAM) proteases, a-disintegrin and metalloproteinase with Thrombospondin motifs (ADAMTS)), CD10 (CALLA), and prostate specific antigens (PSA).

Regarding the types of cancer tissue-specific proteases, as they are expressed in a highly tissue-specific manner in cancer tissues to be treated, a side-effect-decreasing effect provided by the masking molecule (γ) becomes greater. The concentration of a cancer tissue-specific protease in a cancer tissue is higher than in a normal tissue preferably by 5-fold or more, more preferably by 10-fold or more, even more preferably by 100-fold or more, and particularly preferably by 500-fold or more, and most preferably by 1000-fold or more.

Furthermore, cancer tissue-specific proteases nay be bound to the cell membrane of cancer cells, or may be unbound to the cell membrane but extracellularly secreted. When cancer tissue-specific proteases are not bound to the cancer cell membrane, cancer tissue-specific proteases are preferably present near or inside cancer tissues in order for immune cells to be specific to cancer cells. Herein, "near cancer tissues" means within a range where cancer cells are damaged by immune cells recruited by the multiple antigen-binding molecule (α) upon cleavage of the cancer tissue-specific protease-cleavable linker (β). It is preferably, however, a range where damage to normal cells is avoided as much as possible.

Cancer tissue-specific proteases may be a single type alone or a combination of two or more types. The number of types of cancer tissue-specific proteases can be appropriately set by those skilled in the art by considering the types of cancers subjected to treatment.

In view of the above, preferred cancer tissue-specific proteases among the proteases presented as examples above are metalloproteinases, and while MMP-2 and MMP-9 are preferred among the metalloproteinases, MMP-2 is more preferred.

A target sequence is a specific amino acid sequence that is specifically recognized by a cancer tissue-specific protease when the target polypeptide is hydrolyzed in an aqueous solution by the cancer tissue-specific protease.

From the viewpoint of reduction of side effects, the target sequence is preferably an amino acid sequence hydrolyzed with high specificity by a cancer tissue-specific protease expressed in a highly tissue-specific manner in cancer tissues to be treated.

Specific target sequences are, for example, target sequences that are specifically hydrolyzed by proteases expressed specifically in cancer tissues presented as examples above, and are disclosed in WO2013/128194, WO2010/081173, WO2009/025846, and such. Alternatively, sequences identified by methods known to those skilled in the art, such as the method described in Nature Biotechnology 19, 661-667 (2001), may be used as the target sequence.

Target sequences are preferably amino acid sequences that are specifically hydrolyzed by MMP-2 which is a preferred cancer tissue-specific protease, as described above. Among the amino acid sequences specifically hydrolyzed by MMP-2, the following amino acid sequence (SEQ ID NO: 9) is preferred: PLGLAG (SEQ ID NO: 9)

The cancer tissue-specific protease-cleavable linkers (β) may be linked to any position of the multiple antigen-binding molecules (α). Considering accessibility to an immune cell antigen-binding region in a multiple antigen-binding molecule (α) by a masking molecule (γ) and producibility of the masking effect on the immune cell antigen-binding region, a cancer tissue-specific protease-cleavable linker (β) is preferably linked to the immune cell antigen-binding region in the multiple antigen-binding molecule (α).

Figure 3:
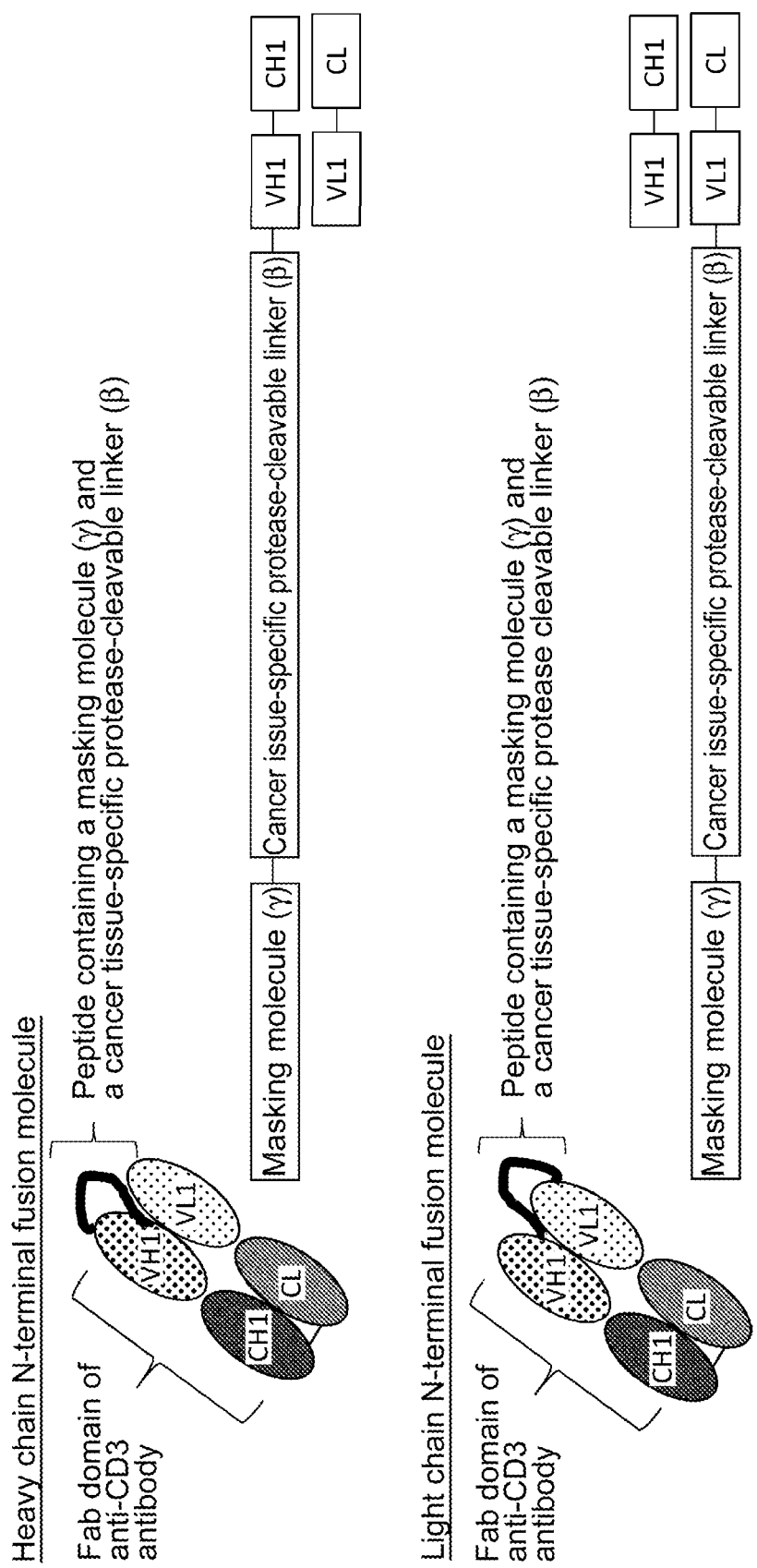
FIG. 3 shows a partial conceptual diagram of another embodiment of a multiple antigen-binding molecule fusion molecule of the present invention. The upper figure shows a heavy-chain N-terminal fusion molecule and the lower figure shows a light-chain N-terminal fusion molecule.

When a multiple antigen-binding molecule (α) is a multispecific antibody, and a cancer antigen-binding region and an immune cell antigen-binding region are formed by different Fv regions, a cancer tissue-specific protease-cleavable linker (β) is preferably fused to the heavy chain N terminus or light chain N terminus of the Fv region (Fab region) on the side that forms the immune cell antigen-binding region (see FIG. 3; those shown in the figure are referred to respectively as "heavy chain N-terminal fusion molecule" and "light chain N-terminal fusion molecule"). When the cancer tissue-specific protease-cleavable linker (β) is fused to the heavy chain N terminus or light chain N terminus of the Fv region on the side that forms the immune cell antigen-binding region, it is not necessary to perform a step of linking the cancer tissue-specific protease-cleavable linker (β) after preparation of the multiple antigen-binding molecule (α), and this provides excellent efficiency of producing multiple antigen-binding molecule fusion molecules. Furthermore, as described later, this also makes it easy to set the amino-acid lengths of the cancer tissue-specific protease-cleavable linker (β) and the masking molecule (γ).

Cancer tissue-specific protease-cleavable linkers (β) can be obtained, for example, by known methods for producing polypeptides.

Masking Molecule (γ)

A masking molecule (γ) comprises a polypeptide consisting of the amino acid sequence QDGNE (SEQ ID NO: 15). The polypeptide consisting of the amino acid sequence QDGNE (SEQ ID NO: 15) is a human CD3ε partial peptide which is derived from human CD3ε.

The masking molecules (γ) mask the immune cell antigen-binding regions of the multiple antigen-binding molecules (α) in multiple antigen-binding molecule fusion molecules and thus have a function to prevent the binding of the immune cell antigen-binding regions to immune cell antigens. Masking of an immune cell antigen-binding region by a masking molecule (γ) nay take place intermolecularly between multiple antigen-binding molecule fusion molecules, and these multiple antigen-binding molecule fusion molecules may be in the form of a complex. The function can be exhibited under such state as well.

In cancer tissues, the above-described cancer tissue-specific protease-cleavable linkers (β) are cleaved by cancer tissue-specific proteases expressed in the cancer tissues. Consequently, the masking molecules (γ) become dissociable from the multiple antigen-binding molecules (α). When the masking molecules (γ) dissociate from the multiple antigen-binding molecule fusion molecules, the immune cell antigen-binding regions of the multiple antigen-binding molecules (α) become capable of binding to immune cell antigens.

On the other hand, in normal tissues, cancer tissue-specific proteases are not expressed, or even if they are expressed, their concentrations are low; thus, under such an environment where the cancer tissue-specific protease-cleavable linkers (β) are unlikely to be cleaved, the masking molecules (γ) cannot dissociate from the multiple antigen-binding molecules (α), and the masking effect on the immune cell antigen-binding regions is maintained. That is, in normal tissues, the masking molecules (γ) bind to the multiple antigen-binding molecules (α) via the cancer tissue-specific protease-cleavable linkers (β) to thereby mask the immune cell antigen-binding regions, which makes it difficult to recruit immune cells; and therefore, side effects caused by the multiple antigen-binding molecules (α) is reduced.

The masking molecules (γ) may or may not have an amino acid sequence other than the amino acid sequence QDGNE (SEQ ID NO: 15). In either case, they can sufficiently exhibit the masking effects under the conditions where the cancer tissue-specific protease-cleavable linkers (β) are not cleaved, and they easily dissociate from the multiple antigen-binding molecules (α) under the conditions where the cancer tissue-specific protease-cleavable linkers (β) have been cleaved.

From the viewpoint of improving the stability of the masking molecules (γ) and preventing the masking effect from being reduced due to binding with CD3γ or CD3δ, the masking molecules (γ) preferably do not have an amino acid sequence other than the amino acid sequence QDGNE (SEQ ID NO: 15).

When the masking molecules (γ) contain an amino acid sequence other than the amino acid sequence QDGNE (SEQ ID NO: 15), they are preferably human CD3ε partial polypeptides. In terms of improving the stability of the masking molecules (γ) and in terms of preventing the masking effects from being reduced due to binding with CD3γ or CD3δ, a human CD3ε partial polypeptide is preferably a linear peptide (linear epitope) to which an immune cell antigen-binding region may bind. Use of a linear peptide can suppress an increase of the molecular weight of the multiple antigen-binding molecule fusion molecules, suppress an increase of the dose, and reduce the burden on the patients.

Specifically, the human CD3ε partial polypeptide is preferably a human CD3ε partial polypeptide having the amino acid sequence QDGNE (SEQ ID NO: 15) at the N terminus and containing 30 or fewer amino acids, more preferably a human CD3ε partial polypeptide having the amino acid sequence QDGNE (SEQ ID NO: 15) at the N terminus and containing 25 or fewer amino acids, even more preferably a human CD3ε partial polypeptide having the amino acid sequence QDGNE (SEQ ID NO: 15) at the N terminus and containing 20 or fewer amino acids, particularly preferably a human CD3ε partial polypeptide having the amino acid sequence QDGNE (SEQ ID NO: 15) at the N terminus and containing 15 or fewer amino acids, and most preferably a human CD3ε partial polypeptide having the amino acid sequence QDGNE (SEQ ID NO: 15) at the N terminus and containing ten or fewer amino acids.

The masking molecules (γ) may be chemically modified. The chemical modifications may be known modifications. Examples of the chemical modifications include acetylation, alkylation, and pyroglutamylation. Among the modifications, pyroglutamylation of Q in the amino acid sequence QDGNE (SEQ ID NO: 15) is preferred.

The masking molecules (γ) are obtained by a known method for producing polypeptides. Furthermore, when it is chemically modified, modifications can be carried out by known methods for chemical modification of polypeptides.
Amino Acid Lengths of a Cancer Tissue-Specific Protease-Cleavable Linker (β) and a Masking Molecule (γ)

When a cancer tissue-specific protease-cleavable linker (β) and a masking molecule (γ) constitute a linear fusion polypeptide, the total amino acid length of the cancer tissue-specific protease-cleavable linker (β) and the masking molecule (γ) may be optimized to sufficiently obtain the masking effect of the masking molecule (γ) on the immune cell antigen-binding region.

When the cancer tissue-specific protease-cleavable linker (β) is fused to the heavy-chain N-terminus of the Fv region that forms the immune cell antigen-binding region (upper panel in FIG. 3), the number of amino acids of the fusion polypeptide is preferably eleven or more to 65 or less, more preferably 14 or more to 27 or less, and most preferably 17 or more to 20 or less.

When the cancer tissue-specific protease-cleavable linker (β) is fused to the light-chain N-terminus of the Fv region that forms the immune cell antigen-binding region (lower panel in FIG. 3), the number of amino acids in the fusion polypeptide is preferably 16 or more to 65 or less, more preferably 17 or more to 30 or less, and most preferably 19 or more to 25 or less.
Methods for Producing a Multiple Antigen-Binding Molecule Fusion Molecule Examples of methods for producing multiple antigen-binding molecule fusion molecules include a method in which a multiple antigen-binding molecule (α), a cancer tissue-specific protease-cleavable linker (β), and a masking molecule (γ) are prepared individually, and the multiple antigen-binding molecule (α) and the masking molecule (γ) are bonded to the cancer tissue-specific protease-cleavable linker (β).

The types of bonds used in this method are not particularly limited so long as the multiple antigen-binding molecule (α) and the masking molecule (γ) are chemically bonded to the cancer tissue-specific protease-cleavable linker (β). Among chemical bonds, covalent bonds are preferred, and covalent bonds formed by peptide bonds are more preferred.

In addition to this method, when the multiple antigen-binding molecule fusion molecules are fusion proteins or an assembly of fusion proteins which may be glycosylated, the multiple antigen-binding molecule fusion molecules may be produced by a known protein expression method, for example, a method that uses host cells and an expression vector in combination.

In the case of using eukaryotic cells as the host cells, animal cells, plant cells, or fungus cells can be appropriately used. Specifically, examples of the animal cells can include the following cells:

(1) mammalian cells: CHO (Chinese hamster ovary cell line), COS (monkey kidney cell line), myeloma (Sp2/O, NS0, etc.), BHK (baby hamster kidney cell line), HEK293 (human embryonic kidney cell line with sheared adenovirus (Ad)5 DNA), PER.C6 cell (human embryonic retinal cell line transformed with the Adenovirus Type 5 (Ad5) E1A and E1B genes), Hela, and Vero, or such (Current Protocols in Protein Science (May, 2001, Unit 5.9, Table 5.9.1));

(2) amphibian cells: *Xenopus oocytes* or such; and (3) insect cells: sf9, sf21, Tn5, or such.

The multiple antigen-binding molecule fusion molecules can also be prepared using *E. coli*((mAbs 2012 March-April; 4 (2): 217-225) or yeast (WO2000/023579). Multiple antigen-binding molecule fusion molecules prepared using *E. coli* are not glycosylated. On the other hand, multiple antigen-binding molecule fusion molecules prepared using yeast are glycosylated.

Expression vectors may be suitably selected by the skilled artisan depending on the type of host cells.

The multiple antigen-binding molecule fusion molecules can be collected, for example, by culturing transformed cells and then separating the multiple antigen-binding molecule fusion molecules from within the molecule-transformed cells or from the culture media. The multiple antigen-binding molecule fusion molecules can be separated and purified by appropriately using in combination methods such as centrifugation, ammonium sulfate fractionation, salting out, ultrafiltration, C1q, FcRn, protein A and protein G columns, affinity chromatography, ion-exchange chromatography, and gel filtration chromatography.

The techniques mentioned above, such as the knobs-into-holes technology (WO1996/027011; Ridgway J B et al., Protein Engineering (1996) 9, 617-621; and Merchant A M et al., Nature Biotechnology (1998) 16, 677-681) or the technique of suppressing unintended association between H chains by introduction of electric charge repulsion (WO2006/106905 and WO2015/046467), can be applied as methods for efficiently preparing the multiple antigen-binding molecule fusion molecules.
B. Pharmaceutical Compositions Pharmaceutical compositions of the present invention contain an above-mentioned multiple antigen-binding molecule fusion molecule and a pharmaceutically acceptable carrier. Pharmaceutical compositions can be nude to contain an above-mentioned multiple antigen-binding molecule fusion molecule and a pharmaceutically acceptable carrier, and can be formulated by known methods.

For example, the pharmaceutical compositions can be used in the form of a parenteral injection of an aseptic solution or suspension with water or any other pharmaceutically acceptable solution. For example, the pharmaceutical compositions nay be formulated by mixing the molecule in a unit dosage form required for generally accepted pharmaceutical practice in appropriate combination with a pharmacologically acceptable carrier or medium, specifically, sterilized water, physiological saline, plant oil, an emulsifier, a suspending agent, a surfactant, a stabilizer, a flavoring agent, an excipient, a vehicle, a preservative, a binder, or such. Specific examples of the carrier include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium-chain fatty acid triglyceride, polyoxyethylene hydrogenated castor oil 60, saccharose, carboxymethylcellulose, cornstarch, and inorganic salts. The amount of active ingredients in these formulations is adjusted to achieve an appropriate dose within a prescribed range.

An aseptic composition for injection can be formulated according to conventional pharmaceutical practice using a vehicle such as injectable distilled water. Examples of aqueous solutions for injection include physiological saline, isotonic solutions containing glucose and other adjuvants, for example, D-sorbitol, D-nannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, polysorbate 80 or HCO-50.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), or an antioxidant. The injection solutions thus prepared are usually charged into appropriate ampules.

A preferred administration is parenteral administration, and specific examples of dosage forms include injections, intranasal administration agents, transpulmonary administration agents, and percutaneous administration agents. Examples of injections include intravenous injection, intramuscular injection, intraperitoneal injection, and subcutaneous injection, through which systemic or local administration can be done.

The administration method can be appropriately selected depending on the age and symptoms of a patient. The dose of the pharmaceutical composition containing a multiple antigen binding molecule fusion molecule and a pharmaceutically acceptable carrier can be selected within a range of; for example, 0.0001 to 1000 mg/kg of body weight per dose. Alternatively, the dose can be selected within a range of; for example, 0.001 to 100000 mg/body of a patient, though the dose is not necessarily limited to these numeric values. Although the dose and the administration method vary depending on the weight, age, symptoms, and such of a patient, those skilled in the art can appropriately select the dose and the method.

The pharmaceutical compositions are preferably for cancer treatment. Preferably, cancer types to be treated specifically express cancer antigens recognized by the cancer antigen-binding regions in the multiple antigen-binding molecules (α) included in the multiple antigen-binding molecule fusion molecules to be used. The cancer types to be treated nay be solid cancers or blood cancers.

The pharmaceutical compositions of the present invention can provide methods for treating cancer which comprise administering the pharmaceutical compositions to patients.

C. Methods for Identifying Linear Epitopes

Methods for identifying a linear epitope of the present invention comprise a step of identifying, based on three-dimensional protein structure analysis data obtained by using a protein complex formed between an immune cell antigen and an immune cell antigen-binding region that recognizes the immune cell antigen, a linear epitope included in the immune cell antigen and recognized by the immune cell antigen-binding region.

The immune cell antigen-binding region, depending on the type thereof, may recognize a linear peptide portion in an immune cell antigen or may recognize a higher-order structure portion of a polypeptide forming a higher-order structure. The method for identifying a linear epitope of the present invention is a method for identifying a linear peptide to which the immune cell antigen-binding region is capable to bind, where the immune cell antigen-binding region recognizes a linear peptide portion in an immune cell antigen.

The identified linear peptides are useful as a masking molecule (γ) which does not require the formation of a higher-order structure. Since linear peptides do not require formation of higher-order structures, they can stably exhibit a masking effect.

D. Methods for Producing Multiple Antigen-Binding Molecule Fusion Molecules

Methods for producing multiple antigen-binding molecule fusion molecules of the present invention comprise a step of expressing a fusion protein in which a linear epitope (for example, a linear epitope identified by the above-mentioned method for identifying linear epitopes) is fused to a multiple antigen-binding molecule (α) containing a cancer antigen-binding region which recognizes a cancer antigen and an immune cell antigen-binding region which recognizes an immune cell antigen via a cancer tissue-specific protease-cleavable linker (β) containing a region that may be cleaved by a protease specifically expressed in a cancer tissue expressing said cancer antigen.

The multiple antigen-binding molecules (α) and the cancer tissue-specific protease-cleavable linkers (β) are the same as those described above under "A. Multiple antigen-binding molecule fusion molecules".

The linear epitope is not particularly limited, but is acceptable if it satisfies the definition given herein.

The linear epitope may be a linear epitope identified by the above-described method for identifying a linear epitope, or it may be one identified by such known epitope mapping methods that ELISA, mass spectrometry, phage library, and such are performed using partial peptides of various antigens. The linear epitope is preferably a linear epitope identified by the above-mentioned method for identifying linear epitopes from the viewpoint that the binding state between an immune cell antigen and the immune cell antigen-binding region can be analyzed in detail and with accuracy to thereby obtain a minimal unit of the epitope, and from the viewpoint that acquisition of a minimal unit of the epitope makes it possible to obtain a multiple antigen-binding molecule fusion molecule that can stably exhibit a masking effect without requiring the formation of higher-order structures.

E. Functional Effects of the Present Invention

The multiple antigen-binding molecule fusion molecules of the present invention are specifically activated by proteases present inside or near cancer tissues, and can recruit immune cells such as T cells to cancer cells. Therefore, the multiple antigen-binding molecules that recognize cancer antigens and CD3 can produce excellent side-effect-reducing effects.

In the multiple antigen-binding molecule fusion molecules of the present invention, masking molecules comprising a polypeptide having the amino acid sequence QDGNE (SEQ ID NO: 15) are used. Such masking molecules only need to carry at least a polypeptide consisting of the amino acid sequence QDGNE (SEQ ID NO: 15), and are easily produced due to their smaller molecular weight as compared to the masking molecule disclosed in WO2013/128194. Because the molecular weight of the masking molecules can be lowered, the molecular weight of the multiple antigen-binding molecule fusion molecules can be lowered, the dose can be decreased, and the burden on the patients can be reduced.

CD3ε is generally known to form a homodimer or a heterodimer with CD3γ or CD3δ (Scand. J. Immunol. 2002

Vol. 56, pp. 436-442). Therefore, the stability of CD3ε or a partial protein of CD3ε may be lowered when it exits as a monomer. Furthermore, when CD3ε or a partial protein of CD3ε is used as a masking molecule, it nay readily form a dimer with each other or with endogenous proteins, and a sufficient masking effect may not be readily obtained.

On the other hand, since the masking molecules in the multiple antigen-binding molecule fusion molecules of the present invention only need to have at least a polypeptide consisting of the amino acid sequence QDGNE (SEQ ID NO: 15), they have excellent stability and masking effects.

The epitope of the antigen-binding region of OKT3, which is an anti-CD3ε antibody used in WO2013/128194, is not shared between humans and cynomolgus monkeys. Therefore, OKT3 is an antibody specific to human CD3ε, and it has not been found to bind to cynomolgus CD3s. Because of this, non-clinical toxicity tests using cynomolgus monkeys cannot be carried out, or even if non-clinical toxicity tests using cynomolgus monkeys were carried out, they would not reflect the results of clinical trials.

In contrast, the amino acid sequence QDGNE (SEQ ID NO: 15) in an antigen recognized by the immune cell antigen-binding regions of the present invention is the same in humans and cynomolgus monkeys. Therefore, the test results obtained in non-clinical toxicity tests using cynomolgus monkeys will be likely to reflect the results of clinical trials.

All references cited herein are incorporated herein by reference in their entirety.

Those skilled in the art should understand that one of or any combination of two or more of the aspects described herein is also included in the present invention unless a technical contradiction arises on the basis of the technical common sense of those skilled in the art.

EXAMPLES

The present invention will be further illustrated with reference to Examples below. However, the present invention is not intended to be limited by Examples below.

Figure 2:
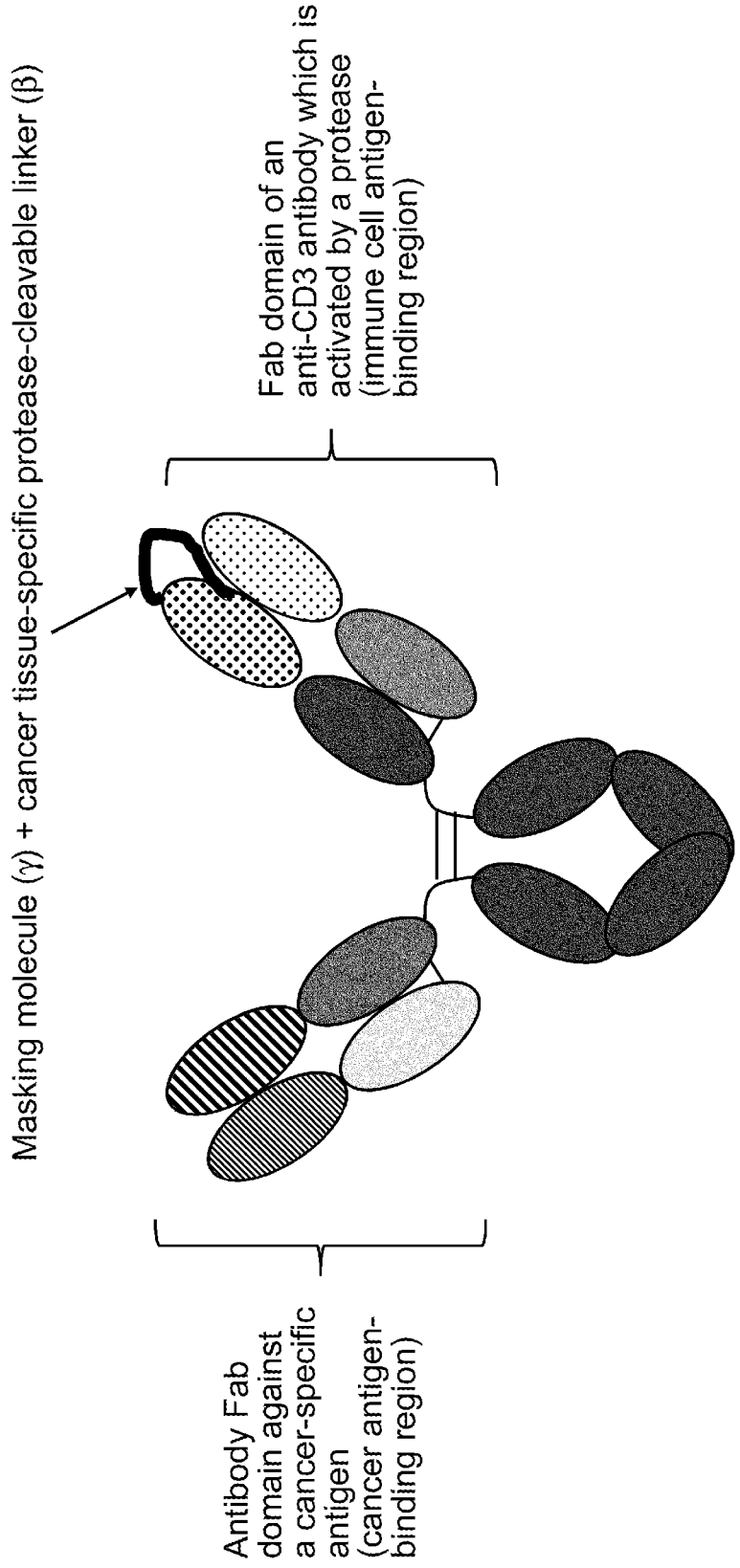
FIG. 2 shows an overall conceptual diagram of an embodiment of a multiple antigen-binding molecule fusion molecule of the present invention.

Example 1: Concept of an Anti-Cancer Antigen/Anti-CD3 Multiple Antigen-Binding Molecule Fusion Molecule Activated by a Protease Anti-cancer antigen/anti-CD3 multiple antigen-binding molecule is expected to be a promising molecular format of anti-cancer agents due to its potent cytotoxic activity, but on the other hand, if the cancer antigen is expressed even slightly in normal tissues, the molecule nay exhibit a damaging activity on the normal tissues as well; therefore, anti-cancer antigen/anti-CD3 multiple antigen-binding molecules with few side effects and having superior safety properties are desired. In this regard, if an anti-cancer antigen/anti-CD3 multiple antigen-binding molecule can be derivatized to produce an anti-cancer antigen/anti-CD3 multiple antigen-binding molecule fusion molecule which is activated by proteases, an anti-cancer antigen/anti-CD3 multiple antigen-binding molecule with few side effects and superior safety properties can be prepared easily (FIG. 2).

For the protease-activatable anti-cancer antigen/anti-CD3 multiple antigen-binding molecule fusion molecules to have further reduced side effects and superior safety properties, it is preferable that the molecules have the following three structural features. The first feature is that a masking molecule (γ) which inhibits the binding activity of an anti-CD3 antibody is linked to the heavy-chain N terminus or the light-chain N terminus of an anti-CD3 antibody variable region via a cancer tissue-specific protease-cleavable linker (β). The second feature is that the masking molecule (γ) is comprised of a naturally-occurring epitope sequence of the anti-CD3 antibody and does not contain any non-natural sequence from the viewpoint of immunogenicity, and homology of the corresponding amino acid sequences between species (for example, between human and cynomolgus monkey) is high. The third feature is that the cancer tissue-specific protease-cleavable linker (β) contains a target sequence that is cleaved by a protease present at high concentration inside or near cancer tissues.

Reference Example 1: Preparation of Anti-Human and Anti-Cynomolgus Monkey CD3ε Antibody "CE115"

1-1. Preparation of Hybridoma Using Rat Immunized with Cell Expressing Human CD3 and Cell Expressing Cynomolgus Monkey CD3

Each SD rat (female, 6 weeks old at the start of immunization, Charles River Laboratories Japan, Inc.) was immunized with Ba/F3 cells expressing human CD3εγ or cynomolgus monkey CD3εγ as follows: at day 0 (the priming date was defined as day 0), $5 \times 10^7$ Ba/F3 cells expressing human CD3εγ were intraperitoneally administered together with a Freund complete adjuvant (Difco Laboratories, Inc.) to the rat. At day 14, $5 \times 10^7$ Ba/F3 cells expressing cynomolgus monkey CD3εγ were intraperitoneally administered together with a Freund incomplete adjuvant (Difco Laboratories, Inc.). Then, $5 \times 10^7$ Ba/F3 cells expressing human CD3εγ and Ba/F3 cells expressing cynomolgus monkey CD3εγ were intraperitoneally administered thereto a total of four times every other week in an alternate manner. One week after (at day 49) the final administration of CD3εγ, Ba/F3 cells expressing human CD3εγ were intravenously administered as a booster. Three days thereafter, spleen cells of the rats were fused with mouse myeloma cells SP2/0 according to a conventional method using Pebg 1500 (Roche Diagnostics K.K.). Fusion cells, i.e., hybridomas, were cultured in an RPMI1640 medium containing 10% FBS (hereinafter, referred to as 10% FBS/RPMI1640).

On the day after the fusion, (1) the fusion cells were suspended in a semifluid medium (Stem cell Technologies, Inc.). The hybridomas were selectively cultured and also colonized.

Figure 4:
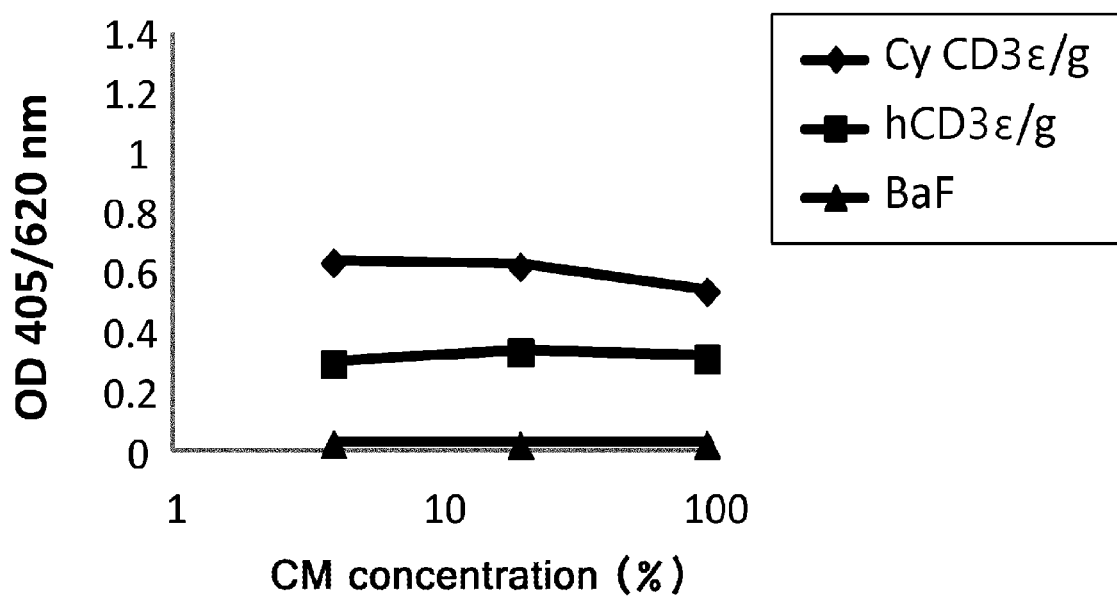
FIG. 4 is a graph showing the results of cellular ELISA for CE115 against CD3ε.

Nine or ten days after the fusion, hybridoma colonies were picked up and inoculated at 1 colony/well to a 96-well plate containing a HAT selective medium (10% FBS/RPMI1640, 2 vol % HAT 50×concentrate (Sumitomo Dainippon Pharma Co., Ltd.), and 5 vol % BM-Condimed H1 (Roche Diagnostics K.K.)). After 3- to 4-day culture, the culture supernatant in each well was recovered, and the rat IgG concentration in the culture supernatant was measured. The culture supernatant confirmed to contain rat IgG was screened fora clone producing an antibody specifically binding to human CD3εγ by cell-ELISA using attached Ba/F3 cells expressing human CD3εγ or attached Ba/F3 cells expressing no human CD3εγ (FIG. 4). The clone was also evaluated for cross-reactivity with monkey CD3εγ by cell-ELISA using attached Ba/F3 cells expressing cynomolgus monkey CD3εγ (FIG. 4).

1-2. Preparation of Anti-Human and Anti-Monkey CD3ε Chimeric Antibody

Total RNA was extracted from each hybridoma cells using RNeasy Mini Kits (Qiagen N.V.), and cDNA was synthesized using SMART RACE cDNA Amplification Kit (BD Biosciences). The prepared cDNA was used in PCR to insert the antibody variable region gene to a cloning vector. The nucleotide sequence of each DNA fragment was determined using BigDye Terminator Cycle Sequencing Kit (Applied Biosystems, Inc.) and a DNA sequencer ABI PRISM 3700 DNA Sequencer (Applied Biosystems, Inc.) according to the method described in the instruction manual included therein. CDRs and FRs of the CE115 H chain variable domain and the CE115 L chain variable domain were determined according to the Kabat numbering.

A rat anti-CD3 antibody comprising a heavy chain variable region (SEQ ID NO: 10) and a light chain variable region (SEQ ID NO: 11) as well as a humanized anti-CD3 antibody comprising a heavy chain variable region (SEQ ID NO: 12) and a light chain variable region (SEQ ID NO: 13), which was humanized using a method known to those skilled in the art, were prepared.

Reference Example 2: Preparation of Antibody Expression Vector and Expression and Purification of Antibody Amino acid substitutions was carried out by a method generally known to those skilled in the art using QuikChange Site-Directed Mutagenesis Kit (Stratagene Corp.), PCR, or In fusion Advantage PCR cloning kit (Takara Bio Inc.), etc., to construct expression vectors. The obtained expression vectors were sequenced by a method generally known to those skilled in the art. The prepared plasmids were transiently transferred to human embryonic kidney cancer cell-derived HEK293H line (Invitrogen Corp.) or FreeStyle 293 cells (Invitrogen Corp.) to express antibodies. Each antibody was purified from the obtained culture supernatant by a method generally known to those skilled in the art using rProtein A Sepharose (registered trademark) Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by PACE (Protein Science 1995; 4: 2411-2423).

Example 2: X-Ray Crystallographic Analysis of a Complex Formed Between Anti-CD3 Antibody and CD3

An anti-CD3 antibody consisting of a heavy chain (variable region (SEQ ID NO: 12) and a constant region (SEQ ID NO: 38)), a light chain (variable region (SEQ ID NO: 13) and a constant region (SEQ ID NO: 36)), and Kn010G3 (SEQ ID NO: 37) was expressed and prepared as a One-arm antibody by the method of Reference Example 1. Anti-CD3 antibody Fab fragment was prepared from the obtained One-arm antibody by performing cleavage treatment using papain protease (Roche Applied Science), removal of Fc fragments using a Protein A column, and purification using a cation exchange column and a gel filtration column, according to methods known to those skilled in the art.

The obtained anti-CD3 antibody Fab fragment was concentrated by ultrafiltration, and crystals were obtained by the vapor diffusion method, in which the Fab fragment was left to stand at 20° C. under reservoir conditions of 200 mM Potassium Sulfate and 20% PEG3350. X-ray crystallography was performed using the obtained crystals based on known Fab fragment crystal structures according to a method known to those skilled in the art to obtain the crystal structure of the anti-CD3 antibody Fab fragment alone from the diffraction intensity data at 25 to 2.12 angstrom resolution. Its crystallographic reliability factor R (R factor) and Free R value (R free) were 22.21% and 26.28%, respectively.

Furthermore, a sample was prepared by adding, to the obtained anti-CD3 antibody Fab fragment, a synthetic peptide (epitope peptide) which corresponds to the sequence from the N terminus to position 15 of CD3 and shown in SEQ ID NO: 14 below: XDGNEEMGGITQTPY (X: L-pyroglutamic acid) (SEQ ID NO: 14) to become 2 mM. The vapor diffusion method was used to obtain crystals from the sample by allowing the sample to stand at 20° C. under reservoir conditions of 100 mM MES buffer at pH7.0, 0.91% PEG3350, and 1.0 M sodium citrate tribasic dihydrate. These crystals were subject to X-ray crystallography based on the above-mentioned crystal structure of the anti-CD3 antibody Fab fragment alone according to a method known to those skilled in the art to obtain the crystal structure of a complex of the anti-CD3 antibody Fab fragment and the epitope peptide from the diffraction intensity data at 25 to 3.5 angstrom resolution. Its crystallographic reliability factor R (R factor) and Free R value (R free) were 18.55% and 26.53%, respectively.

Figure 5:
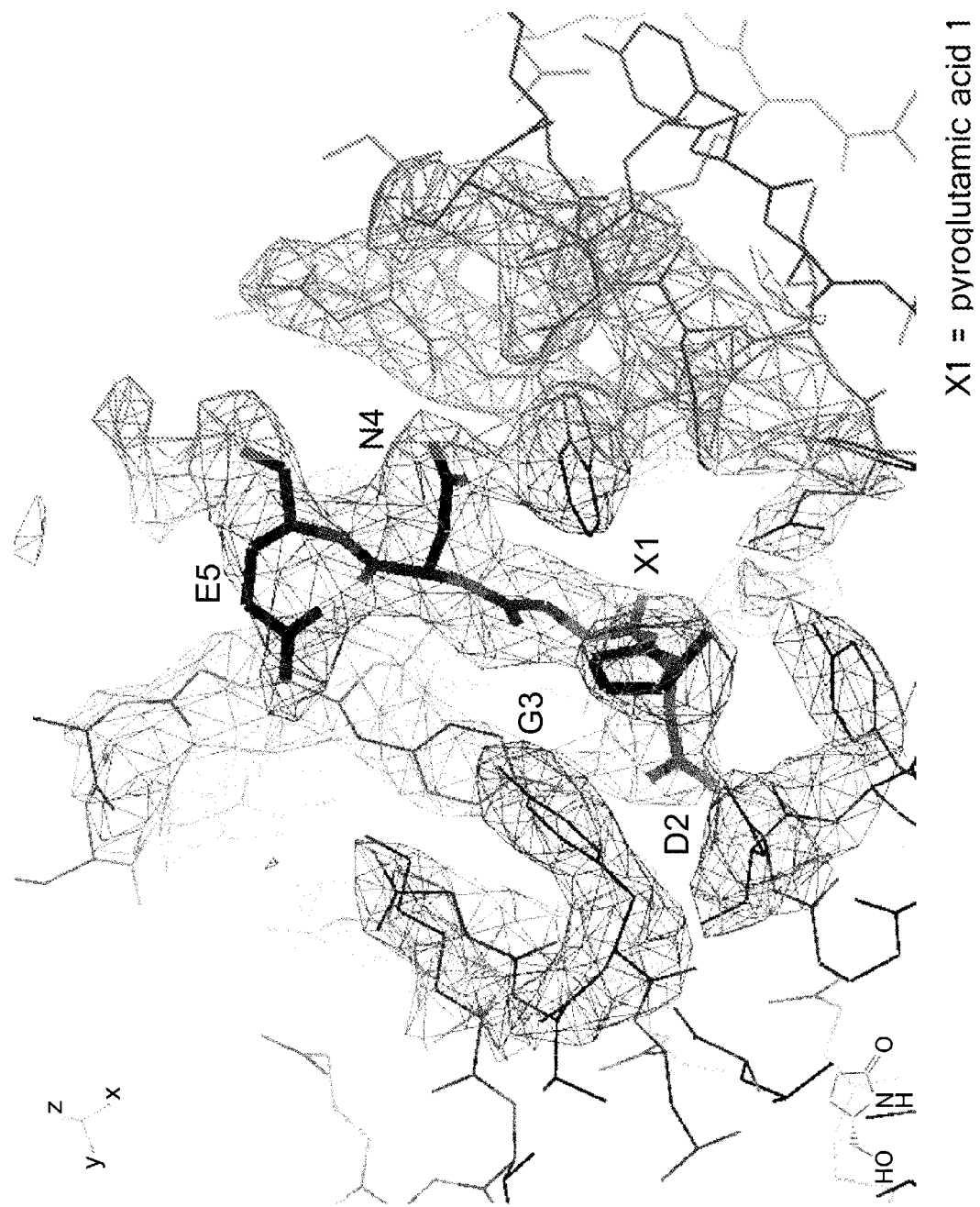
FIG. 5 shows a 2Fo-Fc electron density nap of the binding site of an anti-CD3 antibody Fab fragment and an epitope peptide. In the figure, the antibody is indicated by thin lines, and the epitope peptide is indicated by thick lines. Each of the amino acid residues of the epitope peptide from the N-terminus to the fifth amino acid residue is represented by a one-letter amino acid code and the serial number from the N-terminal side. The electron density map is shown as a mesh.
Figures 1, 11:
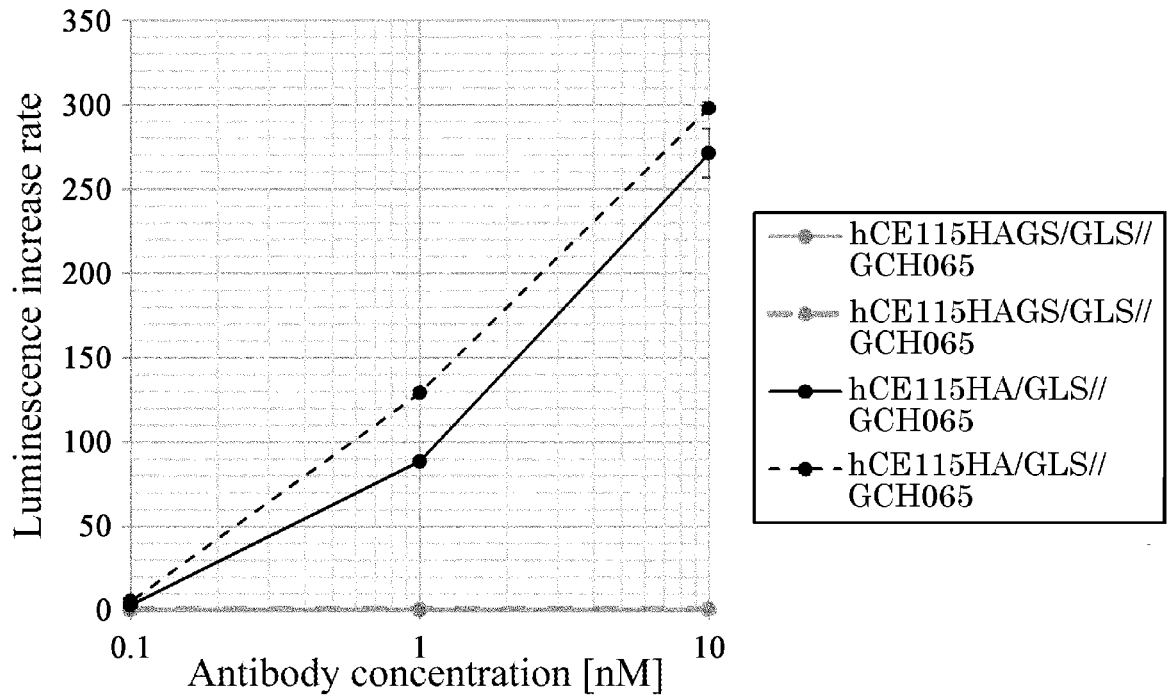
Figures 2, 11:
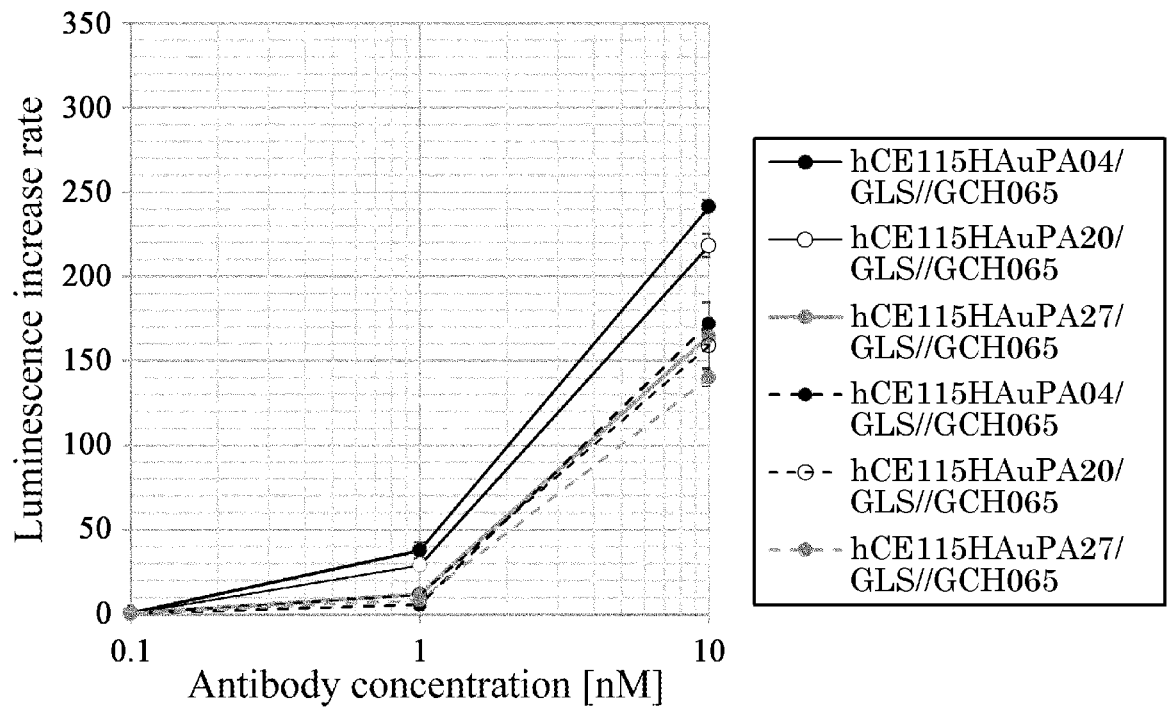
Figures 1, 12:
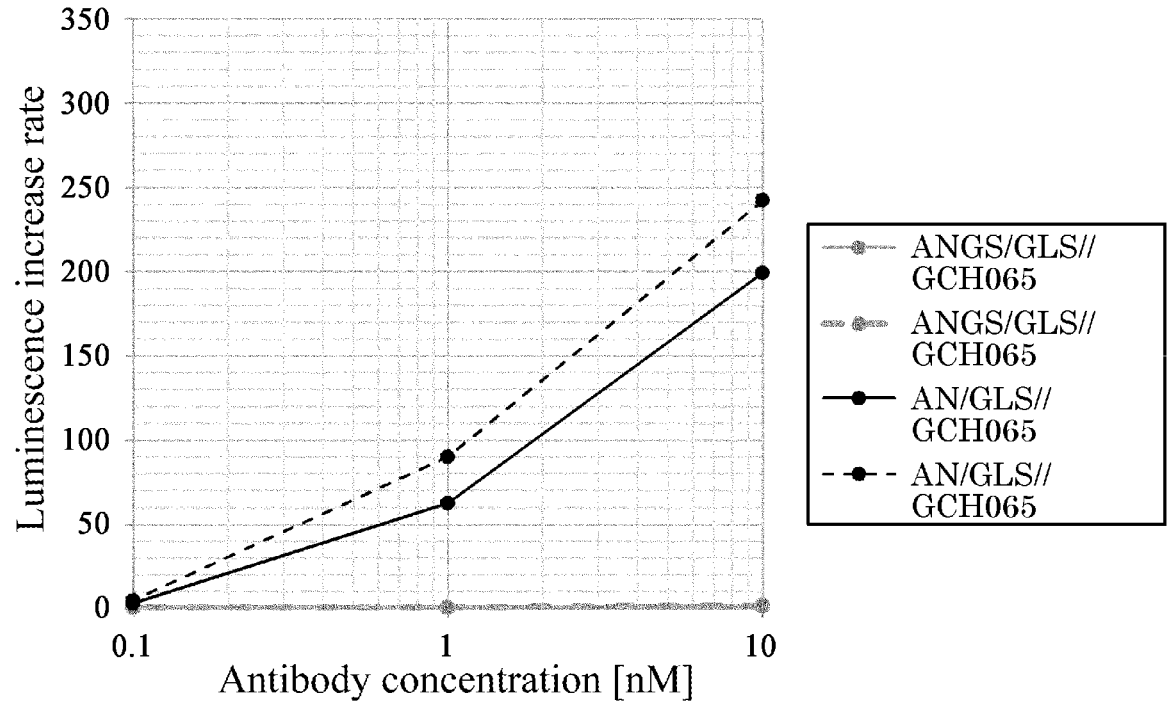
Figures 2, 12:
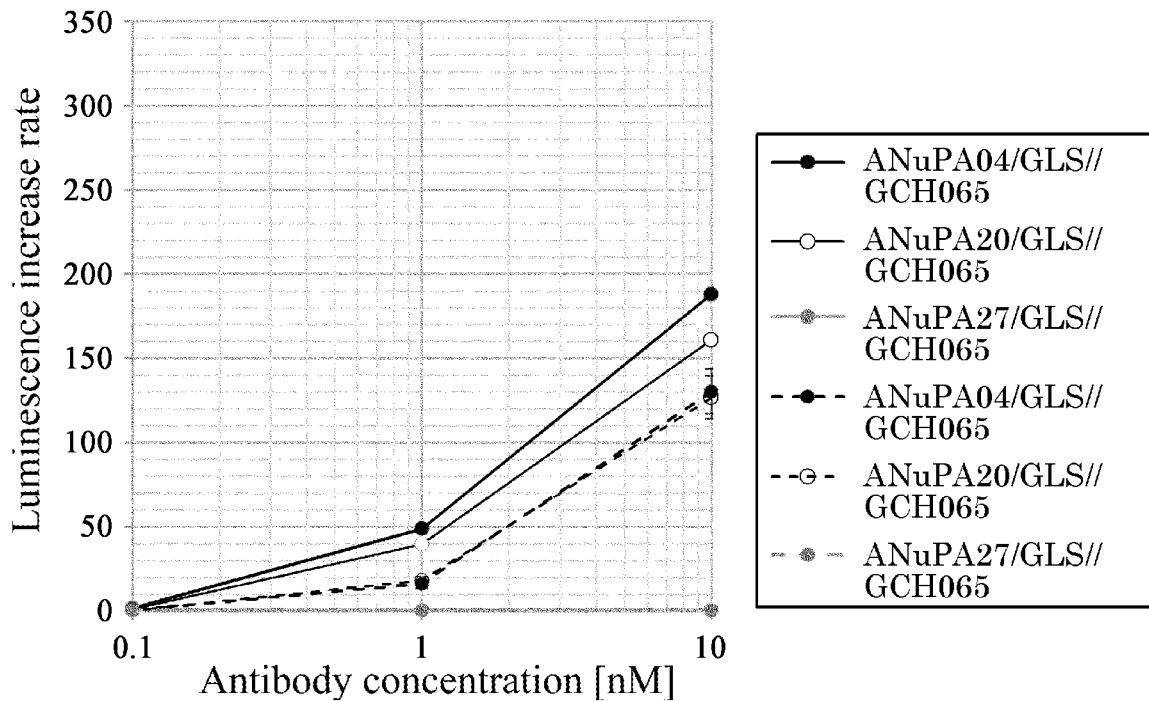
Figures 1, 13:
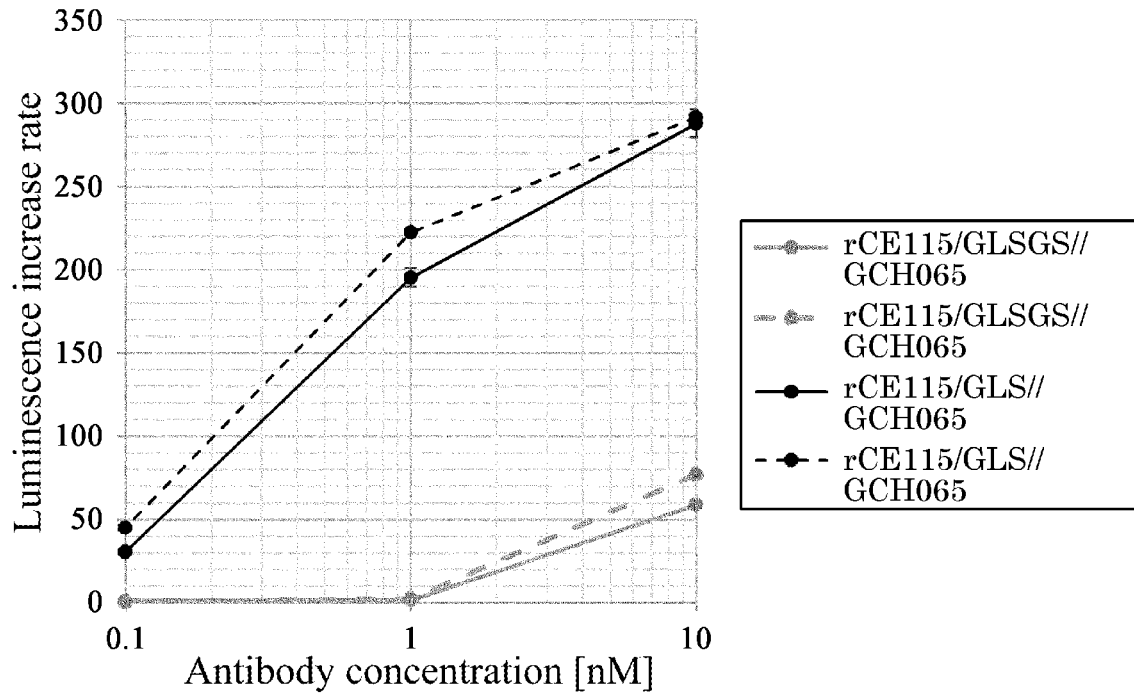
Figures 2, 13:
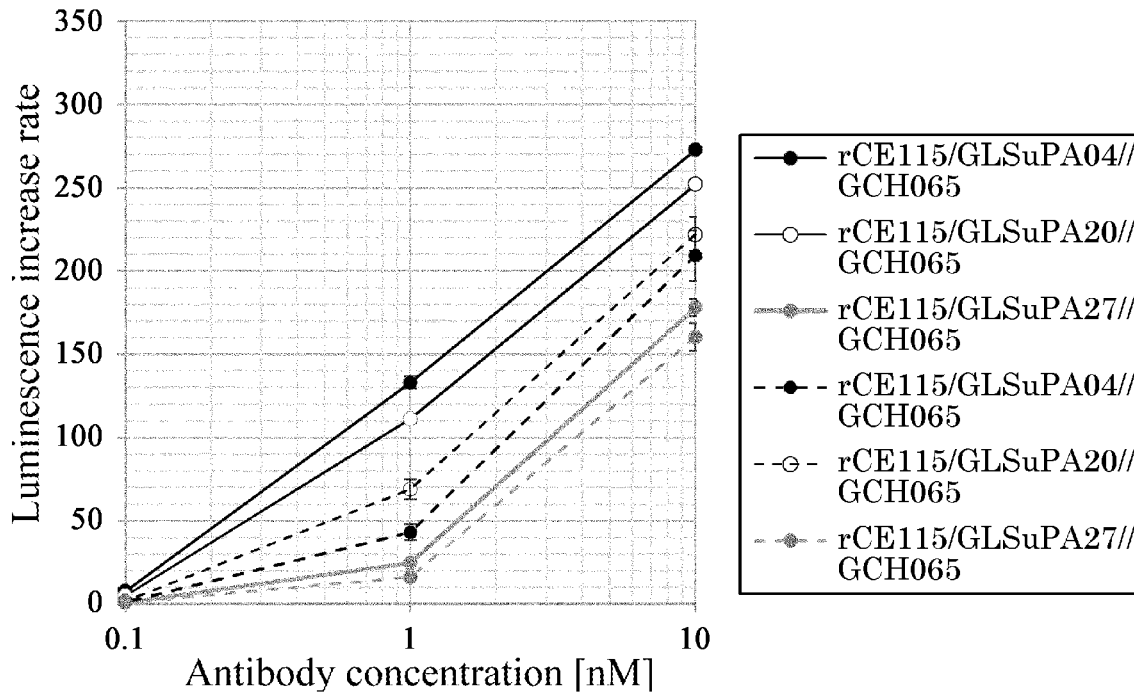
Figures 1, 14:
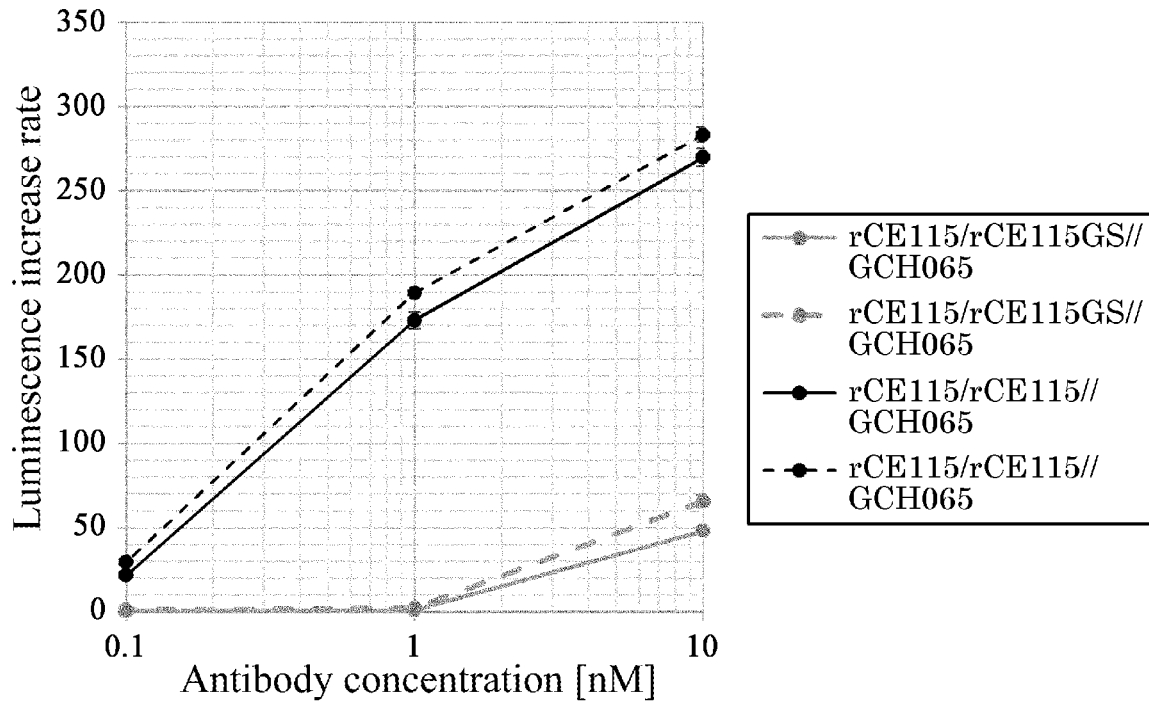
Figures 2, 14:
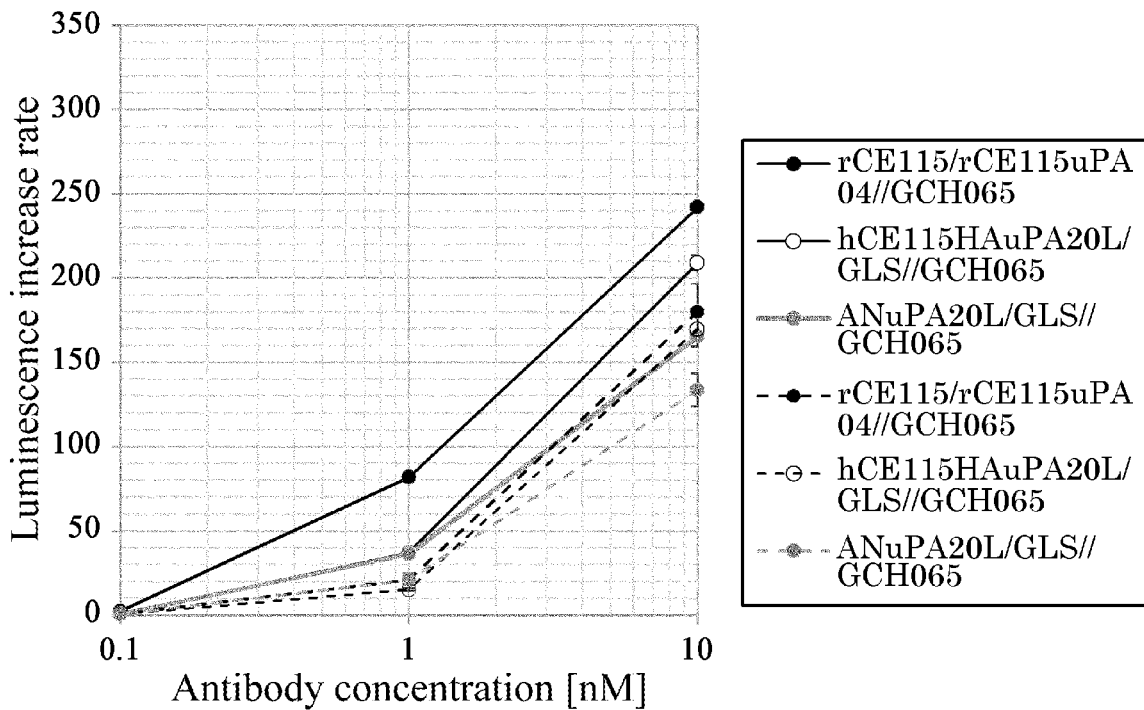
Figures 1, 15:
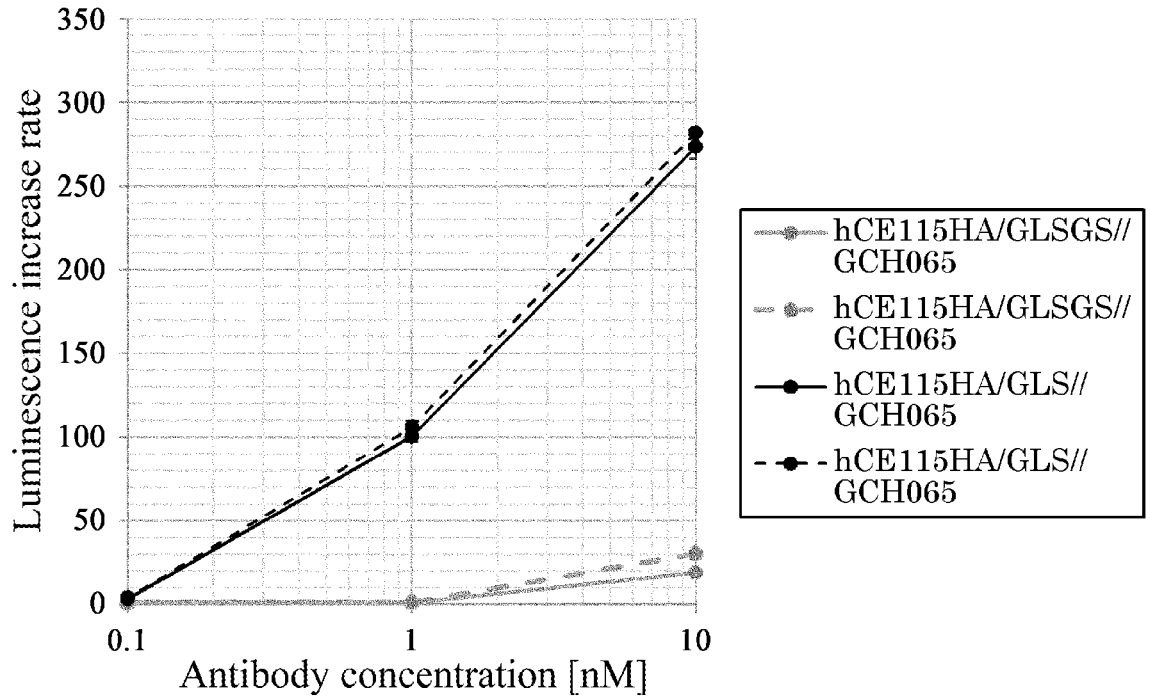
Figures 2, 15:
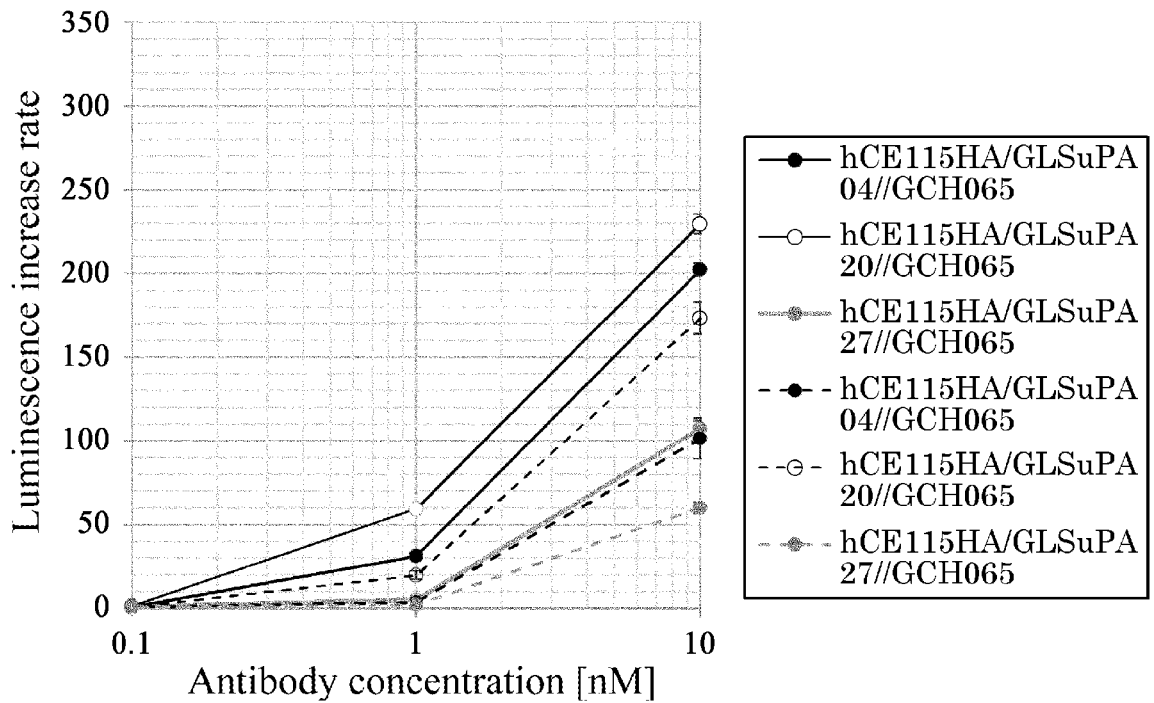

The structure and electron density map near the epitope in the complex formed by the anti-CD3 antibody Fab fragment and the epitope peptide based on the obtained crystal structure are shown in FIG. 5. The electron density was sufficiently observed only from the N terminus to the fifth residue Glu of the epitope peptide; therefore, a model could not be constructed for the sequence from the sixth residue of the epitope peptide and beyond. Thus, this antibody was found to bind to CD3 by mainly recognizing the peptide sequence from the N terminus to the fifth residue of CD3 (epitope core sequence), at the pocket formed between the heavy and light chains of the Fab fragment (see the arrow in FIG. 1).

Since the epitope core sequence on CD3 for the above-mentioned antibody could be identified in this manner, an appropriate linker length for linking this epitope core sequence with the anti-CD3 antibody heavy chain N terminus and an appropriate linker length for linking this epitope core sequence with the anti-CD3 antibody light chain N terminus were estimated using the MOE program (Chemical Computing Group Inc.).

First, based on the obtained crystal structure of the complex of the Fab fragment and the epitope peptide, two models were produced: one model in which Gly was added to each of the heavy chain N terminus and the C terminus of the fifth residue Glu of the epitope peptide; and the other model in which Gly was added to each of the light chain N terminus and the C terminus of the fifth residue Glu of the epitope peptide.

Next, to search for Gly linkers for linking the added Gly residues to each other, hydrogen atoms were added to both models using the protonate 3D function, AMBER10: EHT was used as the force field, solvation R-field was specified for solvation, and linker modeler function was used for sampling from the Protein Data Bank database using lengths of 1 to 60 residues as the searching range.

As a result, when linking the epitope core sequence and the anti-CD3 antibody heavy-chain N terminus using a linker, the minimum length for the linkage was suggested to be a six-amino-acid linker (FIG. 6A). However, a linker consisting of six amino acid residues follows a path that nearly contacts the antibody surface, and when linkage is attempted by using for example a linker containing amino acids other than Gly, steric hindrance with the antibody is expected to occur. On the other hand, as shown in FIGS. 6B, 6C, and 6D, when a linker consisting of 9, 12, or 16 amino acids is used for the linkage, some room is formed between the linker and the antibody surface, and it is expected that even a linker containing residues other than Gly would be used for the linkage.

Similarly, when linking the epitope core sequence and the anti-CD3 antibody light-chain N terminus using a linker, the minimum length for the linkage was suggested to be an eleven-amino-acid linker (FIG. 7A). However, a linker consisting of eleven amino acid residues follows a path that nearly contacts the antibody surface, and when linkage is attempted by using for example a linker containing amino acids other than Gly, steric hindrance with the antibody is expected to occur. On the other hand, as shown in FIGS. 7B, 7C, and 7D, when a linker consisting of 12, 14, or 16 amino acids is used for the linkage, some room is formed between the linker and the antibody surface, and it is expected that a linker containing residues other than Gly would be used for the linkage.

From the above results, when linking the epitope sequence and the anti-CD3 antibody heavy-chain N terminus (top panel of FIG. 3), the appropriate amino acid lengths of the cancer tissue-specific protease-cleavable linker (β) and the masking molecule (γ) were estimated to be 11 amino acids or more to 65 amino acids or less, more preferably 14 to 27 amino acids, and even more preferably 17 to 20 amino acids.

Furthermore, when linking the epitope sequence and the anti-CD3 antibody light-chain N terminus (bottom panel of FIG. 3), the appropriate amino acid lengths of the cancer tissue-specific protease-cleavable linker (β) and the masking molecule (γ) were estimated to be 16 amino acids or more to 65 amino acids or less, more preferably 17 to 30 amino acids, and even more preferably 19 to 25 amino acids.

Example 3: Preparation of an Anti-CD3 Antibody Derivative in which Binding to CD36 is Masked As indicated in Table 1 shown below, anti-CD3 antibody derivatives in which a masking molecule (γ) and a cancer tissue-specific protease-cleavable linker (β) have been fused to the heavy chain N terminus of the humanized anti-CD3 antibody prepared in Reference Example 1 are prepared. The cancer tissue-specific protease-cleavable linkers (β) used in Table 1 have a sequence targeted by MMP-2 (WO2010/081173 and WO2009/025846), and are peptides that have different lengths. The targeted sequence is known to be cleaved by MMP-9 as well (Integr Biol (Camb). 2009 June; 1(5-6): 371-381).

TABLE 1

| Antibody Name | Masking molecule (γ) | Cancer tissue-specific protease cleavable linker (β) | Antibody variable region + constant region | Full-length heavy chain sequence | Full-length light chain sequence |
|---|---|---|---|---|---|
| CD3H1 | SEQ ID NO: 15 | SEQ ID NO: 16 | SEQ ID NO: 20 | SEQ ID NO: 21 | SEQ ID NO: 25 |
| CD3H2 | SEQ ID NO: 15 | SEQ ID NO: 17 | SEQ ID NO: 20 | SEQ ID NO: 22 | SEQ ID NO: 25 |
| CD3H3 | SEQ ID NO: 15 | SEQ ID NO: 18 | SEQ ID NO: 20 | SEQ ID NO: 23 | SEQ ID NO: 25 |
| CD3H4 | SEQ ID NO: 15 | SEQ ID NO: 19 | SEQ ID NO: 20 | SEQ ID NO: 24 | SEQ ID NO: 25 |

Moreover, as indicated in Table 2, anti-CD3 antibody derivatives in which a masking molecule (γ) and a cancer tissue-specific protease-cleavable linker (β) have been fused to the light chain N terminus of the humanized anti-CD3 antibody prepared in Reference Example 1 are prepared. As in Table 1, the cancer tissue-specific protease-cleavable linkers (0) used in the table have a sequence targeted by MMP-2 (WO2010/081173 and WO2009/025846), and are peptides that have different lengths. The targeted sequence is known to be cleaved by MMP-9 as well (Integr. Biol. (Camb.) 2009 June; 1 (5-6): 371-381).

TABLE 2

| Antibody Name | Masking molecule (γ) | Cancer tissue-specific protease cleavable linker (β) | Antibody variable region + constant region | Full-length light chain sequence | Full-length heavy chain sequence |
|---|---|---|---|---|---|
| CD3L1 | SEQ ID NO: 15 | SEQ ID NO: 26 | SEQ ID NO: 29 | SEQ ID NO: 30 | SEQ ID NO: 34 |
| CD3L2 | SEQ ID NO: 15 | SEQ ID NO: 27 | SEQ ID NO: 29 | SEQ ID NO: 31 | SEQ ID NO: 34 |
| CD3L3 | SEQ ID NO: 15 | SEQ ID NO: 28 | SEQ ID NO: 29 | SEQ ID NO: 32 | SEQ ID NO: 34 |
| CD3L4 | SEQ ID NO: 15 | SEQ ID NO: 19 | SEQ ID NO: 29 | SEQ ID NO: 33 | SEQ ID NO: 34 |

CD3H1, CD3H2, CD3H3, and CD3H4 of Table 1 and CD3L1, CD3L2, CD3L3, and CD3L4 of Table 2 are prepared by known antibody production methods using the respective plasmid encoding the heavy chain full-length sequence and expression vector carrying the light chain full-length sequence.

Example 4: Assessment of Binding Between CD3 and the Anti-CD3 Antibody

An anti-CD3 antibody was prepared according to the method of Reference Example 2. Specifically, first, an animal cell expression vector for expression of a polypeptide in which the heavy chain variable region (SEQ ID NO: 10) and pE22Hh (SEQ ID NO: 35) have been fused, an animal cell expression vector for expression of a polypeptide in which the light chain variable region (SEQ ID NO: 11) and Kappa chain (SEQ ID NO: 36) have been fused, and an animal cell expression vector for expression of the heavy chain constant region ranging from the hinge portion to the C-terminal side (Kn0101G3 (SEQ ID NO: 37)), were used to coexpress these polypeptides in cells to produce an anti-CD3 antibody as a One-arm antibody. Then, the anti-CD3 antibody was purified from the culture supernatant.

Assessment of binding between the anti-CD3 antibody and human CD3 was performed using BiacoreT200. Specifically, biotinylated CD3 peptide was bound to a CM4 chip via streptavidin, the prepared antibody was flushed as the analyte, and the binding affinity was analyzed at 37° C.

The results of evaluation of binding are shown in Table 3 below.

TABLE 3

| sample | ka (1/Ms) | kd (1/s) | KD (M) |
|---|---|---|---|
| Anti-CD3 antibody | 1.09E+05 | 4.19E−02 | 3.83E−07 |

Reference Example 3: Selection of Anti-CD3 Antibody Derivatives Having Enhanced Binding to CD3ε

Reference Example 3-1. Method for Enhancing CD3 Binding

A possible method using the anti-CD3 antibody-derived antibody library (Dual Fab Library) described in WO2015/068847 is a method for obtaining an antibody having increased binding to CD3. General examples of affinity maturation include a method which involves altering an amino acid in an obtained antibody sequence by site-directed mutagenesis and measuring affinity, and methods using in vitro display methods including phage display. In the in vitro display methods, plural types of antibody sequences mutated from an obtained sequence by error prone PCR or the like are used as a library to select a sequence having strong affinity.

Use of a dual-Fab library containing selected amino acids that maintain 80% or more of the CD3 binding of a conventional anti-CD3 antibody (e.g., a CD3-binding antibody having the template sequence mentioned above) may allow the efficient finding of a sequence having strong binding to CD3.

Reference Example 3-2: Obtainment of Fab Domain Having Enhanced Binding to Human CD3

Fab domains (antibody fragments) binding to human CD3 were identified from the dual Fab library disclosed in WO2015/068847. Biotin-labeled CD3 was used as an antigen, and antibody fragments having the ability to bind to human CD3 were enriched.

Phages were produced from the E. coli harboring the constructed phagemids for phage display. 2.5 M NaCl/10% PEG was added to the culture solution of the E. coli that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Pro& (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 ng/mL trypsin, the beads were suspended at room temperature for 15 minutes, immediately after which the beads were separated using a magnetic stand to recover a phage solution. The recovered phage solution was added to 10 mL of an E. coli strain ER2738 in a logarithmic growth phase (OD600: 0.4-0.5). The E. coli strain was infected by the phages through the gentle spinner culture of the strain at 37° C. for 1 hour. The infected E. coli was inoculated to a plate of 225 mm×225 mm. Next, phages were recovered from the culture solution of the inoculated E. coli to prepare a phage library solution. This cycle, called panning, was repeated 7 times in total. In the second and subsequent rounds of panning, 40, 10, 10, 1, 1, and 0.1 pmol of the human CD3 were respectively used. In the fifth and subsequent rounds, a 1000-fold amount of a human CD3ε homodimer was added each time the human CD3 was added.

Reference Example 3-3: Preparation of IgG Having the Obtained Fab Domain

The population of antibody fragments having the ability to bind to CD3 obtained in Reference Example 3-2 is constituted by only Fab domains. Thus, these Fab domains were converted to IgG type (conjugate of Fab and Fc). The VH fragment was amplified from E. coli, each having an antibody fragment having the ability to bind to CD3, by PCR using primers specifically binding to the H chain in the dual Fab library. Using the method of Reference Example 2, the amplified VH fragment was integrated into a plasmid, which allows expression in animal cells and, into which F760mnP17 (SEQ ID NO: 39) had been incorporated. Specifically, AN121H-F760mnP17 (SEQ ID NO: 40) was used as an H chain, and a sequence (SEQ ID NO: 25) made by linking GLS3000 (SEQ ID NO: 13) to the kappa sequence (SEQ ID NO: 36) was used as an L chain. These sequences were expressed and purified according to Reference Example 1. This antibody was called AN121.

Example 5: Evaluation of Binding to CD3δ Heterodimer

Binding of antibodies prepared in the Reference Examples to a CD3εδ heterodimer was evaluated by the surface plasmon method (SPR method).

5-1. Preparation of a CD3εδ Heterodimer

A CD3εδ heterodimer was prepared by the following method. First, to the 3' end of a gene encoding the extracellular domain of CD3ε, a gene encoding a Factor Xa cleavage site and a gene encoding the amino acids on the C-terminal side from the hinge region of a human immunoglobulin (IgG1) in which position 349 is Cys and position 366 is Trp (EU numbering) were fused, and additionally a gene encoding a TEV protease cleavage site and a BAP tag sequence was fused to produce a gene (a gene encoding SEQ ID NO: 41). The obtained gene was inserted into an animal cell expression vector. Next, to the 3' end of a gene encoding the extracellular domain of CD3δ, a gene encoding a Factor Xa cleavage site and a gene encoding the C-terminal side from the hinge region of a human immunoglobulin (IgG1) in which position 356 is Cys, position 366 is Ser, position 368 is Ala, and position 407 is Val (EU numbering) were fused, and additionally a gene encoding a Flag tag sequence was fused to produce a gene (a gene encoding SEQ ID NO: 42). The obtained gene was inserted into an animal cell expression vector. As in Reference Example 2, the animal cell expression vector carrying the gene encoding SEQ ID NO: 41 and the animal cell expression vector carrying the gene encoding SEQ ID NO: 42 were introduced into FreeStyle 293 cells (Invitrogen). After the introduction, the cells were shake cultured at 37° C. according to a protocol, and the supernatant was collected five days later. The CD3εδ heterodimer to which an antibody constant region (particularly Fc) had been fused was obtained from the supernatant using a Protein A column (Eshmuno A (Merck)). To further obtain the heterodimer, the CD3εδ heterodimer to which an antibody constant region had been fused was fractionated using an Anti-FLAG M2 column (Sigma). Then, gel filtration chromatography (Superdex200, GE Healthcare) was performed to fractionate and collect the desired CD3εδ heterodimer.

Factor Xa (NEB) was added to the collected CD3εδ, to which the antibody constant region had been fused, to separate the CD3εδ heterodimer and the antibody constant region. Protease removal was carried out by passage through a Benzamidine column (GE Healthcare), and the desired CD3εδ heterodimer was obtained using a Mabselect Sure column (GE Healthcare), ion exchange chromatography (Q sepharose HP, GE Healthcare), and gel filtration chromatography (Superdex 200, GE Healthcare).

5-2. Measurement of Binding to the CD3εδ Heterodimer

The activity of binding to the CD3δ heterodimer was measured for: the rat anti-CD3 antibody containing as the variable region the heavy chain variable region (SEQ ID NO: 10) and the light chain variable region (SEQ ID NO: 11) described in Reference Example 1; a combination of a human anti-CD3 antibody and a rat anti-CD3 antibody which contains as the variable region a heavy chain variable region (SEQ ID NO: 12) and a light chain variable region (SEQ ID NO: 13) where the light chain has been humanized by a method known to those skilled in the art; a humanized anti-CD3 antibody which contains as the variable region a heavy chain variable region (SEQ ID NO: 12) and a light chain variable region (SEQ ID NO: 13), which have been humanized by a method known to those skilled in the art; and AN121 which contains as the variable region a heavy chain variable region (SEQ ID NO: 43) and a light chain variable region (SEQ ID NO: 13). The heavy chain variable regions were fused with F760mnP17 (SEQ ID NO: 39) used as the constant region and the light chain variable regions were fused with the Kappa chain (SEQ ID NO: 36) used as the constant region, and the antibodies were expressed according to the method of Reference Example 2.

The activity of binding to the CD3εδ heterodimer was assessed using BiacoreT200. Specifically, Protein G was immobilized onto a CM3 chip by a method known to those skilled in the art, and antibodies to be evaluated were bound to the immobilized Protein G. Then, the CD3εδ heterodimer prepared at 4000, 1000, 250, 62.5, 15.6, and 3.9 nM was bound thereto, and the binding was evaluated using the single cycle kinetics mode. Measurements were taken under conditions of 20 mM ACES, 150 mM NaCl, and pH7.4 at 37° C. The results are shown in Table 4.

TABLE 4

| Antibody Name | Heavy chain SEQ ID NO | Light chain SEQ ID NO | ka (1/Ms) | kd (1/s) | KD (M) |
|---|---|---|---|---|---|
| CE115VH-F760mnP17/rCE115VL-k0 (Rat anti-CD3 antibody) | 44 | 45 | 4.04E+04 | 7.71E−03 | 1.91E−07 |
| Combination of rat anti-CD3 antibody and human anti-CD3 antibody) (CE115VH-F760mnP17/GLS3000-k0) | 44 | 25 | 4.73E+04 | 1.24E−02 | 2.62E−07 |
| CE115HA000-F760mnP17/GLS3000-k0 (Humanized anti-CD3 antibody) | 46 | 25 | 5.18E+04 | 2.88E−02 | 5.56E−07 |
| AN121H-F760mnP17/GLS3000-k0 (AN121) | 40 | 25 | 7.47E+04 | 7.23E−04 | 9.68E−09 |

As shown in Table 4, AN121 obtained in Reference Example 3 was shown to have enhanced binding to CD3εδ.

Example 6: Preparation of Anti-CD3 Antibody Derivatives with Masked Binding to CD3ε and Noncleavable Antibodies Anti-CD3 antibody derivatives in which the binding to CD3ε was masked by the addition of a masking molecule (γ) via a cancer tissue-specific protease-cleavable linker (β), and anti-CD3 antibody derivatives to which the masking molecule (γ) was attached using a noncleavable linker that does not carry the cancer tissue-specific protease-cleavable linker (β) (shown in Table 5) were prepared according to the method of Reference Example 2. The sequence reported in WO2013/163631 (LSGRSDNH; SEQ ID NO: 47) was used as the cancer tissue-specific protease-cleavable linker (β). Sequences in which a sequence cleaved by MMP-2 indicated in Example 3 (PLGLAG; SEQ ID NO: 106) or a linker peptide composed of Gly and Ser is inserted at the site of the cancer tissue-specific protease-cleavable linker (β) were also prepared as controls. Specifically, firstly, an animal cell expression vector for expression of a polypeptide in which a heavy chain variable region and pE22Hh (SEQ ID NO: 35) are fused, an animal cell expression vector for expression of a polypeptide in which a light chain variable region and the Kappa chain (SEQ ID NO: 36) are fused, and an animal cell expression vector for expression of the C-terminal side of the heavy chain constant region from the hinge portion (Kn010 (SEQ ID NO: 48)) were used to coexpress these polypeptides in cells to produce an anti-CD3 antibody as a One-arm antibody. Next, the anti-CD3 antibody was purified from the culture supernatant. Alternatively, F760mnP17 (SEQ ID NO: 39) was linked as the heavy chain constant region to the heavy chain variable region, and this was expressed together with the full-length light chain to produce an anti-CD3 antibody as a TWO arm antibody, and the anti-CD3 antibody was purified from the culture supernatant. IDC-30 T2

TABLE 5

| Antibody Name | Modification at the heavy chain N-terminus Masking molecule | Protease-cleavable linker | Heavy chain variable region | Heavy chain constant region | Full-length heavy chain | Full-length light chain | Second heavy chain |
|---|---|---|---|---|---|---|---|
| hCE115HA/GLS One arm | None | None | 12 | 35 | 34 | 25 | 48 |
| hCE115HAGS/GLS One arm | 15 | 52 | 58 | 35 | 82 | 25 | 48 |
| hCE115HAuPA04/GLS One arm | 49 | 53 | 60 | 35 | 83 | 25 | 48 |
| hCE115HAuPA20/GLS One arm | 50 | 54 | 61 | 35 | 84 | 25 | 48 |
| hCE115HAuPA20L/GLS One arm | 50 | 59 | 62 | 35 | 85 | 25 | 48 |
| hCE115HAuPA27/GLS One arm | 51 | 47 | 63 | 35 | 86 | 25 | 48 |
| hCE115HAMMP02/GLS One arm | 15 | 55 | 64 | 35 | 87 | 25 | 48 |

| Antibody Name | Modification at the heavy chain N-terminus Masking molecule | Protease-cleavable linker | Light chain variable region | Light chain constant region | Full-length light chain | Full-length heavy chain | Second heavy chain |
|---|---|---|---|---|---|---|---|
| hCE115HA/GLS One arm | None | None | 13 | 36 | 25 | 34 | 48 |
| hCE115HA/GLSGS One arm | 15 | 56 | 65 | 36 | 88 | 34 | 48 |
| hCE115HA/GLSuPA02 One arm | 15 | 54 | 66 | 36 | 89 | 34 | 48 |
| hCE115HA/GLSuPA04 One arm | 49 | 53 | 67 | 36 | 90 | 34 | 48 |
| hCE115HA/GLSuPA20L One arm | 50 | 59 | 68 | 36 | 91 | 34 | 48 |
| hCE115HA/GLSSuPA27 One arm | 51 | 47 | 69 | 36 | 92 | 34 | 48 |
| hCE115HA/GLSMMP02 One arm | 15 | 55 | 70 | 36 | 93 | 34 | 48 |
| hCE115HA/GLS Two arm | None | None | 13 | 36 | 25 | 46 | None |
| hCE115HA/GLSGS Two arm | 15 | 56 | 71 | 36 | 94 | | None |
| hCE115HA/GLSuPA20 Two arm | 50 | 54 | 72 | 36 | 95 | | None |
| hCE115HA/GLSMMP02 Two arm | 15 | 55 | 73 | 36 | 96 | | None |

| Antibody Name | Modification at the heavy chain N-terminus Masking molecule | Protease-cleavable linker | Heavy chain variable region | Heavy chain constant region | Full-length heavy chain | Full-length light chain | Second heavy chain |
|---|---|---|---|---|---|---|---|
| AN/GLS One arm | None | None | 43 | 35 | 97 | 25 | 48 |
| ANGS/GLS One arm | 15 | 52 | 74 | 35 | 98 | 25 | 48 |
| ANuPA02/GLS One arm | 15 | 57 | 75 | 35 | 99 | 25 | 48 |
| ANuPA04/GLS One arm | 49 | 53 | 76 | 35 | 100 | 25 | 48 |
| ANuPA20/GLS One arm | 50 | 54 | 77 | 35 | 101 | 25 | 48 |
| ANuPA20L/GLS One arm | 50 | 59 | 78 | 35 | 102 | 25 | 48 |
| ANuPA27/GLS One arm | 51 | 47 | 79 | 35 | 103 | 25 | 48 |
| ANuPA27L/GLS One arm | 51 | 130 | 80 | 35 | 104 | 25 | 48 |
| ANMMP02/GLS One arm | 15 | 55 | 81 | 35 | 105 | 25 | 48 |

| Antibody Name | Modification at the heavy chain N-terminus Masking molecule | Protease-cleavable linker | Heavy chain variable region | Heavy chain constant region | Full-length heavy chain | Full-length light chain | Second heavy chain |
|---|---|---|---|---|---|---|---|
| hCE115HA-CD3/GLS One arm | 107 | 47 | 12 | 35 | 108 | 25 | 48 |
| hCE115HA-CD3/GLS One arm | 107 | 59 | 12 | 35 | 109 | 25 | 48 |

TABLE 5-continued

| | Modification at the heavy chain N-terminus | | Light chain | Light chain | | | Second |
|---|---|---|---|---|---|---|---|
| | | | SEQ ID NO | | | | |
| Antibody Name | Masking molecule | Protease-cleavable linker | variable region | constant region | Full-length light chain | Full-length heavy chain | heavy chain |
| hCE115HA/GLS-CD3 One arm | 107 | 47 | 13 | 36 | 110 | 34 | 48 |
| hCE115HA/GLS-CD3 Linker One arm | 107 | 59 | 13 | 36 | 111 | 34 | 48 |

Table 6 shows the antibody concentrations. When the extracellular domain of CD3ε was fused, the concentration after purification was decreased compared to the other variants, and this suggested that the expression level is low.

TABLE 6

| Antibody name | Concentration (mg/mL) |
|---|---|
| hCE115HA/GLS One arm | 0.808 |
| hCE115HAGS/GLS One arm | 1.580 |
| hCE115HA/GLSGS One arm | 0.756 |
| hCE115HA-CD3/GLS One arm | 0.379 |
| hCE115HA-CD3_Linker/GLS One arm | 0.441 |
| hCE115HA/GLS-CD3 One arm | 0.048 |
| hCE115HA/GLS-CD3_Linker One arm | 0.056 |

Example 7: Evaluation of CD3ε Binding Activity of Protease-Treated Anti-CD3 Antibody Derivatives with Masked Binding to CD3ε and of Noncleavable Antibodies The antibodies prepared in Example 6 were subjected to protease treatment, and whether the anti-CD3 antibody derivatives with masked binding to CD3ε bind to CD3ε was assessed. The antibodies were obtained by the method shown in Reference Example 2, uPA (Recombinant Human u-Plasminogen Activator, R&D systems) was added at a final concentration of 25 nM to 5 μg of the obtained antibodies, and the mixture was reacted in PBS at 37° C. for 16 hours to 20 hours.

The CD3ε extracellular domain (CD3ε homodimer) was biotinylated using No-Weigh Premeasured NHS-PEO4-Biotin Microtubes (Pierce) according to the protocol. A blocking buffer (0.5× Block ACE containing 0.02% Tween20 and 0.05% ProClin300) was used to dilute the antigens, beads, and antibodies. The biotinylated antigens and paramagnetic beads (Dynabeads (registered trademark) MyOne™ Streptavidin T1, Invitrogen) were nixed and allowed to stand at room temperature for ten minutes. At the same time, paramagnetic beads and blocking buffer were added to wells with no addition of antigens. The antibody solution treated or untreated with the protease was diluted to 4 μg/mL, 1 μg/mL, 0.25 μg/mL, 0.0625 μg/ml, 0.015625 μg/mL, and 0 μg/mL using PBS, and each of them was added in 25-μL aliquots. For the AN121 variant, 1 μg/mL was used as the highest dose. The beads and antibodies were mixed well, and then left to stand at room temperature for 30 minutes. After washing once with TBS (TaKaRa) containing 0.05% Tween20 (Nacalai), HRP-labeled anti-Kappa chain antibody (Anti-Human Kappa Chain antibody, Abcam, ab79115) diluted 16000-times was added and the resulting mixture was allowed to stand at room temperature for another ten minutes. The mixture was washed again three times, and Lumi-Phos-HRP (Lucmigen, PAA457009) was added thereto as a substrate. After allowing the mixture to stand at room temperature for two minutes, luminescence was detected on Synergy HTX. The detected luminescence values were presented as ratios to the values for the respective wells containing the same concentration of the antibody and no antigen. The results are shown in FIG. 8. As shown in FIG. 8, antibodies that do not contain a cancer tissue-specific protease-cleavable linker (β) did not show any variation in binding activity between the case where the protease was added (protease-treated) and the case where the protease was not added (protease-untreated). In contrast, antibodies containing a cancer tissue-specific protease-cleavable linker (β) showed a remarkable increase in the binding to CD3ε by the protease treatment. Specifically, when a cancer tissue-specific protease-cleavable linker (β) was connected to the heavy chain, as indicated by hCE115HAuPA04, the change in binding activity before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus via the GGGS (SEQ ID NO:1) peptide sequence. On the other hand, when the masking molecule (γ) was composed of 20 amino acids (hCE115HAuPA20) or 27 amino acids (hCE115HAuPA27), the binding activity increase rate due to the protease treatment was decreased as compared to that obtained using the masking molecule (γ) composed of seven amino acids (hCE115HAuPA04). The result of linking a masking molecule (γ) and a cancer tissue-specific protease-cleavable linker (β) to the AN121 heavy chain is shown in (iv) of FIG. 8, and indicates that, similarly to the results indicated for hCE115HA, cleavage by the protease increased CD3 binding activity. Regarding AN121 as well, the short masking molecule (γ) was shown to be more preferable to the masking molecule (γ) composed of 20 amino acids (ANuPA20) or 27 amino acids (ANuPA27). Similarly, when a cancer tissue-specific protease-cleavable linker (3) was connected to the light chain, as shown by GLSuPA04, the change in the binding activity before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus via the GGGS (SEQ ID NO:1) peptide sequence. On the other hand, when the masking molecule (γ) was composed of 20 amino acids (GLSuPA20) or 27 amino acids (GLSuPA27), the binding activity increase rate due to the protease treatment was decreased as compared that obtained using the masking molecule (γ) composed of seven amino acids (GLSuPA04).

This examination revealed that a naturally-occurring sequence can be used as the masking molecule (γ), and it was shown that molecules exhibiting desired effects can be prepared by changing the length of the masking molecule (γ) in line with a naturally-occurring sequence as in the method indicated in the present Example so that the masking molecule (γ) will have an appropriate length and by changing the length of the cancer tissue-specific protease-cleavable linker (β).

Example 8: Evaluation of CD3ε-Binding Activity of Protease-Treated Anti-CD3 Antibody Derivatives with Masked Binding to CD3ε and of Noncleavable Antibodies In Example 7, sequences were cleaved using uPA, but it is known that the sequences can also be cleaved by matriptase. Accordingly, whether the samples prepared in Example 7 were also cleaved by matriptase and bound to CD3 was assessed. Antibodies were prepared by the method of Example 7, and then human MT-SP1 (Matriptase/ST14 Catalytic Domain, R&D systems) was added at a final concentration of 50 nM to 3 μg of each of the antibodies. After addition, the respective mixture was incubated at 37° C. for 22 hours, and then binding activities were assessed in the same manner as in Example 7. The results are shown in FIG. 9. As shown in FIG. 9, antibodies that do not contain a cancer tissue-specific protease-cleavable linker (β) did not show any variation in binding activity between the case where the protease was added (protease-treated) and the case where the protease was not added (protease-untreated). In contrast, antibodies containing a cancer tissue-specific protease-cleavable linker (β) showed a remarkable increase in the binding to CD3ε through by the protease treatment. Specifically, when a cancer tissue-specific protease-cleavable linker (β) was connected to the heavy chain, as indicated by hCE115HAuPA04, the change in binding activity before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus by the GGGS (SEQ ID NO:1) peptide sequence. On the other hand, when the masking molecule (γ) was composed of 20 amino acids (hCE115HAuPA20) or 27 amino acids (hCE115HAuPA27), the binding activity increase rate due to the protease treatment was decreased as compared to that obtained using the masking molecule (γ) composed of seven amino acids (hCE115HAuPA04). Similarly, when a cancer tissue-specific protease-cleavable linker (β) was connected to the light chain, as shown by GLSuPA04, the change in the binding activity before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus by the GGGS (SEQ ID NO:1) peptide sequence. On the other hand, when the masking molecule (γ) was composed of 20 amino acids (GLSuPA20) or 27 amino acids (GLSuPA27), the binding activity increase rate due to the protease treatment was decreased as compared to that obtained using the masking molecule (γ) composed of seven amino acids (GLSuPA04). This result was similar to the result shown in Example 7, indicating that the protease used to carry out the cleavage is not limited to uPA and may be other proteases.

Example 9: Evaluation of CD3ε Binding Activity of Protease-Treated Anti-CD3 Antibody Derivatives with Masked Binding to CD3ε and of Noncleavable Antibodies In Examples 7 and 8, a sequence (LSGRSDNH; SEQ ID NO: 47) reported in WO2013/163631 was used and cleavage was carried out using uPA or matriptase (MT-SP1). Next, whether the binding activity is increased by protease treatment, as in the case with uPA and MT-SP1, when using a sequence cleaved by MMP-2 as shown in Example 3, was examined. Antibodies were prepared by a method similar to that of Example 7.

MMP-2 (R&D systems) was preliminarily activated by adding a 100-mM solution of 4-aminophenylmercuric acetate (APMA, SIGMA) in dimethylsulfoxide (DMSO, Junsei Chemical Co., Ltd.) to MMP-2 at 1/100 equivalents (by volume), and then incubating the mixture at 37° C. for two hours. Activated MMP-2 was added at a final concentration of 50 nM to 3 μg of each of the antibodies, and the respective mixture was reacted at 37° C. for 22 hours. During incubation, the mixture was adjusted so that TBS (TaKaRa) supplemented with 0.1% Tween20 and 10 mM $CaCl_2$ accounts for half of the overall volume. After incubation, binding was evaluated by the electrochemical luminescence (ECL) method. The human CD3ε homodimer protein to which biotin had been added (18 pmol/mL or 0 pmol/mL), the antibody solutions prepared at 1 μg/mL, 0.25 μg/mL, 0.0625 μg/mL, 0.015625 μg/mL, or 0 μg/mL, and anti-human Kappa chain antibody labeled with sulfo-tag (Ru complex) (SouthernBiotech, 2.7 μg/mL) were added to each well of Nunc-Immuno™ MicroWell™ 96 well round plates (Nunc) in 25-μL aliquots, and after mixing, the plates were incubated at room temperature for one hour or more to form antibody-antigen complexes. TBST containing 0.5% BSA (TBS (TaKaRa) solution containing 0.1% Tween20), referred to as the blocking solution, was added at 150 μL aliquots to each well of a streptavidin plate (MSD), and the plate was incubated at room temperature for two hours or more. The blocking solution was removed, and then the plate was washed three times with 250 μL of TBS(+) solution containing 0.1% Tween20. The antibody-antigen complex solution was added at 50-μL aliquots to each well, and the plate was shaken at 700 rpm at room temperature for one hour to bind the antibody-antigen complexes to the streptavidin plate. After removing the antibody-antigen complex solution, 2× READ buffer (MSD) was added at 150-μL aliquots to each well, and the luminescent signal from the sulfo-tag was detected using Sector Imager 2400 (MSD). The results are shown in FIG. 10.

As shown in FIG. 10, the antibodies that do not contain a cancer tissue-specific protease-cleavable linker (β) did not show any variation in binding activity between the case where the protease was added (protease-treated) and the case where the protease was not added (protease-untreated). In contrast, the antibody (hCE115HAMMP02) containing a cancer tissue-specific protease-cleavable linker (β) showed a remarkable increase in binding to CD3ε by the protease treatment. Even when a cancer tissue-specific protease-cleavable linker (β) was connected to the light chain, binding to CD3ε increased similarly. As described in Example 3, a longer linker may be used when connecting to a light chain; however, it was revealed that at least the use of the GGGGSPLSLAGGGS (SEQ ID NO: 55) sequence shown in the present Example exhibited the desired effects. The foregoing indicated that not only the cancer tissue-specific protease-cleavable linkers (β) indicated in Examples 7 and 8, but also the cancer tissue-specific protease-cleavable linkers (β) of Example 3 shown in the present Example can be used.

Example 10: Evaluation of CD3 Activation of Protease-Treated Anti-CD3 Antibody Derivatives with Masked Binding to CD3ε and of Noncleavable Antibodies In Examples 7 to 9, it was revealed that antibodies with masked binding to CD3δ showed a remarkable increase in binding to CD3ε by protease treatment. Next, whether activity of CD3 can be induced by protease treatment of antibodies was assessed. SK-pca-60 cells which correspond to SK-HEP1 cells that forcibly express GPC3 were used as target cells, and NFAT-RE-luc2-Jurkat cells (Promega) were used as effector cells. NFAT-RE-luc2-Jurkat cells (Promega) are derived from a human leukemia T-cell line, and are cells that have been modified to express luciferase in response to NFAT with CD3 activation. The anti-CD3 antibodies shown in Table 7 and GCH065-F760mnN17 (heavy chain SEQ ID NO: 112 and light chain SEQ ID NO: 113) were prepared according to the method of Reference Example 2. Furthermore, to prepare bispecific antibodies, the respective purified homodimers were used to prepare a desired bispecific antibody in which one of the Fab domains binds to GPC3 and the other Fab domain binds to CD3 in accordance with a method known to those skilled in the art (International Publication No. WO2015/046467). The bispecific antibody was written as XX/YY//ZZ, where XX indicates the anti-CD3 antibody heavy chain variable region, YY indicates the anti-CD3 antibody light chain variable region, and ZZ indicates the anti-GPC3 antibody. Then, protease treatment was carried out as in Example 7. For protease treatment, uPA (Recombinant Hunan u-Plasminogen Activator, R&D systems) was added at a final concentration of 25 nM to an antibody, and the mixture was reacted in PBS at 37° C. for twelve hours or more. Furthermore, antibodies not treated with protease were also incubated, similarly to the protease-treated antibody, at 37° C. for the same duration.

A 25-μL aliquot of the protease-treated antibody solution or protease-untreated antibody solution were added to 50 μL of a cell solution prepared by mixing NFAT-RE-luc2-Jurkat cells (Promega) ($7.5 \times 10^4$ cells per well) and SK-pca-60 cells ($1.25 \times 10^4$ cells per well) which correspond to SK-HEP1 cells forcibly expressing GPC3, and, 24 hours later, luciferase activity was measured using Bio-Glo Luciferase assay system (Promega, G7941). Luciferase activity was measured using 2104 EnVision (Perkin Elmer), the increase rate was calculated from the obtained luminescence value by defining the result from wells without antibody addition as 1, and the results are shown in FIGS. 11 to 15. Furthermore, the increase rates due to the protease treatment (value obtained by dividing the increase rate in the luminescence value of a protease-treated antibody by the increase rate in the luminescence value of a protease-untreated antibody) are shown in Table 8.

TABLE 7

| Antibody Name | Anti-CD3 antibody (cells only showing a number indicate a SEQ ID NO) | | | | |
|---|---|---|---|---|---|
| | Masking molecule added to the heavy chain | Protease-cleavable linker added to the heavy chain | Heavy chain variable region | Heavy chain variable region | Full-length heavy chain |
| hCE115HA/GLS//GCH065 | None | None | hCE115HA | 12 | 46 |
| hCE115HAGS/GLS//GCH065 | 15 | 52 | hCE115HA | 58 | 116 |
| hCE115HAuPA04/GLS//GCH065 | 49 | 53 | hCE115HA | 60 | 117 |
| hCE115HAuPA20/GLS//GCH065 | 50 | 54 | hCE115HA | 61 | 118 |
| hCE115HAuPA27/GLS//GCH065 | 51 | 47 | hCE115HA | 63 | 119 |
| hCE115HA/GLSGS//GCH065 | None | None | hCE115HA | 12 | 46 |
| hCE115HA/GLSuPA04//GCH065 | None | None | hCE115HA | 12 | 46 |
| hCE115HA/GLSuPA20//GCH065 | None | None | hCE115HA | 12 | 46 |
| hCE115HA/GLSuPA27//GCH065 | None | None | hCE115HA | 12 | 46 |
| AN/GLS//GCH065 | None | None | AN121H | 43 | 40 |
| ANGS/GLS//GCH065 | 15 | 52 | AN121H | 74 | 120 |
| ANuPA04/GLS//GCH065 | 49 | 53 | AN121H | 76 | 121 |
| ANuPA20/GLS//GCH065 | 50 | 54 | AN121H | 77 | 122 |
| ANuPA27/GLS//GCH065 | 51 | 47 | AN121H | 79 | 123 |
| rCE115/GLS//GCH065 | None | None | CE115VH | 10 | 44 |
| rCE115/GLSGS//GCH065 | None | None | CE115VH | 10 | 44 |
| rCE115/GLSuPA04//GCH065 | None | None | CE115VH | 10 | 44 |
| rCE115/GLSuPA20//GCH065 | None | None | CE115VH | 10 | 44 |
| rCE115/GLSuPA27//GCH065 | None | None | CE115VH | 10 | 44 |
| rCE115/rCE115GS//GCH065 | None | None | CE115VH | 10 | 44 |
| rCE115/rCE115//GCH065 | None | None | CE115VH | 10 | 44 |
| rCE115/rCE115uPA04//GCH065 | None | None | CE115VH | 10 | 44 |
| hCE115HAuPA20L/GLS//GCH065 | 50 | 59 | hCE115HA | 68 | 124 |
| ANuPA20L/GLS//GCH065 | 50 | 59 | AN121H | 78 | 125 |

| Antibody Name | Anti-CD3 antibody (cells only showing a number indicate a SEQ ID NO) | | | | |
|---|---|---|---|---|---|
| | Masking molecule added to the light chain | Protease-cleavable linker added to the light chain | Light chain variable region | Light chain variable region | Full-length light chain |
| hCE115HA/GLS//GCH065 | None | None | GLS3000 | 13 | 25 |
| hCE115HAGS/GLS//GCH065 | None | None | GLS3000 | 13 | 25 |

TABLE 7-continued

| | | | | | |
|---|---|---|---|---|---|
| hCE115HAuPA04/GLS//GCH065 | None | None | GLS3000 | 13 | 25 |
| hCE115HAuPA20/GLS//GCH065 | None | None | GLS3000 | 13 | 25 |
| hCE115HAuPA27/GLS//GCH065 | None | None | GLS3000 | 13 | 25 |
| hCE115HA/GLSGS//GCH065 | 15 | 56 | GLS3000 | 65 | 88 |
| hCE115HA/GLSuPA04//GCH065 | 49 | 53 | GLS3000 | 67 | 90 |
| hCE115HA/GLSuPA20//GCH065 | 50 | 54 | GLS3000 | 72 | 95 |
| hCE115HA/GLSuPA27//GCH065 | 51 | 47 | GLS3000 | 69 | 92 |
| AN/GLS//GCH065 | None | None | GLS3000 | 13 | 25 |
| ANGS/GLS//GCH065 | None | None | GLS3000 | 13 | 25 |
| ANuPA04/GLS//GCH065 | None | None | GLS3000 | 13 | 25 |
| ANuPA20/GLS//GCH065 | None | None | GLS3000 | 13 | 25 |
| ANuPA27/GLS//GCH065 | None | None | GLS3000 | 13 | 25 |
| rCE115/GLS//GCH065 | None | None | GLS3000 | 13 | 25 |
| rCE115/GLSGS//GCH065 | 15 | 56 | GLS3000 | 65 | 88 |
| rCE115/GLSuPA04//GCH065 | 49 | 53 | GLS3000 | 67 | 90 |
| rCE115/GLSuPA20//GCH065 | 50 | 54 | GLS3000 | 72 | 95 |
| rCE115/GLSuPA27//GCH065 | 51 | 47 | GLS3000 | 69 | 92 |
| rCE115/rCE115GS//GCH065 | 15 | 56 | CE115VL | 114 | 126 |
| rCE115/rCE115//GCH065 | None | None | CE115VL | 11 | 45 |
| rCE115/rCE115uPA04//GCH065 | 49 | 53 | CE115VL | 115 | 127 |
| hCE115HAuPA20L/GLS//GCH065 | None | None | GLS3000 | 13 | 25 |
| ANuPA201L/GLS//GCH065 | None | None | GLS3000 | 13 | 25 |

TABLE 8

| | Antibody concentration in assay (nM) | | |
|---|---|---|---|
| Antibody name | 1 | 0.1 | 0 |
| hCE115HA/GLS//GCH065 | 0.7 | 0.6 | 1.0 |
| hCE115HAGS/GLS//GCH065 | 1.0 | 1.0 | 1.0 |
| hCE115HAuPA04/GLS//GCH065 | 6.3 | 1.3 | 1.0 |
| hCE115HAuPA20/GLS//GCH065 | 2.4 | 1.1 | 1.0 |
| hCE115HAuPA27/GLS//GCH065 | 1.4 | 0.9 | 1.0 |
| AN/GLS//GCH065 | 0.7 | 0.6 | 1.0 |
| ANGS/GLS//GCH065 | 1.0 | 1.0 | 1.0 |
| ANuPA04/GLS//GCH065 | 3.0 | 1.9 | 1.0 |
| ANuPA20/GLS//GCH065 | 2.2 | 1.5 | 1.0 |
| ANuPA27/GLS//GCH065 | 0.9 | 0.9 | 1.0 |
| hCE115HA/GLS//GCH065 | 0.9 | 0.9 | 1.0 |
| hCE115HA/GLSGS//GCH065 | 0.9 | 1.0 | 1.0 |
| hCE115HA/GLSuPA04//GCH065 | 8.2 | 1.1 | 1.0 |
| hCE115HA/GLSuPA20//GCH065 | 3.0 | 1.6 | 1.0 |
| hCE115HA/GLSuPA27//GCH065 | 2.3 | 1.0 | 1.0 |
| rCE115/GLS//GCH065 | 0.9 | 0.7 | 1.0 |
| rCE115/GLSGS//GCH065 | 0.7 | 1.0 | 1.0 |
| rCE115/GLSuPA04//GCH065 | 3.1 | 6.4 | 1.0 |
| rCE115/GLSuPA20//GCH065 | 1.6 | 2.8 | 1.0 |
| rCE115/GLSuPA27//GCH065 | 1.5 | 1.0 | 1.0 |
| rCE115/rCE115GS//GCH065 | 0.6 | 0.9 | 1.0 |
| rCE115/rCE115//GCH065 | 0.9 | 0.7 | 1.0 |
| rCE115/rCE115uPA04//GCH065 | 3.8 | 2.7 | 1.0 |
| rCE115HAuPA20L/GLS//GCH065 | 2.4 | 1.2 | 1.0 |
| ANuPA20L/GLS//GCH065 | 1.7 | 1.0 | 1.0 |

As indicated in (i) of FIGS. 11 to 15, CD3 activation was observed with unmodified antibodies; however, CD3 activation was not observed with antibodies to which the masking molecule (γ) was attached using a linker sequence that is not cleavable by proteases. On the other hand, as indicated in (ii) of FIGS. 11 to 15, higher CD3 activation than before protease cleavage was observed for protease-treated antibodies to which the masking molecule (γ) was attached using a cancer tissue-specific protease-cleavable linker (β). Specifically, when a cancer tissue-specific protease-cleavable linker (β) was connected to the heavy chain, as indicated by hCE115HAuPA04, the change in CD3 activation before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus via the GGGS (SEQ ID NO:1) peptide sequence. The next largest amount of change was observed for the sequences in which the masking molecule (γ) was composed of 20 amino acids (hCE115HAuPA20, ANuPA20). When the masking molecule (γ) was composed of 27 amino acids (hCE115HAuPA27, ANuPA27), the increase rate in CD3 activation due to the protease treatment was remarkably decreased compared to the case where the masking molecule (γ) was composed of seven amino acids (hCE115HAuPA04). Similarly, when a cancer tissue-specific protease-cleavable linker (β) was connected to the light chain, as indicated by GLSuPA04, the change in CD3 activation before and after cleavage was the greatest under the conditions that the masking molecule (γ) consisted of seven amino acids, the cancer tissue-specific protease-cleavable linker (β) contained a GS linker composed of a repetition of GGGS (SEQ ID NO:1) and an uPA cleavable sequence, and the linker was linked to the heavy chain N terminus via the GGGS (SEQ ID NO:1) peptide sequence. The next largest amount of change was observed for the sequence in which the masking molecule (γ) was composed of 20 amino acids (GLSuPA20). When the masking molecule (γ) was composed of 27 amino acids (GLSuPA27), the increase rate in CD3 activation due to the protease treatment was decreased compared to the case where the masking molecule (γ) was composed of seven amino acids (GLSuPA04).

Examples 6 to 10 demonstrated that antibodies comprising a masking molecule (γ) having a naturally-occurring amino acid sequence and a cancer tissue-specific protease-cleavable linker (β) bound to the antigen in a protease-dependent manner, and activated CD3 by binding to CD3. This study revealed that a naturally-occurring sequence can be used as the masking molecule (γ), and showed that molecules exhibiting desired effects can be prepared by changing the length of the masking molecule (γ) according to a naturally-occurring sequence so that it will have an appropriate length as in the method indicated in the present Examples, or by changing the length of the linker. Besides the sequences used in the present Examples, those available as the cancer tissue-specific protease-cleavable linker (β) are described in JBC, Aug. 15, 1997, vol. 272, no. 33, 20456-20462; Proteomics 2005, 5, 1292-1298; Biochem. J. (2010) 426, 219-228; and WO2015/116933. Furthermore, an 8-amino-acid peptide sequences in which X1X2X3X4X5X6X7X8 (SEQ ID NO:131) are aligned as shown in Table 9 may also be used.

TABLE 9

| Position | Amino acid used this time [SEQ ID NO: 43] | Amino acid at each position |
|---|---|---|
| X1: | L | Y, W, F, M, A, Q, N, E, K |
| X2: | S | W, F, A, P, Q, E, D |
| X3: | G | Y, W, F, I, L, M, P, T, Q, N, H, C |
| X4: | R | Y, W, F, I, M, P, Q, N, E, D, K |
| X5: | S | W, I, L, M, A, G, Q, N, E, D, K, R, H |
| X6: | D | W, F, M, P, S, Q, K, R, C |
| X7: | N | Y, W, F, L, V, M, A, G, P, C |
| X8: | H | W, F, I, A, G, P, T, Q, E, D, K, C |

INDUSTRIAL APPLICABILITY

The multiple antigen-binding molecule fusion molecules of the present invention can be used in reagents for experimental studies, pharmaceuticals, and such.

According to the present invention, due to the binding of a masking molecule (γ) to a multiple antigen-binding molecule (α) via a cancer tissue-specific protease-cleavable linker (β), immune cells are not readily recruited to normal tissues, which provides an effect of reducing side effects caused by the multiple antigen-binding molecule (α), and therefore, the multiple antigen-binding molecule fusion molecules of the present invention are particularly useful as pharmaceuticals.

The invention claimed is:

1. A multiple antigen-binding molecule fusion molecule comprising:
   a multiple antigen-binding molecule (α) which comprises an immune cell antigen-binding region which recognizes an antigen that comprises a polypeptide consisting of the amino acid sequence QDGNE (SEQ ID NO: 15) and wherein the immune cell antigen-binding region recognizes at least one type of immune cell antigen other than the antigen that comprises a polypeptide consisting of the amino acid sequence QDGNE (SEQ ID NO: 15), and a cancer antigen-binding region which recognizes a cancer antigen;
   a cancer tissue-specific protease-cleavable linker (β) which comprises a polypeptide consisting of a target sequence of a cancer tissue-specific protease; and
   a masking molecule (γ) which comprises a polypeptide consisting of the amino acid sequence QDGNE (SEQ ID NO: 15);
   wherein the multiple antigen-binding molecule (α) is an antibody or an antibody fragment comprising at least two Fv regions, and the cancer antigen-binding region and the immune cell antigen-binding region are formed by different Fv regions;
   wherein the cancer tissue-specific protease-cleavable linker (β) is fused to a heavy chain N-terminus or a light chain N-terminus of the Fv region that forms the immune cell antigen-binding region;
   wherein the multiple antigen-binding molecule (α) and the masking molecule (γ) are linked via the cancer tissue-specific protease-cleavable linker (β); and
   wherein the cancer tissue-specific protease-cleavable linker (β) and the masking molecule (γ) form a linear fusion polypeptide, and
   wherein the number of amino acids in the fusion polypeptide is 11 or more to 65 or less when the cancer tissue-specific protease-cleavable linker (β) is fused to the heavy chain N-terminus of the Fv region that forms the immune cell antigen-binding region; and
   the number of amino acids in the fusion polypeptide is 16 or more to 65 or less when the cancer tissue-specific protease-cleavable linker (β) is fused to the light chain N terminus of the Fv region that forms the immune cell antigen-binding region.

2. The multiple antigen-binding molecule fusion molecule of claim 1, wherein the immune cell antigen-binding region does not recognize two or more immune cell antigens simultaneously.

3. The multiple antigen-binding molecule fusion molecule of claim 1, wherein light chains of the antibody or the antibody fragment comprising at least two Fv regions both comprise a same amino acid sequence.

4. The multiple antigen-binding molecule fusion molecule of claim 1, wherein the antibody or antibody fragment comprising at least two Fv regions further comprises an Fc region, and the Fc region is modified so as to lack a function of recognizing an Fcγ receptor.

5. The multiple antigen-binding molecule fusion molecule of claim 1, wherein the target sequence is the amino acid sequence PLGLAG (SEQ ID NO: 9).

6. A pharmaceutical composition which comprises the multiple antigen-binding molecule fusion molecule of claim 1 and a pharmaceutically acceptable carrier.

7. The pharmaceutical composition of claim 6, which is for treating cancer.

8. A method for treating cancer, wherein the method comprises administering the pharmaceutical composition of claim 6 to a patient.

9. The multiple antigen-binding molecule fusion molecule of claim 1, wherein the number of amino acids in the fusion polypeptide is 14 or more to 27 or less when the cancer tissue-specific protease-cleavable linker (β) is fused to the heavy chain N-terminus of the Fv region that forms the immune cell antigen-binding region.

10. The multiple antigen-binding molecule fusion molecule of claim 1, wherein the number of amino acids in the fusion polypeptide is 17 or more to 20 or less when the cancer tissue-specific protease-cleavable linker (β) is fused to the heavy chain N-terminus of the Fv region that forms the immune cell antigen-binding region.

11. The multiple antigen-binding molecule fusion molecule of claim 1, wherein the number of amino acids in the fusion polypeptide is 17 or more to 30 or less when the cancer tissue-specific protease-cleavable linker (β) is fused to the light chain N terminus of the Fv region that forms the immune cell antigen-binding region.

12. The multiple antigen-binding molecule fusion molecule of claim 1, wherein the number of amino acids in the fusion polypeptide is 19 or more to 25 or less when the cancer tissue-specific protease-cleavable linker (β) is fused to the light chain N terminus of the Fv region that forms the immune cell antigen-binding region.

* * * * *

UNITED STATES PATENT AND TRADEMARK OFFICE
CERTIFICATE OF CORRECTION

PATENT NO. : 11,400,157 B2
APPLICATION NO. : 15/573154
DATED : August 2, 2022
INVENTOR(S) : Igawa et al.

It is certified that error appears in the above-identified patent and that said Letters Patent is hereby corrected as shown below:

In the Specification

In Column 51, Table 9, at Line 4, please replace "Amino acid used this time [SEQ ID NO: 43]" with -- Amino acid used this time [SEQ ID NO: 47] --.

Signed and Sealed this
Third Day of January, 2023

Katherine Kelly Vidal
Director of the United States Patent and Trademark Office

SEQUENCE LISTING

```
<160> NUMBER OF SEQ ID NOS: 131

<210> SEQ ID NO 1
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 1

Gly Gly Gly Ser
1

<210> SEQ ID NO 2
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 2

Ser Gly Gly Gly
1

<210> SEQ ID NO 3
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 3

Gly Gly Gly Gly Ser
1               5

<210> SEQ ID NO 4
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 4

Ser Gly Gly Gly Gly
1               5

<210> SEQ ID NO 5
<211> LENGTH: 6
<212> TYPE: PRT
<213> ORGANISM: Artificial sequence
<220> FEATURE:
<223> OTHER INFORMATION: An artificially synthesized peptide sequence
```

```
<400> SEQUENCE: 5

Gly Gly Gly Gly Gly Ser
1               5

<210> SEQ ID NO 6
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 6

Ser Gly Gly Gly Gly Gly
1               5

<210> SEQ ID NO 7
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 7

Gly Gly Gly Gly Gly Gly Ser
1               5

<210> SEQ ID NO 8
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 8

Ser Gly Gly Gly Gly Gly Gly
1               5

<210> SEQ ID NO 9
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 9

Pro Leu Gly Leu Ala Gly
1               5

<210> SEQ ID NO 10
<211> LENGTH: 122
<212> TYPE: PRT
<213> ORGANISM: Rattus norvegicus

<400> SEQUENCE: 10

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
```

```
            65                  70                  75                  80
Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
                100                 105                 110

Gly Gln Gly Thr Ser Val Thr Val Ser Ser
            115                 120

<210> SEQ ID NO 11
<211> LENGTH: 112
<212> TYPE: PRT
<213> ORGANISM: Rattus norvegicus

<400> SEQUENCE: 11

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
                20                  25                  30

Asn Gly Asn Thr Tyr Val Ser Trp Tyr Ile Gln Lys Pro Ser Gln Ser
            35                  40                  45

Pro Gln Leu Leu Ile Tyr Lys Val Ser Asn Arg Phe Ser Gly Ile Ser
        50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
                100                 105                 110

<210> SEQ ID NO 12
<211> LENGTH: 122
<212> TYPE: PRT
<213> ORGANISM: Homo sapiens

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Ala Lys Ser Asn Asn Tyr Ala Thr Tyr Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
                100                 105                 110

Gly Gln Gly Thr Thr Val Thr Val Ser Ser
            115                 120

<210> SEQ ID NO 13
<211> LENGTH: 112
<212> TYPE: PRT
<213> ORGANISM: Homo sapiens

<400> SEQUENCE: 13
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110
```

<210> SEQ ID NO 14
<211> LENGTH: 15
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: misc_feature
<222> LOCATION: (1)..(1)
<223> OTHER INFORMATION: Xaa = L-pyroglutamic acid

<400> SEQUENCE: 14

```
Xaa Asp Gly Asn Glu Glu Met Gly Gly Ile Thr Gln Thr Pro Tyr
1               5                   10                  15
```

<210> SEQ ID NO 15
<211> LENGTH: 5
<212> TYPE: PRT
<213> ORGANISM: Homo sapiens

<400> SEQUENCE: 15

```
Gln Asp Gly Asn Glu
1               5
```

<210> SEQ ID NO 16
<211> LENGTH: 12
<212> TYPE: PRT
<213> ORGANISM: Artificial sequence
<220> FEATURE:
<223> OTHER INFORMATION: An artificially synthesized peptide sequence

<400> SEQUENCE: 16

```
Gly Gly Ser Pro Leu Gly Leu Ala Gly Gly Ser Gly
1               5                   10
```

<210> SEQ ID NO 17
<211> LENGTH: 15
<212> TYPE: PRT
<213> ORGANISM: Artificial sequence
<220> FEATURE:
<223> OTHER INFORMATION: An artificially synthesized peptide sequence

<400> SEQUENCE: 17

```
Gly Gly Ser Gly Gly Ser Pro Leu Gly Leu Ala Gly Gly Gly Ser
1               5                   10                  15
```

<210> SEQ ID NO 18
<211> LENGTH: 18

```
<212> TYPE: PRT
<213> ORGANISM: Artificial sequence
<220> FEATURE:
<223> OTHER INFORMATION: An artificially synthesized peptide sequence

<400> SEQUENCE: 18

Gly Gly Ser Gly Gly Ser Pro Leu Gly Leu Ala Gly Gly Gly Ser Gly
1               5                   10                  15

Gly Ser

<210> SEQ ID NO 19
<211> LENGTH: 25
<212> TYPE: PRT
<213> ORGANISM: Artificial sequence
<220> FEATURE:
<223> OTHER INFORMATION: An artificially synthesized peptide sequence

<400> SEQUENCE: 19

Gly Gly Ser Gly Gly Ser Gly Gly Ser Gly Gly Ser Gly Gly Ser Pro
1               5                   10                  15

Leu Gly Leu Ala Gly Gly Gly Ser Gly
            20                  25

<210> SEQ ID NO 20
<211> LENGTH: 458
<212> TYPE: PRT
<213> ORGANISM: Artificial sequence
<220> FEATURE:
<223> OTHER INFORMATION: An artificially synthesized peptide sequence

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220
```

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Ala Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Cys Glu Leu Thr Lys Asn Gln Val
    355                 360                 365

Ser Leu Ser Cys Ala Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Asp Tyr Lys Asp Asp Asp Lys
450                 455

<210> SEQ ID NO 21
<211> LENGTH: 475
<212> TYPE: PRT
<213> ORGANISM: Artificial sequence
<220> FEATURE:
<223> OTHER INFORMATION: An artificially synthesized peptide sequence

<400> SEQUENCE: 21

Gln Asp Gly Asn Glu Gly Gly Ser Pro Leu Gly Leu Ala Gly Gly Ser
1               5                   10                  15

Gly Gln Val Gln Leu Val Glu Ser Gly Gly Gly Val Val Gln Pro Gly
            20                  25                  30

Arg Ser Leu Arg Leu Ser Cys Ala Ala Ser Gly Phe Thr Phe Ser Asn
        35                  40                  45

Ala Trp Met His Trp Val Arg Gln Ala Pro Gly Lys Gly Leu Glu Trp
    50                  55                  60

Val Ala Gln Ile Lys Ala Lys Ser Asn Asn Tyr Ala Thr Tyr Tyr Ala
65                  70                  75                  80

Glu Ser Val Lys Gly Arg Phe Thr Ile Ser Arg Asp Asp Ser Lys Asn
            85                  90                  95

Ser Leu Tyr Leu Gln Met Asn Ser Leu Lys Thr Glu Asp Thr Ala Val
        100                 105                 110

Tyr Tyr Cys Arg Tyr Val His Tyr Gly Ala Tyr Tyr Gly Val Asp Ala
    115                 120                 125

Trp Gly Gln Gly Thr Thr Val Thr Val Ser Ser Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Ala Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Cys Glu Leu Thr Lys Asn Gln
370                 375                 380

Val Ser Leu Ser Cys Ala Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Val Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Asp Tyr Lys Asp Asp Asp Lys
465                 470                 475

<210> SEQ ID NO 22
<211> LENGTH: 478
<212> TYPE: PRT
<213> ORGANISM: Artificial sequence
<220> FEATURE:
<223> OTHER INFORMATION: An artificially synthesized peptide sequence

<400> SEQUENCE: 22

Gln Asp Gly Asn Glu Gly Gly Ser Gly Gly Ser Pro Leu Gly Leu Ala
1               5                   10                  15

-continued

Gly Gly Gly Ser Gln Val Gln Leu Val Glu Ser Gly Gly Val Val
         20                  25                  30

Gln Pro Gly Arg Ser Leu Arg Leu Ser Cys Ala Ala Ser Gly Phe Thr
             35                  40                  45

Phe Ser Asn Ala Trp Met His Trp Val Arg Gln Ala Pro Gly Lys Gly
 50                  55                  60

Leu Glu Trp Val Ala Gln Ile Lys Ala Lys Ser Asn Asn Tyr Ala Thr
 65                  70                  75                  80

Tyr Tyr Ala Glu Ser Val Lys Gly Arg Phe Thr Ile Ser Arg Asp Asp
                 85                  90                  95

Ser Lys Asn Ser Leu Tyr Leu Gln Met Asn Ser Leu Lys Thr Glu Asp
            100                 105                 110

Thr Ala Val Tyr Tyr Cys Arg Tyr Val His Tyr Gly Ala Tyr Tyr Gly
                115                 120                 125

Val Asp Ala Trp Gly Gln Gly Thr Thr Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Ala Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Ala Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Cys Glu Leu Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

```
Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Asp Tyr Lys Asp Asp Asp Lys
465                 470                 475
```

<210> SEQ ID NO 23
<211> LENGTH: 481
<212> TYPE: PRT
<213> ORGANISM: Artificial sequence
<220> FEATURE:
<223> OTHER INFORMATION: An artificially synthesized peptide sequence

<400> SEQUENCE: 23

```
Gln Asp Gly Asn Glu Gly Gly Ser Gly Gly Ser Pro Leu Gly Leu Ala
1               5                   10                  15

Gly Gly Gly Ser Gly Gly Ser Gln Val Gln Leu Val Glu Ser Gly Gly
                20                  25                  30

Gly Val Val Gln Pro Gly Arg Ser Leu Arg Leu Ser Cys Ala Ala Ser
            35                  40                  45

Gly Phe Thr Phe Ser Asn Ala Trp Met His Trp Val Arg Gln Ala Pro
        50                  55                  60

Gly Lys Gly Leu Glu Trp Val Ala Gln Ile Lys Ala Lys Ser Asn Asn
65                  70                  75                  80

Tyr Ala Thr Tyr Tyr Ala Glu Ser Val Lys Gly Arg Phe Thr Ile Ser
                85                  90                  95

Arg Asp Asp Ser Lys Asn Ser Leu Tyr Leu Gln Met Asn Ser Leu Lys
            100                 105                 110

Thr Glu Asp Thr Ala Val Tyr Tyr Cys Arg Tyr Val His Tyr Gly Ala
        115                 120                 125

Tyr Tyr Gly Val Asp Ala Trp Gly Gln Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Ala Ala Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320
```

-continued

```
Glu Glu Gln Tyr Ala Ser Thr Tyr Arg Val Ser Val Leu Thr Val
            325                 330                 335

Leu His Gln Asp Trp Leu Asn Gly Lys Glu Tyr Lys Cys Lys Val Ser
        340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Cys
370                 375                 380

Glu Leu Thr Lys Asn Gln Val Ser Leu Ser Cys Ala Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Val Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Asp Tyr Lys Asp Asp Asp Asp
465                 470                 475                 480

Lys

<210> SEQ ID NO 24
<211> LENGTH: 488
<212> TYPE: PRT
<213> ORGANISM: Artificial sequence
<220> FEATURE:
<223> OTHER INFORMATION: An artificially synthesized peptide sequence

<400> SEQUENCE: 24

Gln Asp Gly Asn Glu Gly Gly Ser Gly Gly Ser Gly Gly Ser Gly Gly
1               5                   10                  15

Ser Gly Gly Ser Pro Leu Gly Leu Ala Gly Gly Ser Gly Gln Val
            20                  25                  30

Gln Leu Val Glu Ser Gly Gly Gly Val Val Gln Pro Gly Arg Ser Leu
        35                  40                  45

Arg Leu Ser Cys Ala Ala Ser Gly Phe Thr Phe Ser Asn Ala Trp Met
    50                  55                  60

His Trp Val Arg Gln Ala Pro Gly Lys Gly Leu Glu Trp Val Ala Gln
65                  70                  75                  80

Ile Lys Ala Lys Ser Asn Asn Tyr Ala Thr Tyr Tyr Ala Glu Ser Val
                85                  90                  95

Lys Gly Arg Phe Thr Ile Ser Arg Asp Asp Ser Lys Asn Ser Leu Tyr
            100                 105                 110

Leu Gln Met Asn Ser Leu Lys Thr Glu Asp Thr Ala Val Tyr Tyr Cys
        115                 120                 125

Arg Tyr Val His Tyr Gly Ala Tyr Tyr Gly Val Asp Ala Trp Gly Gln
    130                 135                 140

Gly Thr Thr Val Thr Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
```

```
                    195                 200                 205
Leu Gln Ser Ser Gly Leu Tyr Ser Leu Ser Ser Val Val Thr Val Pro
        210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Ala Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Cys Glu Leu Thr Lys Asn Gln Val Ser Leu
385                 390                 395                 400

Ser Cys Ala Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Val Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Asp Tyr Lys Asp Asp Asp Asp Lys
                485

<210> SEQ ID NO 25
<211> LENGTH: 219
<212> TYPE: PRT
<213> ORGANISM: Artificial sequence
<220> FEATURE:
<223> OTHER INFORMATION: An artificially synthesized peptide sequence

<400> SEQUENCE: 25

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Gly Gln Gly
                    85                  90                  95

Thr Gln Val Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 26
<211> LENGTH: 14
<212> TYPE: PRT
<213> ORGANISM: Artificial sequence
<220> FEATURE:
<223> OTHER INFORMATION: An artificially synthesized peptide sequence

<400> SEQUENCE: 26

```
Gly Gly Gly Ser Pro Leu Gly Leu Ala Gly Gly Gly Ser Gly
1               5                   10
```

<210> SEQ ID NO 27
<211> LENGTH: 18
<212> TYPE: PRT
<213> ORGANISM: Artificial sequence
<220> FEATURE:
<223> OTHER INFORMATION: An artificially synthesized peptide sequence

<400> SEQUENCE: 27

```
Gly Gly Ser Gly Gly Ser Pro Leu Gly Leu Ala Gly Gly Gly Ser Gly
1               5                   10                  15

Gly Ser
```

<210> SEQ ID NO 28
<211> LENGTH: 19
<212> TYPE: PRT
<213> ORGANISM: Artificial sequence
<220> FEATURE:
<223> OTHER INFORMATION: An artificially synthesized peptide sequence

<400> SEQUENCE: 28

```
Gly Gly Ser Gly Gly Ser Gly Gly Ser Pro Leu Gly Leu Ala Gly Gly
1               5                   10                  15

Gly Ser Gly
```

<210> SEQ ID NO 29
<211> LENGTH: 219
<212> TYPE: PRT
<213> ORGANISM: Artificial sequence
<220> FEATURE:
<223> OTHER INFORMATION: An artificially synthesized peptide sequence

<400> SEQUENCE: 29

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 30
<211> LENGTH: 238
<212> TYPE: PRT
<213> ORGANISM: Artificial sequence
<220> FEATURE:
<223> OTHER INFORMATION: An artificially synthesized peptide sequence

<400> SEQUENCE: 30

Gln Asp Gly Asn Glu Gly Gly Ser Pro Leu Gly Leu Ala Gly Gly
1               5                   10                  15

Gly Ser Gly Asp Ile Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Arg Asn Thr Tyr Leu His Trp Tyr Gln Gln Lys Pro
    50                  55                  60

Gly Gln Ala Pro Arg Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gly Gln Gly Thr Gln Val Pro Tyr Thr Phe Gly Gln Gly Thr Lys Leu
        115                 120                 125

-continued

```
Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 31
<211> LENGTH: 242
<212> TYPE: PRT
<213> ORGANISM: Artificial sequence
<220> FEATURE:
<223> OTHER INFORMATION: An artificially synthesized peptide sequence

<400> SEQUENCE: 31

Gln Asp Gly Asn Glu Gly Gly Ser Gly Gly Ser Pro Leu Gly Leu Ala
1               5                   10                  15

Gly Gly Gly Ser Gly Gly Ser Asp Ile Val Met Thr Gln Ser Pro Leu
            20                  25                  30

Ser Leu Pro Val Thr Pro Gly Glu Pro Ala Ser Ile Ser Cys Arg Ser
        35                  40                  45

Ser Gln Ser Leu Val His Ser Asn Arg Asn Thr Tyr Leu His Trp Tyr
    50                  55                  60

Gln Gln Lys Pro Gly Gln Ala Pro Arg Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Val Gly
            100                 105                 110

Val Tyr Tyr Cys Gly Gln Gly Thr Gln Val Pro Tyr Thr Phe Gly Gln
        115                 120                 125

Gly Thr Lys Leu Glu Ile Lys Arg Thr Val Ala Ala Pro Ser Val Phe
130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys
```

```
<210> SEQ ID NO 32
<211> LENGTH: 243
<212> TYPE: PRT
<213> ORGANISM: Artificial sequence
<220> FEATURE:
<223> OTHER INFORMATION: An artificially synthesized peptide sequence

<400> SEQUENCE: 32

Gln Asp Gly Asn Glu Gly Gly Ser Gly Gly Ser Gly Gly Ser Pro Leu
1               5                   10                  15

Gly Leu Ala Gly Gly Ser Gly Asp Ile Val Met Thr Gln Ser Pro
            20                  25                  30

Leu Ser Leu Pro Val Thr Pro Gly Glu Pro Ala Ser Ile Ser Cys Arg
        35                  40                  45

Ser Ser Gln Ser Leu Val His Ser Asn Arg Asn Thr Tyr Leu His Trp
50                  55                  60

Tyr Gln Gln Lys Pro Gly Gln Ala Pro Arg Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Val
            100                 105                 110

Gly Val Tyr Tyr Cys Gly Gln Gly Thr Gln Val Pro Tyr Thr Phe Gly
        115                 120                 125

Gln Gly Thr Lys Leu Glu Ile Lys Arg Thr Val Ala Ala Pro Ser Val
    130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175

Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
        195                 200                 205

Thr Leu Ser Lys Ala Asp Tyr Glu Lys His Lys Val Tyr Ala Cys Glu
    210                 215                 220

Val Thr His Gln Gly Leu Ser Ser Pro Val Thr Lys Ser Phe Asn Arg
225                 230                 235                 240

Gly Glu Cys

<210> SEQ ID NO 33
<211> LENGTH: 249
<212> TYPE: PRT
<213> ORGANISM: Artificial sequence
<220> FEATURE:
<223> OTHER INFORMATION: An artificially synthesized peptide sequence

<400> SEQUENCE: 33

Gln Asp Gly Asn Glu Gly Gly Ser Gly Gly Ser Gly Gly Ser Gly Gly
1               5                   10                  15

Ser Gly Gly Ser Pro Leu Gly Leu Ala Gly Gly Ser Gly Asp Ile
            20                  25                  30

Val Met Thr Gln Ser Pro Leu Ser Leu Pro Val Thr Pro Gly Glu Pro
        35                  40                  45

Ala Ser Ile Ser Cys Arg Ser Ser Gln Ser Leu Val His Ser Asn Arg
    50                  55                  60

Asn Thr Tyr Leu His Trp Tyr Gln Gln Lys Pro Gly Gln Ala Pro Arg
```

```
                65                  70                  75                  80
Leu Leu Ile Tyr Lys Val Ser Asn Arg Phe Ser Gly Val Pro Asp Arg
                    85                  90                  95

Phe Ser Gly Ser Gly Ser Gly Thr Asp Phe Thr Leu Lys Ile Ser Arg
                    100                 105                 110

Val Glu Ala Glu Asp Val Gly Val Tyr Tyr Cys Gly Gln Gly Thr Gln
                    115                 120                 125

Val Pro Tyr Thr Phe Gly Gln Gly Thr Lys Leu Glu Ile Lys Arg Thr
                    130                 135                 140

Val Ala Ala Pro Ser Val Phe Ile Phe Pro Pro Ser Asp Glu Gln Leu
145                 150                 155                 160

Lys Ser Gly Thr Ala Ser Val Val Cys Leu Leu Asn Asn Phe Tyr Pro
                    165                 170                 175

Arg Glu Ala Lys Val Gln Trp Lys Val Asp Asn Ala Leu Gln Ser Gly
                    180                 185                 190

Asn Ser Gln Glu Ser Val Thr Glu Gln Asp Ser Lys Asp Ser Thr Tyr
                    195                 200                 205

Ser Leu Ser Ser Thr Leu Thr Leu Ser Lys Ala Asp Tyr Glu Lys His
                    210                 215                 220

Lys Val Tyr Ala Cys Glu Val Thr His Gln Gly Leu Ser Ser Pro Val
225                 230                 235                 240

Thr Lys Ser Phe Asn Arg Gly Glu Cys
                    245

<210> SEQ ID NO 34
<211> LENGTH: 458
<212> TYPE: PRT
<213> ORGANISM: Artificial sequence
<220> FEATURE:
<223> OTHER INFORMATION: An artificially synthesized peptide sequence

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
                    20                  25                  30

Trp Met His Trp Val Arg Gln Ala Pro Gly Lys Gly Leu Glu Trp Val
                    35                  40                  45

Ala Gln Ile Lys Ala Lys Ser Asn Asn Tyr Ala Thr Tyr Tyr Ala Glu
            50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                    85                  90                  95

Tyr Cys Arg Tyr Val His Tyr Gly Ala Tyr Gly Val Asp Ala Trp
                    100                 105                 110

Gly Gln Gly Thr Thr Val Thr Val Ser Ser Ala Ser Thr Lys Gly Pro
                    115                 120                 125

Ser Val Phe Pro Leu Ala Pro Ser Ser Lys Ser Thr Ser Gly Gly Thr
                    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
```

-continued

|  |  |  | 180 |  |  |  | 185 |  |  |  | 190 |  |  |
|---|---|---|---|---|---|---|---|---|---|---|---|---|---|

Val Pro Ser Ser Ser Leu Gly Thr Gln Thr Tyr Ile Cys Asn Val Asn
     195    200    205

His Lys Pro Ser Asn Thr Lys Val Asp Lys Val Glu Pro Lys Ser
210     215    220

Cys Asp Lys Thr His Thr Cys Pro Pro Cys Pro Ala Pro Glu Ala Ala
225    230    235    240

Gly Gly Pro Ser Val Phe Leu Phe Pro Pro Lys Pro Lys Asp Thr Leu
     245    250    255

Met Ile Ser Arg Thr Pro Glu Val Thr Cys Val Val Val Asp Val Ser
  260    265    270

His Glu Asp Pro Glu Val Lys Phe Asn Trp Tyr Val Asp Gly Val Glu
 275    280    285

Val His Asn Ala Lys Thr Lys Pro Arg Glu Glu Gln Tyr Ala Ser Thr
  290    295    300

Tyr Arg Val Val Ser Val Leu Thr Val Leu His Gln Asp Trp Leu Asn
305    310    315    320

Gly Lys Glu Tyr Lys Cys Lys Val Ser Asn Lys Ala Leu Pro Ala Pro
    325    330    335

Ile Glu Lys Thr Ile Ser Lys Ala Lys Gly Gln Pro Arg Glu Pro Gln
    340    345    350

Val Tyr Thr Leu Pro Pro Ser Arg Cys Glu Leu Thr Lys Asn Gln Val
    355    360    365

Ser Leu Ser Cys Ala Val Lys Gly Phe Tyr Pro Ser Asp Ile Ala Val
  370    375    380

Glu Trp Glu Ser Asn Gly Gln Pro Glu Asn Asn Tyr Lys Thr Thr Pro
385    390    395    400

Pro Val Leu Asp Ser Asp Gly Ser Phe Phe Leu Val Ser Lys Leu Thr
    405    410    415

Val Asp Lys Ser Arg Trp Gln Gln Gly Asn Val Phe Ser Cys Ser Val
    420    425    430

Met His Glu Ala Leu His Asn His Tyr Thr Gln Lys Ser Leu Ser Leu
    435    440    445

Ser Pro Asp Tyr Lys Asp Asp Asp Asp Lys
  450    455

<210> SEQ ID NO 35
<211> LENGTH: 336
<212> TYPE: PRT
<213> ORGANISM: Artificial sequence
<220> FEATURE:
<223> OTHER INFORMATION: An artificially synthesized peptide sequence

<400> SEQUENCE: 35

Ala Ser Thr Lys Gly Pro Ser Val Phe Pro Leu Ala Pro Ser Ser Lys
1    5    10    15

Ser Thr Ser Gly Gly Thr Ala Ala Leu Gly Cys Leu Val Lys Asp Tyr
    20    25    30

Phe Pro Glu Pro Val Thr Val Ser Trp Asn Ser Gly Ala Leu Thr Ser
   35    40    45

Gly Val His Thr Phe Pro Ala Val Leu Gln Ser Ser Gly Leu Tyr Ser
  50    55    60

Leu Ser Ser Val Val Thr Val Pro Ser Ser Ser Leu Gly Thr Gln Thr
65    70    75    80

Tyr Ile Cys Asn Val Asn His Lys Pro Ser Asn Thr Lys Val Asp Lys

```
                     85                  90                  95
Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Val Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Asp Tyr Lys Asp Asp Asp Asp Lys
                325                 330                 335

<210> SEQ ID NO 36
<211> LENGTH: 107
<212> TYPE: PRT
<213> ORGANISM: Homo sapiens

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 37
<211> LENGTH: 230
```

```
<212> TYPE: PRT
<213> ORGANISM: Artificial sequence
<220> FEATURE:
<223> OTHER INFORMATION: An artificially synthesized peptide sequence

<400> SEQUENCE: 37

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Tyr Thr Gln Lys
210                 215                 220

Ser Leu Ser Leu Ser Pro
225                 230

<210> SEQ ID NO 38
<211> LENGTH: 328
<212> TYPE: PRT
<213> ORGANISM: Artificial sequence
<220> FEATURE:
<223> OTHER INFORMATION: An artificially synthesized peptide sequence

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 39
<211> LENGTH: 328
<212> TYPE: PRT
<213> ORGANISM: Artificial sequence
<220> FEATURE:
<223> OTHER INFORMATION: An artificially synthesized peptide sequence

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
            115                 120                 125

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 40
<211> LENGTH: 456
<212> TYPE: PRT
<213> ORGANISM: Artificial sequence
<220> FEATURE:
<223> OTHER INFORMATION: An artificially synthesized peptide sequence

<400> SEQUENCE: 40

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gly Tyr Asn Ala Tyr Tyr Ala Glu
    50                  55                  60

Ser Val Lys Gly Arg Phe Thr Ile Ser Arg Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ala Gly Phe Ser Tyr Lys
            100                 105                 110

Phe Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160
```

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Arg Gly Gly Pro Lys Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Lys Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Tyr Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro
    450                 455

<210> SEQ ID NO 41
<211> LENGTH: 373
<212> TYPE: PRT
<213> ORGANISM: Artificial sequence
<220> FEATURE:
<223> OTHER INFORMATION: An artificially synthesized peptide sequence

<400> SEQUENCE: 41

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
            85                  90                  95

Val Cys Glu Asn Cys Met Glu Met Asp Asp Ile Glu Gly Arg Met Asp
            100                 105                 110

Pro Lys Ser Cys Asp Lys Thr His Thr Cys Pro Pro Cys Pro Ala Pro
            115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Cys Thr Leu Pro Pro Ser Arg Asp Glu Leu Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn Arg Tyr Thr Gln Lys Ser
                325                 330                 335

Leu Ser Leu Ser Pro Gly Gly Ser Gly Gly Ser Gly Glu Asn Leu Tyr
            340                 345                 350

Phe Gln Gly Ser Gly Gly Gly Leu Asn Asp Ile Phe Glu Ala Gln Lys
            355                 360                 365

Ile Glu Trp His Glu
    370

<210> SEQ ID NO 42
<211> LENGTH: 323
<212> TYPE: PRT
<213> ORGANISM: Artificial sequence
<220> FEATURE:
<223> OTHER INFORMATION: An artificially synthesized peptide sequence

<400> SEQUENCE: 42

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

-continued

Ile Tyr Arg Cys Asn Gly Thr Asp Ile Tyr Lys Asp Lys Glu Ser Thr
 50                  55                  60

Val Gln Val His Tyr Arg Met Cys Gln Ser Cys Val Glu Leu Asp Asp
 65                  70                  75                  80

Ile Glu Gly Arg Met Asp Pro Lys Ser Cys Asp Lys Thr His Thr Cys
                 85                  90                  95

Pro Pro Cys Pro Ala Pro Glu Leu Leu Gly Pro Ser Val Phe Leu
            100                 105                 110

Phe Pro Pro Lys Pro Lys Asp Thr Leu Met Ile Ser Arg Thr Pro Glu
            115                 120                 125

Val Thr Cys Val Val Val Asp Val Ser His Glu Asp Pro Glu Val Lys
            130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
                180                 185                 190

Val Ser Asn Lys Ala Leu Pro Ala Pro Ile Glu Lys Thr Ile Ser Lys
            195                 200                 205

Ala Lys Gly Gln Pro Arg Glu Pro Gln Val Tyr Thr Leu Pro Pro Ser
    210                 215                 220

Arg Cys Glu Leu Thr Lys Asn Gln Val Ser Leu Ser Cys Ala Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Val Ser Lys Leu Thr Val Asp Lys Ser Arg Trp Gln
            275                 280                 285

Gln Gly Asn Val Phe Ser Cys Ser Val Met His Glu Ala Leu His Asn
    290                 295                 300

His Tyr Thr Gln Lys Ser Leu Ser Leu Ser Pro Asp Tyr Lys Asp Asp
305                 310                 315                 320

Asp Asp Lys

<210> SEQ ID NO 43
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 43

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gly Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

```
Ile Tyr Leu Gln Met Asn Ser Leu Lys Thr Glu Asp Thr Ala Val Tyr
                    85                  90                  95

Tyr Cys Arg Tyr Val His Tyr Thr Tyr Ala Gly Phe Ser Tyr Lys
                100                 105                 110

Phe Gly Val Asp Ala Trp Gly Gln Gly Thr Thr Val Thr Val Ser Ser
            115                 120                 125

<210> SEQ ID NO 44
<211> LENGTH: 450
<212> TYPE: PRT
<213> ORGANISM: Artificial sequence
<220> FEATURE:
<223> OTHER INFORMATION: An artificially synthesized peptide sequence

<400> SEQUENCE: 44

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
                20                  25                  30

Trp Met His Trp Val Arg Gln Ser Pro Glu Lys Gln Leu Glu Trp Val
            35                  40                  45

Ala Gln Ile Lys Ala Lys Ser Asn Asn Tyr Ala Thr Tyr Tyr Ala Glu
        50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                    85                  90                  95

Tyr Cys Arg Tyr Val His Tyr Gly Ala Tyr Tyr Gly Val Asp Ala Trp
                100                 105                 110

Gly Gln Gly Thr Ser Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Arg
225                 230                 235                 240

Gly Gly Pro Lys Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Ala Ser Thr
        290                 295                 300

Tyr Arg Val Val Ser Val Leu Thr Val Leu His Gln Asp Trp Leu Asn
305                 310                 315                 320
```

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Lys Glu Met Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Tyr Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro
    450

<210> SEQ ID NO 45
<211> LENGTH: 219
<212> TYPE: PRT
<213> ORGANISM: Artificial sequence
<220> FEATURE:
<223> OTHER INFORMATION: An artificially synthesized peptide sequence

<400> SEQUENCE: 45

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
                20                  25                  30

Asn Gly Asn Thr Tyr Val Ser Trp Tyr Ile Gln Lys Pro Ser Gln Ser
            35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

-continued

```
<210> SEQ ID NO 46
<211> LENGTH: 450
<212> TYPE: PRT
<213> ORGANISM: Artificial sequence
<220> FEATURE:
<223> OTHER INFORMATION: An artificially synthesized peptide sequence

<400> SEQUENCE: 46

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Arg
225                 230                 235                 240

Gly Gly Pro Lys Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Lys Glu Met Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Tyr Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro
    450

<210> SEQ ID NO 47
<211> LENGTH: 8
<212> TYPE: PRT
<213> ORGANISM: Artificial sequence
<220> FEATURE:
<223> OTHER INFORMATION: An artificially synthesized peptide sequence

<400> SEQUENCE: 47

Leu Ser Gly Arg Ser Asp Asn His
1               5

<210> SEQ ID NO 48
<211> LENGTH: 232
<212> TYPE: PRT
<213> ORGANISM: Artificial sequence
<220> FEATURE:
<223> OTHER INFORMATION: An artificially synthesized peptide sequence

<400> SEQUENCE: 48

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 49
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 49

Gln Asp Gly Asn Glu Glu Met
1               5

<210> SEQ ID NO 50
<211> LENGTH: 20
<212> TYPE: PRT
<213> ORGANISM: Artificial sequence
<220> FEATURE:
<223> OTHER INFORMATION: An artificially synthesized peptide sequence

<400> SEQUENCE: 50

Gln Asp Gly Asn Glu Glu Met Gly Gly Ile Thr Gln Thr Pro Tyr Lys
1               5                   10                  15

Val Ser Ile Ser
            20

<210> SEQ ID NO 51
<211> LENGTH: 27
<212> TYPE: PRT
<213> ORGANISM: Artificial sequence
<220> FEATURE:
<223> OTHER INFORMATION: An artificially synthesized peptide sequence

<400> SEQUENCE: 51

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25

<210> SEQ ID NO 52
<211> LENGTH: 8
<212> TYPE: PRT
<213> ORGANISM: Artificial sequence
<220> FEATURE:
<223> OTHER INFORMATION: An artificially synthesized peptide sequence

<400> SEQUENCE: 52

Gly Gly Gly Ser Gly Gly Gly Ser
1               5

<210> SEQ ID NO 53
<211> LENGTH: 24
<212> TYPE: PRT
<213> ORGANISM: Artificial sequence
<220> FEATURE:
<223> OTHER INFORMATION: An artificially synthesized peptide sequence

<400> SEQUENCE: 53

Gly Gly Gly Ser Gly Gly Gly Ser Gly Gly Gly Ser Leu Ser Gly Arg
1               5                   10                  15

Ser Asp Asn His Gly Gly Gly Ser
```

```
                     20

<210> SEQ ID NO 54
<211> LENGTH: 12
<212> TYPE: PRT
<213> ORGANISM: Artificial sequence
<220> FEATURE:
<223> OTHER INFORMATION: An artificially synthesized peptide sequence

<400> SEQUENCE: 54

Leu Ser Gly Arg Ser Asp Asn His Gly Gly Gly Ser
1               5                   10

<210> SEQ ID NO 55
<211> LENGTH: 14
<212> TYPE: PRT
<213> ORGANISM: Artificial sequence
<220> FEATURE:
<223> OTHER INFORMATION: An artificially synthesized peptide sequence

<400> SEQUENCE: 55

Gly Gly Gly Gly Ser Pro Leu Ser Leu Ala Gly Gly Gly Ser
1               5                   10

<210> SEQ ID NO 56
<211> LENGTH: 12
<212> TYPE: PRT
<213> ORGANISM: Artificial sequence
<220> FEATURE:
<223> OTHER INFORMATION: An artificially synthesized peptide sequence

<400> SEQUENCE: 56

Gly Gly Gly Ser Gly Gly Gly Ser Gly Gly Gly Ser
1               5                   10

<210> SEQ ID NO 57
<211> LENGTH: 17
<212> TYPE: PRT
<213> ORGANISM: Artificial sequence
<220> FEATURE:
<223> OTHER INFORMATION: An artificially synthesized peptide sequence

<400> SEQUENCE: 57

Gly Gly Gly Gly Ser Leu Ser Gly Arg Ser Asp Asn His Gly Gly Gly
1               5                   10                  15

Ser

<210> SEQ ID NO 58
<211> LENGTH: 135
<212> TYPE: PRT
<213> ORGANISM: Artificial sequence
<220> FEATURE:
<223> OTHER INFORMATION: An artificially synthesized peptide sequence

<400> SEQUENCE: 58

Gln Asp Gly Asn Glu Gly Gly Gly Ser Gly Gly Gly Ser Gln Val Gln
1               5                   10                  15

Leu Val Glu Ser Gly Gly Gly Val Val Gln Pro Gly Arg Ser Leu Arg
                20                  25                  30

Leu Ser Cys Ala Ala Ser Gly Phe Thr Phe Ser Asn Ala Trp Met His
            35                  40                  45

Trp Val Arg Gln Ala Pro Gly Lys Gly Leu Glu Trp Val Ala Gln Ile
        50                  55                  60

Lys Ala Lys Ser Asn Asn Tyr Ala Thr Tyr Tyr Ala Glu Ser Val Lys
```

```
                65                   70                   75                   80
Gly Arg Phe Thr Ile Ser Arg Asp Asp Ser Lys Asn Ser Leu Tyr Leu
                    85                   90                   95
Gln Met Asn Ser Leu Lys Thr Glu Asp Thr Ala Val Tyr Tyr Cys Arg
            100                 105                 110
Tyr Val His Tyr Gly Ala Tyr Tyr Gly Val Asp Ala Trp Gly Gln Gly
            115                 120                 125
Thr Thr Val Thr Val Ser Ser
            130                 135

<210> SEQ ID NO 59
<211> LENGTH: 27
<212> TYPE: PRT
<213> ORGANISM: Artificial sequence
<220> FEATURE:
<223> OTHER INFORMATION: An artificially synthesized peptide sequence

<400> SEQUENCE: 59

Gly Gly Gly Gly Ser Gly Gly Gly Ser Gly Gly Gly Gly Ser Leu
1               5                   10                  15

Ser Gly Arg Ser Asp Asn His Gly Gly Gly Ser
            20                  25

<210> SEQ ID NO 60
<211> LENGTH: 153
<212> TYPE: PRT
<213> ORGANISM: Artificial sequence
<220> FEATURE:
<223> OTHER INFORMATION: An artificially synthesized peptide sequence

<400> SEQUENCE: 60

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Gln
            20                  25                  30

Val Gln Leu Val Glu Ser Gly Gly Val Val Gln Pro Gly Arg Ser
            35                  40                  45

Leu Arg Leu Ser Cys Ala Ala Ser Gly Phe Thr Phe Ser Asn Ala Trp
    50                  55                  60

Met His Trp Val Arg Gln Ala Pro Gly Lys Gly Leu Glu Trp Val Ala
65                  70                  75                  80

Gln Ile Lys Ala Lys Ser Asn Asn Tyr Ala Thr Tyr Tyr Ala Glu Ser
                85                  90                  95

Val Lys Gly Arg Phe Thr Ile Ser Arg Asp Asp Ser Lys Asn Ser Leu
            100                 105                 110

Tyr Leu Gln Met Asn Ser Leu Lys Thr Glu Asp Thr Ala Val Tyr Tyr
            115                 120                 125

Cys Arg Tyr Val His Tyr Gly Ala Tyr Tyr Gly Val Asp Ala Trp Gly
            130                 135                 140

Gln Gly Thr Thr Val Thr Val Ser Ser
145                 150

<210> SEQ ID NO 61
<211> LENGTH: 154
<212> TYPE: PRT
<213> ORGANISM: Artificial sequence
<220> FEATURE:
<223> OTHER INFORMATION: An artificially synthesized peptide sequence

<400> SEQUENCE: 61
```

Gln Asp Gly Asn Glu Glu Met Gly Gly Ile Thr Gln Thr Pro Tyr Lys
1               5                   10                  15

Val Ser Ile Ser Leu Ser Gly Arg Ser Asp Asn His Gly Gly Gly Ser
            20                  25                  30

Gln Val Gln Leu Val Glu Ser Gly Gly Val Val Gln Pro Gly Arg
        35                  40                  45

Ser Leu Arg Leu Ser Cys Ala Ala Ser Gly Phe Thr Phe Ser Asn Ala
50                  55                  60

Trp Met His Trp Val Arg Gln Ala Pro Gly Lys Gly Leu Glu Trp Val
65                  70                  75                  80

Ala Gln Ile Lys Ala Lys Ser Asn Asn Tyr Ala Thr Tyr Tyr Ala Glu
                85                  90                  95

Ser Val Lys Gly Arg Phe Thr Ile Ser Arg Asp Asp Ser Lys Asn Ser
                100                 105                 110

Leu Tyr Leu Gln Met Asn Ser Leu Lys Thr Glu Asp Thr Ala Val Tyr
        115                 120                 125

Tyr Cys Arg Tyr Val His Tyr Gly Ala Tyr Tyr Gly Val Asp Ala Trp
        130                 135                 140

Gly Gln Gly Thr Thr Val Thr Val Ser Ser
145                 150

<210> SEQ ID NO 62
<211> LENGTH: 169
<212> TYPE: PRT
<213> ORGANISM: Artificial sequence
<220> FEATURE:
<223> OTHER INFORMATION: An artificially synthesized peptide sequence

<400> SEQUENCE: 62

Gln Asp Gly Asn Glu Glu Met Gly Gly Ile Thr Gln Thr Pro Tyr Lys
1               5                   10                  15

Val Ser Ile Ser Gly Gly Gly Gly Ser Gly Gly Gly Gly Ser Gly Gly
            20                  25                  30

Gly Gly Ser Leu Ser Gly Arg Ser Asp Asn His Gly Gly Gly Ser Gln
        35                  40                  45

Val Gln Leu Val Glu Ser Gly Gly Val Val Gln Pro Gly Arg Ser
50                  55                  60

Leu Arg Leu Ser Cys Ala Ala Ser Gly Phe Thr Phe Ser Asn Ala Trp
65                  70                  75                  80

Met His Trp Val Arg Gln Ala Pro Gly Lys Gly Leu Glu Trp Val Ala
                85                  90                  95

Gln Ile Lys Ala Lys Ser Asn Asn Tyr Ala Thr Tyr Tyr Ala Glu Ser
                100                 105                 110

Val Lys Gly Arg Phe Thr Ile Ser Arg Asp Asp Ser Lys Asn Ser Leu
        115                 120                 125

Tyr Leu Gln Met Asn Ser Leu Lys Thr Glu Asp Thr Ala Val Tyr Tyr
        130                 135                 140

Cys Arg Tyr Val His Tyr Gly Ala Tyr Tyr Gly Val Asp Ala Trp Gly
145                 150                 155                 160

Gln Gly Thr Thr Val Thr Val Ser Ser
                165

<210> SEQ ID NO 63
<211> LENGTH: 157
<212> TYPE: PRT
<213> ORGANISM: Artificial sequence
<220> FEATURE:
<223> OTHER INFORMATION: An artificially synthesized peptide sequence

<400> SEQUENCE: 63

Gln Asp Gly Asn Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30

Asp Asn His Gln Val Gln Leu Val Glu Ser Gly Gly Gly Val Val Gln
        35                  40                  45

Pro Gly Arg Ser Leu Arg Leu Ser Cys Ala Ala Ser Gly Phe Thr Phe
    50                  55                  60

Ser Asn Ala Trp Met His Trp Val Arg Gln Ala Pro Gly Lys Gly Leu
65                  70                  75                  80

Glu Trp Val Ala Gln Ile Lys Ala Lys Ser Asn Asn Tyr Ala Thr Tyr
                85                  90                  95

Tyr Ala Glu Ser Val Lys Gly Arg Phe Thr Ile Ser Arg Asp Asp Ser
            100                 105                 110

Lys Asn Ser Leu Tyr Leu Gln Met Asn Ser Leu Lys Thr Glu Asp Thr
        115                 120                 125

Ala Val Tyr Tyr Cys Arg Tyr Val His Tyr Gly Ala Tyr Tyr Gly Val
    130                 135                 140

Asp Ala Trp Gly Gln Gly Thr Thr Val Thr Val Ser Ser
145                 150                 155

<210> SEQ ID NO 64
<211> LENGTH: 141
<212> TYPE: PRT
<213> ORGANISM: Artificial sequence
<220> FEATURE:
<223> OTHER INFORMATION: An artificially synthesized peptide sequence

<400> SEQUENCE: 64

Gln Asp Gly Asn Glu Gly Gly Gly Gly Ser Pro Leu Gly Leu Ala Gly
1               5                   10                  15

Gly Gly Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Ala Trp Met His Trp Val Arg Gln Ala Pro Gly Lys Gly Leu
    50                  55                  60

Glu Trp Val Ala Gln Ile Lys Ala Lys Ser Asn Asn Tyr Ala Thr Tyr
65                  70                  75                  80

Tyr Ala Glu Ser Val Lys Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Arg Tyr Val His Tyr Gly Ala Tyr Tyr Gly Val
        115                 120                 125

Asp Ala Trp Gly Gln Gly Thr Thr Val Thr Val Ser Ser
    130                 135                 140

<210> SEQ ID NO 65
<211> LENGTH: 129
<212> TYPE: PRT
<213> ORGANISM: Artificial sequence
<220> FEATURE:
<223> OTHER INFORMATION: An artificially synthesized peptide sequence

<400> SEQUENCE: 65

Gln Asp Gly Asn Glu Gly Gly Ser Gly Gly Ser Gly Gly Gly
1               5                   10                  15

Ser Asp Ile Val Met Thr Gln Ser Pro Leu Ser Leu Pro Val Thr Pro
            20                  25                  30

Gly Glu Pro Ala Ser Ile Ser Cys Arg Ser Ser Gln Ser Leu Val His
        35                  40                  45

Ser Asn Arg Asn Thr Tyr Leu His Trp Tyr Gln Gln Lys Pro Gly Gln
    50                  55                  60

Ala Pro Arg Leu Leu Ile Tyr Lys Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
        115                 120                 125

Lys

<210> SEQ ID NO 66
<211> LENGTH: 129
<212> TYPE: PRT
<213> ORGANISM: Artificial sequence
<220> FEATURE:
<223> OTHER INFORMATION: An artificially synthesized peptide sequence

<400> SEQUENCE: 66

Gln Asp Gly Asn Glu Leu Ser Gly Arg Ser Asp Asn His Gly Gly Gly
1               5                   10                  15

Ser Asp Ile Val Met Thr Gln Ser Pro Leu Ser Leu Pro Val Thr Pro
            20                  25                  30

Gly Glu Pro Ala Ser Ile Ser Cys Arg Ser Ser Gln Ser Leu Val His
        35                  40                  45

Ser Asn Arg Asn Thr Tyr Leu His Trp Tyr Gln Gln Lys Pro Gly Gln
    50                  55                  60

Ala Pro Arg Leu Leu Ile Tyr Lys Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
        115                 120                 125

Lys

<210> SEQ ID NO 67
<211> LENGTH: 143
<212> TYPE: PRT
<213> ORGANISM: Artificial sequence
<220> FEATURE:
<223> OTHER INFORMATION: An artificially synthesized peptide sequence

<400> SEQUENCE: 67

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Asp

```
                20                  25                  30

Ile Val Met Thr Gln Ser Pro Leu Ser Leu Pro Val Thr Pro Gly Glu
            35                  40                  45

Pro Ala Ser Ile Ser Cys Arg Ser Ser Gln Ser Leu Val His Ser Asn
        50                  55                  60

Arg Asn Thr Tyr Leu His Trp Tyr Gln Gln Lys Pro Gly Gln Ala Pro
65                  70                  75                  80

Arg Leu Leu Ile Tyr Lys Val Ser Asn Arg Phe Ser Gly Val Pro Asp
                85                  90                  95

Arg Phe Ser Gly Ser Gly Ser Gly Thr Asp Phe Thr Leu Lys Ile Ser
            100                 105                 110

Arg Val Glu Ala Glu Asp Val Gly Val Tyr Tyr Cys Gly Gln Gly Thr
        115                 120                 125

Gln Val Pro Tyr Thr Phe Gly Gln Gly Thr Lys Leu Glu Ile Lys
    130                 135                 140

<210> SEQ ID NO 68
<211> LENGTH: 159
<212> TYPE: PRT
<213> ORGANISM: Artificial sequence
<220> FEATURE:
<223> OTHER INFORMATION: An artificially synthesized peptide sequence

<400> SEQUENCE: 68

Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
            20                  25                  30

Gly Gly Ser Leu Ser Gly Arg Ser Asp Asn His Gly Gly Ser Asp
        35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Gln Ser Leu Val His Ser Asn
65                  70                  75                  80

Arg Asn Thr Tyr Leu His Trp Tyr Gln Gln Lys Pro Gly Gln Ala Pro
                85                  90                  95

Arg Leu Leu Ile Tyr Lys Val Ser Asn Arg Phe Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Gly Gln Gly Thr
    130                 135                 140

Gln Val Pro Tyr Thr Phe Gly Gln Gly Thr Lys Leu Glu Ile Lys
145                 150                 155

<210> SEQ ID NO 69
<211> LENGTH: 147
<212> TYPE: PRT
<213> ORGANISM: Artificial sequence
<220> FEATURE:
<223> OTHER INFORMATION: An artificially synthesized peptide sequence

<400> SEQUENCE: 69

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30
```

Asp Asn His Asp Ile Val Met Thr Gln Ser Pro Leu Ser Leu Pro Val
                35                  40                  45

Thr Pro Gly Glu Pro Ala Ser Ile Ser Cys Arg Ser Ser Gln Ser Leu
 50                  55                  60

Val His Ser Asn Arg Asn Thr Tyr Leu His Trp Tyr Gln Gln Lys Pro
 65                  70                  75                  80

Gly Gln Ala Pro Arg Leu Leu Ile Tyr Lys Val Ser Asn Arg Phe Ser
                 85                  90                  95

Gly Val Pro Asp Arg Phe Ser Gly Ser Gly Ser Gly Thr Asp Phe Thr
                100                 105                 110

Leu Lys Ile Ser Arg Val Glu Ala Glu Asp Val Gly Val Tyr Tyr Cys
                115                 120                 125

Gly Gln Gly Thr Gln Val Pro Tyr Thr Phe Gly Gln Gly Thr Lys Leu
        130                 135                 140

Glu Ile Lys
145

<210> SEQ ID NO 70
<211> LENGTH: 131
<212> TYPE: PRT
<213> ORGANISM: Artificial sequence
<220> FEATURE:
<223> OTHER INFORMATION: An artificially synthesized peptide sequence

<400> SEQUENCE: 70

Gln Asp Gly Asn Glu Gly Gly Gly Ser Pro Leu Gly Leu Ala Gly
1               5                   10                  15

Gly Gly Ser Asp Ile Val Met Thr Gln Ser Pro Leu Ser Leu Pro Val
                20                  25                  30

Thr Pro Gly Glu Pro Ala Ser Ile Ser Cys Arg Ser Ser Gln Ser Leu
        35                  40                  45

Val His Ser Asn Arg Asn Thr Tyr Leu His Trp Tyr Gln Gln Lys Pro
 50                  55                  60

Gly Gln Ala Pro Arg Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Val Gly Val Tyr Tyr Cys
                100                 105                 110

Gly Gln Gly Thr Gln Val Pro Tyr Thr Phe Gly Gln Gly Thr Lys Leu
                115                 120                 125

Glu Ile Lys
        130

<210> SEQ ID NO 71
<211> LENGTH: 129
<212> TYPE: PRT
<213> ORGANISM: Artificial sequence
<220> FEATURE:
<223> OTHER INFORMATION: An artificially synthesized peptide sequence

<400> SEQUENCE: 71

Gln Asp Gly Asn Glu Gly Gly Ser Gly Gly Ser Gly Gly
1               5                   10                  15

Ser Asp Ile Val Met Thr Gln Ser Pro Leu Ser Leu Pro Val Thr Pro
                20                  25                  30

Gly Glu Pro Ala Ser Ile Ser Cys Arg Ser Ser Gln Ser Leu Val His
        35                  40                  45

Ser Asn Arg Asn Thr Tyr Leu His Trp Tyr Gln Gln Lys Pro Gly Gln
        50                  55                  60

Ala Pro Arg Leu Leu Ile Tyr Lys Val Ser Asn Arg Phe Ser Gly Val
 65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
        115                 120                 125

Lys

<210> SEQ ID NO 72
<211> LENGTH: 144
<212> TYPE: PRT
<213> ORGANISM: Artificial sequence
<220> FEATURE:
<223> OTHER INFORMATION: An artificially synthesized peptide sequence

<400> SEQUENCE: 72

Gln Asp Gly Asn Glu Glu Met Gly Gly Ile Thr Gln Thr Pro Tyr Lys
 1               5                  10                  15

Val Ser Ile Ser Leu Ser Gly Arg Ser Asp Asn His Gly Gly Gly Ser
            20                  25                  30

Asp Ile Val Met Thr Gln Ser Pro Leu Ser Leu Pro Val Thr Pro Gly
        35                  40                  45

Glu Pro Ala Ser Ile Ser Cys Arg Ser Ser Gln Ser Leu Val His Ser
 50                  55                  60

Asn Arg Asn Thr Tyr Leu His Trp Tyr Gln Gln Lys Pro Gly Gln Ala
 65                  70                  75                  80

Pro Arg Leu Leu Ile Tyr Lys Val Ser Asn Arg Phe Ser Gly Val Pro
                85                  90                  95

Asp Arg Phe Ser Gly Ser Gly Ser Gly Thr Asp Phe Thr Leu Lys Ile
            100                 105                 110

Ser Arg Val Glu Ala Glu Asp Val Gly Val Tyr Tyr Cys Gly Gln Gly
        115                 120                 125

Thr Gln Val Pro Tyr Thr Phe Gly Gln Gly Thr Lys Leu Glu Ile Lys
    130                 135                 140

<210> SEQ ID NO 73
<211> LENGTH: 131
<212> TYPE: PRT
<213> ORGANISM: Artificial sequence
<220> FEATURE:
<223> OTHER INFORMATION: An artificially synthesized peptide sequence

<400> SEQUENCE: 73

Gln Asp Gly Asn Glu Gly Gly Gly Ser Pro Leu Gly Leu Ala Gly
 1               5                  10                  15

Gly Gly Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Arg Asn Thr Tyr Leu His Trp Tyr Gln Gln Lys Pro
 50                  55                  60

Gly Gln Ala Pro Arg Leu Leu Ile Tyr Lys Val Ser Asn Arg Phe Ser
 65                  70                  75                  80

```
Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gly Gln Gly Thr Gln Val Pro Tyr Thr Phe Gly Gln Gly Thr Lys Leu
        115                 120                 125

Glu Ile Lys
        130

<210> SEQ ID NO 74
<211> LENGTH: 141
<212> TYPE: PRT
<213> ORGANISM: Artificial sequence
<220> FEATURE:
<223> OTHER INFORMATION: An artificially synthesized peptide sequence

<400> SEQUENCE: 74

Gln Asp Gly Asn Glu Gly Gly Ser Gly Gly Gly Ser Gln Val Gln
1               5                   10                  15

Leu Val Glu Ser Gly Gly Gly Leu Val Gln Pro Gly Arg Ser Leu Arg
            20                  25                  30

Leu Ser Cys Ala Ala Ser Gly Phe Thr Phe Ser Asn Ala Trp Met His
        35                  40                  45

Trp Val Arg Gln Ala Pro Gly Lys Gly Leu Glu Trp Val Ala Gln Ile
    50                  55                  60

Lys Asp Lys Ala Asn Gly Tyr Asn Ala Tyr Tyr Ala Glu Ser Val Lys
65                  70                  75                  80

Gly Arg Phe Thr Ile Ser Arg Asp Asp Ser Lys Asn Ser Ile Tyr Leu
                85                  90                  95

Gln Met Asn Ser Leu Lys Thr Glu Asp Thr Ala Val Tyr Tyr Cys Arg
            100                 105                 110

Tyr Val His Tyr Thr Thr Tyr Ala Gly Phe Ser Tyr Lys Phe Gly Val
        115                 120                 125

Asp Ala Trp Gly Gln Gly Thr Thr Val Thr Val Ser Ser
    130                 135                 140

<210> SEQ ID NO 75
<211> LENGTH: 150
<212> TYPE: PRT
<213> ORGANISM: Artificial sequence
<220> FEATURE:
<223> OTHER INFORMATION: An artificially synthesized peptide sequence

<400> SEQUENCE: 75

Gln Asp Gly Asn Glu Gly Gly Gly Gly Ser Leu Ser Gly Arg Ser Asp
1               5                   10                  15

Asn His Gly Gly Gly Ser Gln Val Gln Leu Val Glu Ser Gly Gly Gly
            20                  25                  30

Leu Val Gln Pro Gly Arg Ser Leu Arg Leu Ser Cys Ala Ala Ser Gly
        35                  40                  45

Phe Thr Phe Ser Asn Ala Trp Met His Trp Val Arg Gln Ala Pro Gly
    50                  55                  60

Lys Gly Leu Glu Trp Val Ala Gln Ile Lys Asp Lys Ala Asn Gly Tyr
65                  70                  75                  80

Asn Ala Tyr Tyr Ala Glu Ser Val Lys Gly Arg Phe Thr Ile Ser Arg
                85                  90                  95

Asp Asp Ser Lys Asn Ser Ile Tyr Leu Gln Met Asn Ser Leu Lys Thr
```

100                 105                 110
Glu Asp Thr Ala Val Tyr Tyr Cys Arg Tyr Val His Tyr Thr Thr Tyr
            115                 120                 125

Ala Gly Phe Ser Tyr Lys Phe Gly Val Asp Ala Trp Gly Gln Gly Thr
        130                 135                 140

Thr Val Thr Val Ser Ser
145                 150

<210> SEQ ID NO 76
<211> LENGTH: 159
<212> TYPE: PRT
<213> ORGANISM: Artificial sequence
<220> FEATURE:
<223> OTHER INFORMATION: An artificially synthesized peptide sequence

<400> SEQUENCE: 76

Gln Asp Gly Asn Glu Glu Met Gly Gly Gly Ser Gly Gly Gly Ser Gly
1               5                  10                  15

Gly Gly Ser Leu Ser Gly Arg Ser Asp Asn His Gly Gly Gly Ser Gln
            20                  25                  30

Val Gln Leu Val Glu Ser Gly Gly Gly Leu Val Gln Pro Gly Arg Ser
        35                  40                  45

Leu Arg Leu Ser Cys Ala Ala Ser Gly Phe Thr Phe Ser Asn Ala Trp
    50                  55                  60

Met His Trp Val Arg Gln Ala Pro Gly Lys Gly Leu Glu Trp Val Ala
65                  70                  75                  80

Gln Ile Lys Asp Lys Ala Asn Gly Tyr Asn Ala Tyr Tyr Ala Glu Ser
                85                  90                  95

Val Lys Gly Arg Phe Thr Ile Ser Arg Asp Asp Ser Lys Asn Ser Ile
            100                 105                 110

Tyr Leu Gln Met Asn Ser Leu Lys Thr Glu Asp Thr Ala Val Tyr Tyr
        115                 120                 125

Cys Arg Tyr Val His Tyr Thr Thr Tyr Ala Gly Phe Ser Tyr Lys Phe
    130                 135                 140

Gly Val Asp Ala Trp Gly Gln Gly Thr Thr Val Thr Val Ser Ser
145                 150                 155

<210> SEQ ID NO 77
<211> LENGTH: 160
<212> TYPE: PRT
<213> ORGANISM: Artificial sequence
<220> FEATURE:
<223> OTHER INFORMATION: An artificially synthesized peptide sequence

<400> SEQUENCE: 77

Gln Asp Gly Asn Glu Glu Met Gly Gly Ile Thr Gln Thr Pro Tyr Lys
1               5                  10                  15

Val Ser Ile Ser Leu Ser Gly Arg Ser Asp Asn His Gly Gly Gly Ser
            20                  25                  30

Gln Val Gln Leu Val Glu Ser Gly Gly Gly Leu Val Gln Pro Gly Arg
        35                  40                  45

Ser Leu Arg Leu Ser Cys Ala Ala Ser Gly Phe Thr Phe Ser Asn Ala
    50                  55                  60

Trp Met His Trp Val Arg Gln Ala Pro Gly Lys Gly Leu Glu Trp Val
65                  70                  75                  80

Ala Gln Ile Lys Asp Lys Ala Asn Gly Tyr Asn Ala Tyr Tyr Ala Glu
                85                  90                  95

```
Ser Val Lys Gly Arg Phe Thr Ile Ser Arg Asp Asp Ser Lys Asn Ser
                100                 105                 110

Ile Tyr Leu Gln Met Asn Ser Leu Lys Thr Glu Asp Thr Ala Val Tyr
            115                 120                 125

Tyr Cys Arg Tyr Val His Tyr Thr Thr Tyr Ala Gly Phe Ser Tyr Lys
        130                 135                 140

Phe Gly Val Asp Ala Trp Gly Gln Gly Thr Thr Val Thr Val Ser Ser
145                 150                 155                 160
```

<210> SEQ ID NO 78
<211> LENGTH: 175
<212> TYPE: PRT
<213> ORGANISM: Artificial sequence
<220> FEATURE:
<223> OTHER INFORMATION: An artificially synthesized peptide sequence

<400> SEQUENCE: 78

```
Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
                20                  25                  30

Gly Gly Ser Leu Ser Gly Arg Ser Asp Asn His Gly Gly Ser Gln
            35                  40                  45

Val Gln Leu Val Glu Ser Gly Gly Leu Val Gln Pro Gly Arg Ser
50                  55                  60

Leu Arg Leu Ser Cys Ala Ala Ser Gly Phe Thr Phe Ser Asn Ala Trp
65                  70                  75                  80

Met His Trp Val Arg Gln Ala Pro Gly Lys Gly Leu Glu Trp Val Ala
                85                  90                  95

Gln Ile Lys Asp Lys Ala Asn Gly Tyr Asn Ala Tyr Tyr Ala Glu Ser
                100                 105                 110

Val Lys Gly Arg Phe Thr Ile Ser Arg Asp Asp Ser Lys Asn Ser Ile
            115                 120                 125

Tyr Leu Gln Met Asn Ser Leu Lys Thr Glu Asp Thr Ala Val Tyr Tyr
        130                 135                 140

Cys Arg Tyr Val His Tyr Thr Thr Tyr Ala Gly Phe Ser Tyr Lys Phe
145                 150                 155                 160

Gly Val Asp Ala Trp Gly Gln Gly Thr Thr Val Thr Val Ser Ser
                165                 170                 175
```

<210> SEQ ID NO 79
<211> LENGTH: 163
<212> TYPE: PRT
<213> ORGANISM: Artificial sequence
<220> FEATURE:
<223> OTHER INFORMATION: An artificially synthesized peptide sequence

<400> SEQUENCE: 79

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
                20                  25                  30

Asp Asn His Gln Val Gln Leu Val Glu Ser Gly Gly Gly Leu Val Gln
            35                  40                  45

Pro Gly Arg Ser Leu Arg Leu Ser Cys Ala Ala Ser Gly Phe Thr Phe
        50                  55                  60

Ser Asn Ala Trp Met His Trp Val Arg Gln Ala Pro Gly Lys Gly Leu
65                  70                  75                  80
```

Glu Trp Val Ala Gln Ile Lys Asp Lys Ala Asn Gly Tyr Asn Ala Tyr
            85                  90                  95

Tyr Ala Glu Ser Val Lys Gly Arg Phe Thr Ile Ser Arg Asp Asp Ser
            100                 105                 110

Lys Asn Ser Ile Tyr Leu Gln Met Asn Ser Leu Lys Thr Glu Asp Thr
            115                 120                 125

Ala Val Tyr Tyr Cys Arg Tyr Val His Tyr Thr Thr Tyr Ala Gly Phe
130                 135                 140

Ser Tyr Lys Phe Gly Val Asp Ala Trp Gly Gln Gly Thr Thr Val Thr
145                 150                 155                 160

Val Ser Ser

<210> SEQ ID NO 80
<211> LENGTH: 183
<212> TYPE: PRT
<213> ORGANISM: Artificial sequence
<220> FEATURE:
<223> OTHER INFORMATION: An artificially synthesized peptide sequence

<400> SEQUENCE: 80

Gln Asp Gly Asn Glu Met Gly Gly Ile Thr Gln Thr Pro Tyr Lys
1               5                   10                  15

Val Ser Ile Ser Gly Thr Thr Val Ile Leu Thr Ser Gly Gly Gly
            20                  25                  30

Ser Gly Gly Gly Gly Ser Gly Gly Gly Gly Ser Leu Ser Gly Arg Ser
            35                  40                  45

Asp Asn His Gly Gly Ser Gln Val Gln Leu Val Glu Ser Gly Gly
50                  55                  60

Gly Leu Val Gln Pro Gly Arg Ser Leu Arg Leu Ser Cys Ala Ala Ser
65                  70                  75                  80

Gly Phe Thr Phe Ser Asn Ala Trp Met His Trp Val Arg Gln Ala Pro
            85                  90                  95

Gly Lys Gly Leu Glu Trp Val Ala Gln Ile Lys Asp Lys Ala Asn Gly
            100                 105                 110

Tyr Asn Ala Tyr Tyr Ala Glu Ser Val Lys Gly Arg Phe Thr Ile Ser
            115                 120                 125

Arg Asp Asp Ser Lys Asn Ser Ile Tyr Leu Gln Met Asn Ser Leu Lys
130                 135                 140

Thr Glu Asp Thr Ala Val Tyr Tyr Cys Arg Tyr Val His Tyr Thr Thr
145                 150                 155                 160

Tyr Ala Gly Phe Ser Tyr Lys Phe Gly Val Asp Ala Trp Gly Gln Gly
            165                 170                 175

Thr Thr Val Thr Val Ser Ser
            180

<210> SEQ ID NO 81
<211> LENGTH: 147
<212> TYPE: PRT
<213> ORGANISM: Artificial sequence
<220> FEATURE:
<223> OTHER INFORMATION: An artificially synthesized peptide sequence

<400> SEQUENCE: 81

Gln Asp Gly Asn Glu Gly Gly Gly Ser Pro Leu Gly Leu Ala Gly
1               5                   10                  15

Gly Gly Ser Gln Val Gln Leu Val Glu Ser Gly Gly Gly Leu Val Gln
            20                  25                  30

```
Pro Gly Arg Ser Leu Arg Leu Ser Cys Ala Ala Ser Gly Phe Thr Phe
        35                  40                  45

Ser Asn Ala Trp Met His Trp Val Arg Gln Ala Pro Gly Lys Gly Leu
 50                  55                  60

Glu Trp Val Ala Gln Ile Lys Asp Lys Ala Asn Gly Tyr Asn Ala Tyr
 65                  70                  75                  80

Tyr Ala Glu Ser Val Lys Gly Arg Phe Thr Ile Ser Arg Asp Asp Ser
                85                  90                  95

Lys Asn Ser Ile Tyr Leu Gln Met Asn Ser Leu Lys Thr Glu Asp Thr
                100                 105                 110

Ala Val Tyr Tyr Cys Arg Tyr Val His Tyr Thr Thr Tyr Ala Gly Phe
                115                 120                 125

Ser Tyr Lys Phe Gly Val Asp Ala Trp Gly Gln Gly Thr Thr Val Thr
                130                 135                 140

Val Ser Ser
145

<210> SEQ ID NO 82
<211> LENGTH: 471
<212> TYPE: PRT
<213> ORGANISM: Artificial sequence
<220> FEATURE:
<223> OTHER INFORMATION: An artificially synthesized peptide sequence

<400> SEQUENCE: 82

Gln Asp Gly Asn Glu Gly Gly Ser Gly Gly Ser Gln Val Gln
 1               5                  10                  15

Leu Val Glu Ser Gly Gly Gly Val Val Gln Pro Gly Arg Ser Leu Arg
                20                  25                  30

Leu Ser Cys Ala Ala Ser Gly Phe Thr Phe Ser Asn Ala Trp Met His
                35                  40                  45

Trp Val Arg Gln Ala Pro Gly Lys Gly Leu Glu Trp Val Ala Gln Ile
 50                  55                  60

Lys Ala Lys Ser Asn Asn Tyr Ala Thr Tyr Tyr Ala Glu Ser Val Lys
 65                  70                  75                  80

Gly Arg Phe Thr Ile Ser Arg Asp Asp Ser Lys Asn Ser Leu Tyr Leu
                85                  90                  95

Gln Met Asn Ser Leu Lys Thr Glu Asp Thr Ala Val Tyr Tyr Cys Arg
                100                 105                 110

Tyr Val His Tyr Gly Ala Tyr Tyr Gly Val Asp Ala Trp Gly Gln Gly
                115                 120                 125

Thr Thr Val Thr Val Ser Ser Ala Ser Thr Lys Gly Pro Ser Val Phe
                130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
                195                 200                 205

Ser Ser Leu Gly Thr Gln Thr Tyr Ile Cys Asn Val Asn His Lys Pro
                210                 215                 220

Ser Asn Thr Lys Val Asp Lys Lys Val Glu Pro Lys Ser Cys Asp Lys
225                 230                 235                 240
```

```
Thr His Thr Cys Pro Pro Cys Pro Ala Pro Glu Ala Ala Gly Gly Pro
            245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Cys Glu Leu Thr Lys Asn Gln Val Ser Leu Ser
            370                 375                 380

Cys Ala Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Val Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Asp
            450                 455                 460

Tyr Lys Asp Asp Asp Asp Lys
465                 470

<210> SEQ ID NO 83
<211> LENGTH: 489
<212> TYPE: PRT
<213> ORGANISM: Artificial sequence
<220> FEATURE:
<223> OTHER INFORMATION: An artificially synthesized peptide sequence

<400> SEQUENCE: 83

Gln Asp Gly Asn Glu Glu Met Gly Gly Ser Gly Gly Gly Ser Gly
1               5                   10                  15

Gly Gly Ser Leu Ser Gly Arg Ser Asp Asn His Gly Gly Gly Ser Gln
                20                  25                  30

Val Gln Leu Val Glu Ser Gly Gly Val Val Gln Pro Gly Arg Ser
            35                  40                  45

Leu Arg Leu Ser Cys Ala Ala Ser Gly Phe Thr Phe Ser Asn Ala Trp
            50                  55                  60

Met His Trp Val Arg Gln Ala Pro Gly Lys Gly Leu Glu Trp Val Ala
65                  70                  75                  80

Gln Ile Lys Ala Lys Ser Asn Asn Tyr Ala Thr Tyr Tyr Ala Glu Ser
                85                  90                  95

Val Lys Gly Arg Phe Thr Ile Ser Arg Asp Asp Ser Lys Asn Ser Leu
                100                 105                 110

Tyr Leu Gln Met Asn Ser Leu Lys Thr Glu Asp Thr Ala Val Tyr Tyr
                115                 120                 125
```

Cys Arg Tyr Val His Tyr Gly Ala Tyr Gly Val Asp Ala Trp Gly
            130                 135                 140

Gln Gly Thr Thr Val Thr Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Ala Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
370                 375                 380

Tyr Thr Leu Pro Pro Ser Arg Cys Glu Leu Thr Lys Asn Gln Val Ser
385                 390                 395                 400

Leu Ser Cys Ala Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Val Ser Lys Leu Thr Val
        435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Asp Tyr Lys Asp Asp Asp Lys
                485

<210> SEQ ID NO 84
<211> LENGTH: 490
<212> TYPE: PRT
<213> ORGANISM: Artificial sequence
<220> FEATURE:
<223> OTHER INFORMATION: An artificially synthesized peptide sequence

<400> SEQUENCE: 84

```
Gln Asp Gly Asn Glu Glu Met Gly Gly Ile Thr Gln Thr Pro Tyr Lys
  1               5                  10                  15

Val Ser Ile Ser Leu Ser Gly Arg Ser Asp Asn His Gly Gly Gly Ser
             20                  25                  30

Gln Val Gln Leu Val Glu Ser Gly Gly Val Val Gln Pro Gly Arg
         35                  40                  45

Ser Leu Arg Leu Ser Cys Ala Ala Ser Gly Phe Thr Phe Ser Asn Ala
         50                  55                  60

Trp Met His Trp Val Arg Gln Ala Pro Gly Lys Gly Leu Glu Trp Val
 65                  70                  75                  80

Ala Gln Ile Lys Ala Lys Ser Asn Asn Tyr Ala Thr Tyr Tyr Ala Glu
                 85                  90                  95

Ser Val Lys Gly Arg Phe Thr Ile Ser Arg Asp Asp Ser Lys Asn Ser
                100                 105                 110

Leu Tyr Leu Gln Met Asn Ser Leu Lys Thr Glu Asp Thr Ala Val Tyr
        115                 120                 125

Tyr Cys Arg Tyr Val His Tyr Gly Ala Tyr Gly Val Asp Ala Trp
        130                 135                 140

Gly Gln Gly Thr Thr Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Ala Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Cys Glu Leu Thr Lys Asn Gln Val
385                 390                 395                 400

Ser Leu Ser Cys Ala Val Lys Gly Phe Tyr Pro Ser Asp Ile Ala Val
                405                 410                 415
```

-continued

```
Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Val Ser Lys Leu Thr
            435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro Asp Tyr Lys Asp Asp Asp Lys
                485                 490

<210> SEQ ID NO 85
<211> LENGTH: 505
<212> TYPE: PRT
<213> ORGANISM: Artificial sequence
<220> FEATURE:
<223> OTHER INFORMATION: An artificially synthesized peptide sequence

<400> SEQUENCE: 85

Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
                20                  25                  30

Gly Gly Ser Leu Ser Gly Arg Ser Asp Asn His Gly Gly Ser Gln
            35                  40                  45

Val Gln Leu Val Glu Ser Gly Gly Val Val Gln Pro Gly Arg Ser
    50                  55                  60

Leu Arg Leu Ser Cys Ala Ala Ser Gly Phe Thr Phe Ser Asn Ala Trp
65                  70                  75                  80

Met His Trp Val Arg Gln Ala Pro Gly Lys Gly Leu Glu Trp Val Ala
                85                  90                  95

Gln Ile Lys Ala Lys Ser Asn Asn Tyr Ala Thr Tyr Tyr Ala Glu Ser
                100                 105                 110

Val Lys Gly Arg Phe Thr Ile Ser Arg Asp Asp Ser Lys Asn Ser Leu
            115                 120                 125

Tyr Leu Gln Met Asn Ser Leu Lys Thr Glu Asp Thr Ala Val Tyr Tyr
    130                 135                 140

Cys Arg Tyr Val His Tyr Gly Ala Tyr Gly Val Asp Ala Trp Gly
145                 150                 155                 160

Gln Gly Thr Thr Val Thr Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
    195                 200                 205

Ser Trp Asn Ser Gly Ala Leu Thr Ser Gly Val His Thr Phe Pro Ala
210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Val Glu Pro Lys Ser Cys
            260                 265                 270

Asp Lys Thr His Thr Cys Pro Pro Cys Pro Ala Pro Glu Ala Ala Gly
    275                 280                 285
```

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Ala Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Cys Glu Leu Thr Lys Asn Gln Val Ser
                405                 410                 415

Leu Ser Cys Ala Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Val Ser Lys Leu Thr Val
450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Asp Tyr Lys Asp Asp Asp Lys
            500                 505

<210> SEQ ID NO 86
<211> LENGTH: 493
<212> TYPE: PRT
<213> ORGANISM: Artificial sequence
<220> FEATURE:
<223> OTHER INFORMATION: An artificially synthesized peptide sequence

<400> SEQUENCE: 86

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30

Asp Asn His Gln Val Gln Leu Val Glu Ser Gly Gly Gly Val Val Gln
        35                  40                  45

Pro Gly Arg Ser Leu Arg Leu Ser Cys Ala Ala Ser Gly Phe Thr Phe
    50                  55                  60

Ser Asn Ala Trp Met His Trp Val Arg Gln Ala Pro Gly Lys Gly Leu
65                  70                  75                  80

Glu Trp Val Ala Gln Ile Lys Ala Lys Ser Asn Asn Tyr Ala Thr Tyr
                85                  90                  95

Tyr Ala Glu Ser Val Lys Gly Arg Phe Thr Ile Ser Arg Asp Asp Ser
            100                 105                 110

Lys Asn Ser Leu Tyr Leu Gln Met Asn Ser Leu Lys Thr Glu Asp Thr
        115                 120                 125

Ala Val Tyr Tyr Cys Arg Tyr Val His Tyr Gly Ala Tyr Tyr Gly Val
    130                 135                 140

```
Asp Ala Trp Gly Gln Gly Thr Thr Val Thr Val Ser Ser Ala Ser Thr
145                 150                 155                 160

Lys Gly Pro Ser Val Phe Pro Leu Ala Pro Ser Ser Lys Ser Thr Ser
            165                 170                 175

Gly Gly Thr Ala Ala Leu Gly Cys Leu Val Lys Asp Tyr Phe Pro Glu
                180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
            245                 250                 255

Pro Lys Ser Cys Asp Lys Thr His Thr Cys Pro Pro Cys Pro Ala Pro
                260                 265                 270

Glu Ala Ala Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Ala Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Cys Glu Leu Thr Lys
385                 390                 395                 400

Asn Gln Val Ser Leu Ser Cys Ala Val Lys Gly Phe Tyr Pro Ser Asp
            405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Val Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Asp Tyr Lys Asp Asp Asp Lys
                485                 490

<210> SEQ ID NO 87
<211> LENGTH: 477
<212> TYPE: PRT
<213> ORGANISM: Artificial sequence
<220> FEATURE:
<223> OTHER INFORMATION: An artificially synthesized peptide sequence

<400> SEQUENCE: 87

Gln Asp Gly Asn Glu Gly Gly Gly Ser Pro Leu Gly Leu Ala Gly
1               5                   10                  15
```

```
Gly Gly Ser Gln Val Gln Leu Val Glu Ser Gly Gly Val Val Gln
             20              25              30
Pro Gly Arg Ser Leu Arg Leu Ser Cys Ala Ala Ser Gly Phe Thr Phe
         35                  40                  45
Ser Asn Ala Trp Met His Trp Val Arg Gln Ala Pro Gly Lys Gly Leu
 50                  55                  60
Glu Trp Val Ala Gln Ile Lys Ala Lys Ser Asn Asn Tyr Ala Thr Tyr
 65                  70                  75                  80
Tyr Ala Glu Ser Val Lys Gly Arg Phe Thr Ile Ser Arg Asp Asp Ser
                 85                  90                  95
Lys Asn Ser Leu Tyr Leu Gln Met Asn Ser Leu Lys Thr Glu Asp Thr
                100                 105                 110
Ala Val Tyr Tyr Cys Arg Tyr Val His Tyr Gly Ala Tyr Tyr Gly Val
            115                 120                 125
Asp Ala Trp Gly Gln Gly Thr Thr Val Thr Val Ser Ser Ala Ser Thr
130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
        195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Ala Ala Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Ala Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Cys Glu Leu Thr Lys
    370                 375                 380
Asn Gln Val Ser Leu Ser Cys Ala Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Val Ser
            420                 425                 430
Lys Leu Thr Val Asp Lys Ser Arg Trp Gln Gln Gly Asn Val Phe Ser
```

```
                    435                 440                 445
Cys Ser Val Met His Glu Ala Leu His Asn His Tyr Thr Gln Lys Ser
            450                 455                 460

Leu Ser Leu Ser Pro Asp Tyr Lys Asp Asp Asp Lys
465                 470                 475

<210> SEQ ID NO 88
<211> LENGTH: 236
<212> TYPE: PRT
<213> ORGANISM: Artificial sequence
<220> FEATURE:
<223> OTHER INFORMATION: An artificially synthesized peptide sequence

<400> SEQUENCE: 88

Gln Asp Gly Asn Glu Gly Gly Ser Gly Gly Gly Ser Gly Gly Gly
1               5                   10                  15

Ser Asp Ile Val Met Thr Gln Ser Pro Leu Ser Leu Pro Val Thr Pro
                20                  25                  30

Gly Glu Pro Ala Ser Ile Ser Cys Arg Ser Ser Gln Ser Leu Val His
            35                  40                  45

Ser Asn Arg Asn Thr Tyr Leu His Trp Tyr Gln Gln Lys Pro Gly Gln
    50                  55                  60

Ala Pro Arg Leu Leu Ile Tyr Lys Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 89
<211> LENGTH: 236
<212> TYPE: PRT
<213> ORGANISM: Artificial sequence
<220> FEATURE:
<223> OTHER INFORMATION: An artificially synthesized peptide sequence

<400> SEQUENCE: 89

Gln Asp Gly Asn Glu Leu Ser Gly Arg Ser Asp Asn His Gly Gly Gly
1               5                   10                  15

Ser Asp Ile Val Met Thr Gln Ser Pro Leu Ser Leu Pro Val Thr Pro
                20                  25                  30
```

```
Gly Glu Pro Ala Ser Ile Ser Cys Arg Ser Ser Gln Ser Leu Val His
             35                  40                  45

Ser Asn Arg Asn Thr Tyr Leu His Trp Tyr Gln Gln Lys Pro Gly Gln
 50                  55                  60

Ala Pro Arg Leu Leu Ile Tyr Lys Val Ser Asn Arg Phe Ser Gly Val
 65                  70                  75                  80

Pro Asp Arg Phe Ser Gly Ser Gly Ser Gly Thr Asp Phe Thr Leu Lys
                 85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 90
<211> LENGTH: 250
<212> TYPE: PRT
<213> ORGANISM: Artificial sequence
<220> FEATURE:
<223> OTHER INFORMATION: An artificially synthesized peptide sequence

<400> SEQUENCE: 90

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Asp
            20                  25                  30

Ile Val Met Thr Gln Ser Pro Leu Ser Leu Pro Val Thr Pro Gly Glu
            35                  40                  45

Pro Ala Ser Ile Ser Cys Arg Ser Ser Gln Ser Leu Val His Ser Asn
 50                  55                  60

Arg Asn Thr Tyr Leu His Trp Tyr Gln Gln Lys Pro Gly Gln Ala Pro
 65                  70                  75                  80

Arg Leu Leu Ile Tyr Lys Val Ser Asn Arg Phe Ser Gly Val Pro Asp
                 85                  90                  95

Arg Phe Ser Gly Ser Gly Ser Gly Thr Asp Phe Thr Leu Lys Ile Ser
            100                 105                 110

Arg Val Glu Ala Glu Asp Val Gly Val Tyr Tyr Cys Gly Gln Gly Thr
            115                 120                 125

Gln Val Pro Tyr Thr Phe Gly Gln Gly Thr Lys Leu Glu Ile Lys Arg
        130                 135                 140

Thr Val Ala Ala Pro Ser Val Phe Ile Phe Pro Pro Ser Asp Glu Gln
145                 150                 155                 160
```

Leu Lys Ser Gly Thr Ala Ser Val Val Cys Leu Leu Asn Asn Phe Tyr
            165                 170                 175

Pro Arg Glu Ala Lys Val Gln Trp Lys Val Asp Asn Ala Leu Gln Ser
        180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
            245                 250

<210> SEQ ID NO 91
<211> LENGTH: 266
<212> TYPE: PRT
<213> ORGANISM: Artificial sequence
<220> FEATURE:
<223> OTHER INFORMATION: An artificially synthesized peptide sequence

<400> SEQUENCE: 91

Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
            20                  25                  30

Gly Gly Ser Leu Ser Gly Arg Ser Asp Asn His Gly Gly Ser Asp
            35                  40                  45

Ile Val Met Thr Gln Ser Pro Leu Ser Leu Pro Val Thr Pro Gly Glu
    50                  55                  60

Pro Ala Ser Ile Ser Cys Arg Ser Ser Gln Ser Leu Val His Ser Asn
65                  70                  75                  80

Arg Asn Thr Tyr Leu His Trp Tyr Gln Gln Lys Pro Gly Gln Ala Pro
                85                  90                  95

Arg Leu Leu Ile Tyr Lys Val Ser Asn Arg Phe Ser Gly Val Pro Asp
            100                 105                 110

Arg Phe Ser Gly Ser Gly Ser Gly Thr Asp Phe Thr Leu Lys Ile Ser
        115                 120                 125

Arg Val Glu Ala Glu Asp Val Gly Val Tyr Tyr Cys Gly Gln Gly Thr
    130                 135                 140

Gln Val Pro Tyr Thr Phe Gly Gln Gly Thr Lys Leu Glu Ile Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205

Gly Asn Ser Gln Glu Ser Val Thr Glu Gln Asp Ser Lys Asp Ser Thr
    210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

```
<210> SEQ ID NO 92
<211> LENGTH: 254
<212> TYPE: PRT
<213> ORGANISM: Artificial sequence
<220> FEATURE:
<223> OTHER INFORMATION: An artificially synthesized peptide sequence

<400> SEQUENCE: 92

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30

Asp Asn His Asp Ile Val Met Thr Gln Ser Pro Leu Ser Leu Pro Val
        35                  40                  45

Thr Pro Gly Glu Pro Ala Ser Ile Ser Cys Arg Ser Ser Gln Ser Leu
    50                  55                  60

Val His Ser Asn Arg Asn Thr Tyr Leu His Trp Tyr Gln Gln Lys Pro
65                  70                  75                  80

Gly Gln Ala Pro Arg Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Val Gly Val Tyr Tyr Cys
        115                 120                 125

Gly Gln Gly Thr Gln Val Pro Tyr Thr Phe Gly Gln Gly Thr Lys Leu
    130                 135                 140

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
        195                 200                 205

Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250

<210> SEQ ID NO 93
<211> LENGTH: 238
<212> TYPE: PRT
<213> ORGANISM: Artificial sequence
<220> FEATURE:
<223> OTHER INFORMATION: An artificially synthesized peptide sequence

<400> SEQUENCE: 93

Gln Asp Gly Asn Glu Gly Gly Gly Ser Pro Leu Gly Leu Ala Gly
1               5                   10                  15

Gly Gly Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Val His Ser Asn Arg Asn Thr Tyr Leu His Trp Tyr Gln Gln Lys Pro
    50                  55                  60
```

```
Gly Gln Ala Pro Arg Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Val Gly Val Tyr Tyr Cys
            100                 105                 110

Gly Gln Gly Thr Gln Val Pro Tyr Thr Phe Gly Gln Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 94
<211> LENGTH: 236
<212> TYPE: PRT
<213> ORGANISM: Artificial sequence
<220> FEATURE:
<223> OTHER INFORMATION: An artificially synthesized peptide sequence

<400> SEQUENCE: 94

Gln Asp Gly Asn Glu Gly Gly Ser Gly Gly Gly Ser Gly Gly Gly Gly
1               5                   10                  15

Ser Asp Ile Val Met Thr Gln Ser Pro Leu Ser Leu Pro Val Thr Pro
            20                  25                  30

Gly Glu Pro Ala Ser Ile Ser Cys Arg Ser Ser Gln Ser Leu Val His
        35                  40                  45

Ser Asn Arg Asn Thr Tyr Leu His Trp Tyr Gln Gln Lys Pro Gly Gln
    50                  55                  60

Ala Pro Arg Leu Leu Ile Tyr Lys Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Val Gly Val Tyr Tyr Cys Gly Gln
            100                 105                 110

Gly Thr Gln Val Pro Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190
```

Ser Thr Tyr Ser Leu Ser Ser Thr Leu Thr Leu Ser Lys Ala Asp Tyr
         195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 95
<211> LENGTH: 251
<212> TYPE: PRT
<213> ORGANISM: Artificial sequence
<220> FEATURE:
<223> OTHER INFORMATION: An artificially synthesized peptide sequence

<400> SEQUENCE: 95

Gln Asp Gly Asn Glu Met Gly Gly Ile Thr Gln Thr Pro Tyr Lys
1               5                   10                  15

Val Ser Ile Ser Leu Ser Gly Arg Ser Asp Asn His Gly Gly Ser
            20                  25                  30

Asp Ile Val Met Thr Gln Ser Pro Leu Ser Leu Pro Val Thr Pro Gly
        35                  40                  45

Glu Pro Ala Ser Ile Ser Cys Arg Ser Ser Gln Ser Leu Val His Ser
    50                  55                  60

Asn Arg Asn Thr Tyr Leu His Trp Tyr Gln Gln Lys Pro Gly Gln Ala
65                  70                  75                  80

Pro Arg Leu Leu Ile Tyr Lys Val Ser Asn Arg Phe Ser Gly Val Pro
                85                  90                  95

Asp Arg Phe Ser Gly Ser Gly Ser Gly Thr Asp Phe Thr Leu Lys Ile
            100                 105                 110

Ser Arg Val Glu Ala Glu Asp Val Gly Val Tyr Tyr Cys Gly Gln Gly
        115                 120                 125

Thr Gln Val Pro Tyr Thr Phe Gly Gln Gly Thr Lys Leu Glu Ile Lys
    130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 96
<211> LENGTH: 238
<212> TYPE: PRT
<213> ORGANISM: Artificial sequence
<220> FEATURE:
<223> OTHER INFORMATION: An artificially synthesized peptide sequence

<400> SEQUENCE: 96

Gln Asp Gly Asn Glu Gly Gly Gly Gly Ser Pro Leu Gly Leu Ala Gly

```
1               5                   10                  15
Gly Gly Ser Asp Ile Val Met Thr Gln Ser Pro Leu Ser Leu Pro Val
            20                  25                  30
Thr Pro Gly Glu Pro Ala Ser Ile Ser Cys Arg Ser Ser Gln Ser Leu
            35                  40                  45
Val His Ser Asn Arg Asn Thr Tyr Leu His Trp Tyr Gln Gln Lys Pro
50                  55                  60
Gly Gln Ala Pro Arg Leu Leu Ile Tyr Lys Val Ser Asn Arg Phe Ser
65                  70                  75                  80
Gly Val Pro Asp Arg Phe Ser Gly Ser Gly Ser Gly Thr Asp Phe Thr
            85                  90                  95
Leu Lys Ile Ser Arg Val Glu Ala Glu Asp Val Gly Val Tyr Tyr Cys
            100                 105                 110
Gly Gln Gly Thr Gln Val Pro Tyr Thr Phe Gly Gln Gly Thr Lys Leu
            115                 120                 125
Glu Ile Lys Arg Thr Val Ala Ala Pro Ser Val Phe Ile Phe Pro Pro
            130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
            165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
            195                 200                 205
Asp Tyr Glu Lys His Lys Val Tyr Ala Cys Glu Val Thr His Gln Gly
            210                 215                 220
Leu Ser Ser Pro Val Thr Lys Ser Phe Asn Arg Gly Glu Cys
225                 230                 235
```

<210> SEQ ID NO 97
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 97

```
Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Ser Asn Ala
            20                  25                  30
Trp Met His Trp Val Arg Gln Ala Pro Gly Lys Gly Leu Glu Trp Val
            35                  40                  45
Ala Gln Ile Lys Asp Lys Ala Asn Gly Tyr Asn Ala Tyr Tyr Ala Glu
50                  55                  60
Ser Val Lys Gly Arg Phe Thr Ile Ser Arg Asp Asp Ser Lys Asn Ser
65                  70                  75                  80
Ile Tyr Leu Gln Met Asn Ser Leu Lys Thr Glu Asp Thr Ala Val Tyr
            85                  90                  95
Tyr Cys Arg Tyr Val His Tyr Thr Thr Tyr Ala Gly Phe Ser Tyr Lys
            100                 105                 110
Phe Gly Val Asp Ala Trp Gly Gln Gly Thr Thr Val Thr Val Ser Ser
            115                 120                 125
Ala Ser Thr Lys Gly Pro Ser Val Phe Pro Leu Ala Pro Ser Ser Lys
```

```
                130                 135                 140
Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Cys Glu
            355                 360                 365

Leu Thr Lys Asn Gln Val Ser Leu Ser Cys Ala Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Asp Tyr Lys Asp Asp Asp Asp Lys
        450                 455                 460

<210> SEQ ID NO 98
<211> LENGTH: 477
<212> TYPE: PRT
<213> ORGANISM: Artificial sequence
<220> FEATURE:
<223> OTHER INFORMATION: An artificially synthesized peptide sequence

<400> SEQUENCE: 98

Gln Asp Gly Asn Glu Gly Gly Gly Ser Gly Gly Gly Ser Gln Val Gln
1               5                   10                  15

Leu Val Glu Ser Gly Gly Gly Leu Val Gln Pro Gly Arg Ser Leu Arg
            20                  25                  30

Leu Ser Cys Ala Ala Ser Gly Phe Thr Phe Ser Asn Ala Trp Met His
```

```
              35                  40                  45
Trp Val Arg Gln Ala Pro Gly Lys Gly Leu Glu Trp Val Ala Gln Ile
 50                  55                  60
Lys Asp Lys Ala Asn Gly Tyr Asn Ala Tyr Tyr Ala Glu Ser Val Lys
 65                  70                  75                  80
Gly Arg Phe Thr Ile Ser Arg Asp Asp Ser Lys Asn Ser Ile Tyr Leu
                     85                  90                  95
Gln Met Asn Ser Leu Lys Thr Glu Asp Thr Ala Val Tyr Tyr Cys Arg
                    100                 105                 110
Tyr Val His Tyr Thr Thr Tyr Ala Gly Phe Ser Tyr Lys Phe Gly Val
                115                 120                 125
Asp Ala Trp Gly Gln Gly Thr Thr Val Thr Val Ser Ser Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                    165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                    245                 250                 255
Glu Ala Ala Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Ala Ser Thr Tyr Arg Val Val Ser Val Leu Thr Val Leu His Gln Asp
                    325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Cys Glu Leu Thr Lys
        370                 375                 380
Asn Gln Val Ser Leu Ser Cys Ala Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Val Ser
                420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
450                 455                 460
```

```
Leu Ser Leu Ser Pro Asp Tyr Lys Asp Asp Asp Lys
465                 470                 475
```

<210> SEQ ID NO 99
<211> LENGTH: 486
<212> TYPE: PRT
<213> ORGANISM: Artificial sequence
<220> FEATURE:
<223> OTHER INFORMATION: An artificially synthesized peptide sequence

<400> SEQUENCE: 99

```
Gln Asp Gly Asn Glu Gly Gly Gly Ser Leu Ser Gly Arg Ser Asp
1               5                   10                  15

Asn His Gly Gly Gly Ser Gln Val Gln Leu Val Glu Ser Gly Gly Gly
                20                  25                  30

Leu Val Gln Pro Gly Arg Ser Leu Arg Leu Ser Cys Ala Ala Ser Gly
            35                  40                  45

Phe Thr Phe Ser Asn Ala Trp Met His Trp Val Arg Gln Ala Pro Gly
50                  55                  60

Lys Gly Leu Glu Trp Val Ala Gln Ile Lys Asp Lys Ala Asn Gly Tyr
65                  70                  75                  80

Asn Ala Tyr Tyr Ala Glu Ser Val Lys Gly Arg Phe Thr Ile Ser Arg
                85                  90                  95

Asp Asp Ser Lys Asn Ser Ile Tyr Leu Gln Met Asn Ser Leu Lys Thr
            100                 105                 110

Glu Asp Thr Ala Val Tyr Tyr Cys Arg Tyr Val His Tyr Thr Thr Tyr
        115                 120                 125

Ala Gly Phe Ser Tyr Lys Phe Gly Val Asp Ala Trp Gly Gln Gly Thr
    130                 135                 140

Thr Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Lys Val Glu Pro Lys Ser Cys Asp Lys Thr
                245                 250                 255

His Thr Cys Pro Pro Cys Pro Ala Pro Glu Ala Ala Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Ala Ser Thr Tyr Arg Val Val
                325                 330                 335

Ser Val Leu Thr Val Leu His Gln Asp Trp Leu Asn Gly Lys Glu Tyr
            340                 345                 350
```

```
Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
        370                 375                 380

Pro Pro Ser Arg Cys Glu Leu Thr Lys Asn Gln Val Ser Leu Ser Cys
385                 390                 395                 400

Ala Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Val Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Asp Tyr
465                 470                 475                 480

Lys Asp Asp Asp Lys
                485

<210> SEQ ID NO 100
<211> LENGTH: 495
<212> TYPE: PRT
<213> ORGANISM: Artificial sequence
<220> FEATURE:
<223> OTHER INFORMATION: An artificially synthesized peptide sequence

<400> SEQUENCE: 100

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Gln
            20                  25                  30

Val Gln Leu Val Glu Ser Gly Gly Gly Leu Val Gln Pro Gly Arg Ser
        35                  40                  45

Leu Arg Leu Ser Cys Ala Ala Ser Gly Phe Thr Phe Ser Asn Ala Trp
    50                  55                  60

Met His Trp Val Arg Gln Ala Pro Gly Lys Gly Leu Glu Trp Val Ala
65                  70                  75                  80

Gln Ile Lys Asp Lys Ala Asn Gly Tyr Asn Ala Tyr Tyr Ala Glu Ser
                85                  90                  95

Val Lys Gly Arg Phe Thr Ile Ser Arg Asp Asp Ser Lys Asn Ser Ile
            100                 105                 110

Tyr Leu Gln Met Asn Ser Leu Lys Thr Glu Asp Thr Ala Val Tyr Tyr
        115                 120                 125

Cys Arg Tyr Val His Tyr Thr Thr Tyr Ala Gly Phe Ser Tyr Lys Phe
    130                 135                 140

Gly Val Asp Ala Trp Gly Gln Gly Thr Thr Val Thr Val Ser Ser Ala
145                 150                 155                 160

Ser Thr Lys Gly Pro Ser Val Phe Pro Leu Ala Pro Ser Ser Lys Ser
                165                 170                 175

Thr Ser Gly Gly Thr Ala Ala Leu Gly Cys Leu Val Lys Asp Tyr Phe
            180                 185                 190

Pro Glu Pro Val Thr Val Ser Trp Asn Ser Gly Ala Leu Thr Ser Gly
        195                 200                 205

Val His Thr Phe Pro Ala Val Leu Gln Ser Ser Gly Leu Tyr Ser Leu
    210                 215                 220
```

```
Ser Ser Val Val Thr Val Pro Ser Ser Leu Gly Thr Gln Thr Tyr
225                 230                 235                 240

Ile Cys Asn Val Asn His Lys Pro Ser Asn Thr Lys Val Asp Lys Lys
            245                 250                 255

Val Glu Pro Lys Ser Cys Asp Lys Thr His Thr Cys Pro Pro Cys Pro
        260                 265                 270

Ala Pro Glu Ala Ala Gly Gly Pro Ser Val Phe Leu Phe Pro Pro Lys
        275                 280                 285

Pro Lys Asp Thr Leu Met Ile Ser Arg Thr Pro Glu Val Thr Cys Val
        290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Ala Ser Thr Tyr Arg Val Val Ser Val Leu Thr Val Leu His
        340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Cys Glu Leu
385                 390                 395                 400

Thr Lys Asn Gln Val Ser Leu Ser Cys Ala Val Lys Gly Phe Tyr Pro
            405                 410                 415

Ser Asp Ile Ala Val Glu Trp Glu Ser Asn Gly Gln Pro Glu Asn Asn
        420                 425                 430

Tyr Lys Thr Thr Pro Pro Val Leu Asp Ser Asp Gly Ser Phe Phe Leu
        435                 440                 445

Val Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Asp Tyr Lys Asp Asp Asp Lys
            485                 490                 495

<210> SEQ ID NO 101
<211> LENGTH: 496
<212> TYPE: PRT
<213> ORGANISM: Artificial sequence
<220> FEATURE:
<223> OTHER INFORMATION: An artificially synthesized peptide sequence

<400> SEQUENCE: 101

Gln Asp Gly Asn Glu Glu Met Gly Gly Ile Thr Gln Thr Pro Tyr Lys
1               5                   10                  15

Val Ser Ile Ser Leu Ser Gly Arg Ser Asp Asn His Gly Gly Gly Ser
            20                  25                  30

Gln Val Gln Leu Val Glu Ser Gly Gly Gly Leu Val Gln Pro Gly Arg
        35                  40                  45

Ser Leu Arg Leu Ser Cys Ala Ala Ser Gly Phe Thr Phe Ser Asn Ala
    50                  55                  60

Trp Met His Trp Val Arg Gln Ala Pro Gly Lys Gly Leu Glu Trp Val
65                  70                  75                  80

Ala Gln Ile Lys Asp Lys Ala Asn Gly Tyr Asn Ala Tyr Tyr Ala Glu
            85                  90                  95
```

Ser Val Lys Gly Arg Phe Thr Ile Ser Arg Asp Asp Ser Lys Asn Ser
            100                 105                 110

Ile Tyr Leu Gln Met Asn Ser Leu Lys Thr Glu Asp Thr Ala Val Tyr
            115                 120                 125

Tyr Cys Arg Tyr Val His Tyr Thr Thr Tyr Ala Gly Phe Ser Tyr Lys
            130                 135                 140

Phe Gly Val Asp Ala Trp Gly Gln Gly Thr Thr Val Thr Val Ser Ser
145                 150                 155                 160

Ala Ser Thr Lys Gly Pro Ser Val Phe Pro Leu Ala Pro Ser Ser Lys
            165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
            195                 200                 205

Gly Val His Thr Phe Pro Ala Val Leu Gln Ser Ser Gly Leu Tyr Ser
            210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
            245                 250                 255

Lys Val Glu Pro Lys Ser Cys Asp Lys Thr His Thr Cys Pro Pro Cys
            260                 265                 270

Pro Ala Pro Glu Ala Ala Gly Gly Pro Ser Val Phe Leu Phe Pro Pro
            275                 280                 285

Lys Pro Lys Asp Thr Leu Met Ile Ser Arg Thr Pro Glu Val Thr Cys
            290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
            325                 330                 335

Glu Gln Tyr Ala Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
            370                 375                 380

Gln Pro Arg Glu Pro Gln Val Tyr Thr Leu Pro Pro Ser Arg Cys Glu
385                 390                 395                 400

Leu Thr Lys Asn Gln Val Ser Leu Ser Cys Ala Val Lys Gly Phe Tyr
            405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
            435                 440                 445

Leu Val Ser Lys Leu Thr Val Asp Lys Ser Arg Trp Gln Gln Gly Asn
            450                 455                 460

Val Phe Ser Cys Ser Val Met His Glu Ala Leu His Asn His Tyr Thr
465                 470                 475                 480

Gln Lys Ser Leu Ser Leu Ser Pro Asp Tyr Lys Asp Asp Asp Asp Lys
            485                 490                 495

<210> SEQ ID NO 102
<211> LENGTH: 511

```
<212> TYPE: PRT
<213> ORGANISM: Artificial sequence
<220> FEATURE:
<223> OTHER INFORMATION: An artificially synthesized peptide sequence

<400> SEQUENCE: 102
```

Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
            20                  25                  30

Gly Gly Ser Leu Ser Gly Arg Ser Asp Asn His Gly Gly Gly Ser Gln
            35                  40                  45

Val Gln Leu Val Glu Ser Gly Gly Leu Val Gln Pro Gly Arg Ser
50                  55                  60

Leu Arg Leu Ser Cys Ala Ala Ser Gly Phe Thr Phe Ser Asn Ala Trp
65                  70                  75                  80

Met His Trp Val Arg Gln Ala Pro Gly Lys Gly Leu Glu Trp Val Ala
                85                  90                  95

Gln Ile Lys Asp Lys Ala Asn Gly Tyr Asn Ala Tyr Ala Glu Ser
                100                 105                 110

Val Lys Gly Arg Phe Thr Ile Ser Arg Asp Asp Ser Lys Asn Ser Ile
                115                 120                 125

Tyr Leu Gln Met Asn Ser Leu Lys Thr Glu Asp Thr Ala Val Tyr Tyr
130                 135                 140

Cys Arg Tyr Val His Tyr Thr Thr Tyr Ala Gly Phe Ser Tyr Lys Phe
145                 150                 155                 160

Gly Val Asp Ala Trp Gly Gln Gly Thr Thr Val Thr Val Ser Ser Ala
                165                 170                 175

Ser Thr Lys Gly Pro Ser Val Phe Pro Leu Ala Pro Ser Ser Lys Ser
                180                 185                 190

Thr Ser Gly Gly Thr Ala Ala Leu Gly Cys Leu Val Lys Asp Tyr Phe
                195                 200                 205

Pro Glu Pro Val Thr Val Ser Trp Asn Ser Gly Ala Leu Thr Ser Gly
210                 215                 220

Val His Thr Phe Pro Ala Val Leu Gln Ser Ser Gly Leu Tyr Ser Leu
225                 230                 235                 240

Ser Ser Val Val Thr Val Pro Ser Ser Leu Gly Thr Gln Thr Tyr
                245                 250                 255

Ile Cys Asn Val Asn His Lys Pro Ser Asn Thr Lys Val Asp Lys Lys
                260                 265                 270

Val Glu Pro Lys Ser Cys Asp Lys Thr His Thr Cys Pro Pro Cys Pro
                275                 280                 285

Ala Pro Glu Ala Ala Gly Gly Pro Ser Val Phe Leu Phe Pro Pro Lys
                290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
                340                 345                 350

Gln Tyr Ala Ser Thr Tyr Arg Val Val Ser Val Leu Thr Val Leu His
                355                 360                 365

Gln Asp Trp Leu Asn Gly Lys Glu Tyr Lys Cys Lys Val Ser Asn Lys
370                 375                 380

```
Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Cys Glu Leu
            405                 410                 415

Thr Lys Asn Gln Val Ser Leu Ser Cys Ala Val Lys Gly Phe Tyr Pro
        420                 425                 430

Ser Asp Ile Ala Val Glu Trp Glu Ser Asn Gly Gln Pro Glu Asn Asn
    435                 440                 445

Tyr Lys Thr Thr Pro Pro Val Leu Asp Ser Asp Gly Ser Phe Phe Leu
450                 455                 460

Val Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
            485                 490                 495

Lys Ser Leu Ser Leu Ser Pro Asp Tyr Lys Asp Asp Asp Lys
                500                 505                 510

<210> SEQ ID NO 103
<211> LENGTH: 499
<212> TYPE: PRT
<213> ORGANISM: Artificial sequence
<220> FEATURE:
<223> OTHER INFORMATION: An artificially synthesized peptide sequence

<400> SEQUENCE: 103

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
                20                  25                  30

Asp Asn His Gln Val Gln Leu Val Glu Ser Gly Gly Gly Leu Val Gln
            35                  40                  45

Pro Gly Arg Ser Leu Arg Leu Ser Cys Ala Ala Ser Gly Phe Thr Phe
    50                  55                  60

Ser Asn Ala Trp Met His Trp Val Arg Gln Ala Pro Gly Lys Gly Leu
65                  70                  75                  80

Glu Trp Val Ala Gln Ile Lys Asp Lys Ala Asn Gly Tyr Asn Ala Tyr
                85                  90                  95

Tyr Ala Glu Ser Val Lys Gly Arg Phe Thr Ile Ser Arg Asp Asp Ser
            100                 105                 110

Lys Asn Ser Ile Tyr Leu Gln Met Asn Ser Leu Lys Thr Glu Asp Thr
        115                 120                 125

Ala Val Tyr Tyr Cys Arg Tyr Val His Tyr Thr Thr Tyr Ala Gly Phe
    130                 135                 140

Ser Tyr Lys Phe Gly Val Asp Ala Trp Gly Gln Gly Thr Thr Val Thr
145                 150                 155                 160

Val Ser Ser Ala Ser Thr Lys Gly Pro Ser Val Phe Pro Leu Ala Pro
                165                 170                 175

Ser Ser Lys Ser Thr Ser Gly Gly Thr Ala Ala Leu Gly Cys Leu Val
            180                 185                 190

Lys Asp Tyr Phe Pro Glu Pro Val Thr Val Ser Trp Asn Ser Gly Ala
        195                 200                 205

Leu Thr Ser Gly Val His Thr Phe Pro Ala Val Leu Gln Ser Ser Gly
    210                 215                 220

Leu Tyr Ser Leu Ser Ser Val Val Thr Val Pro Ser Ser Ser Leu Gly
225                 230                 235                 240
```

Thr Gln Thr Tyr Ile Cys Asn Val Asn His Lys Pro Ser Asn Thr Lys
                245                 250                 255

Val Asp Lys Lys Val Glu Pro Lys Ser Cys Asp Lys Thr His Thr Cys
        260                 265                 270

Pro Pro Cys Pro Ala Pro Glu Ala Ala Gly Gly Pro Ser Val Phe Leu
            275                 280                 285

Phe Pro Pro Lys Pro Lys Asp Thr Leu Met Ile Ser Arg Thr Pro Glu
        290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Ala Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Cys Glu Leu Thr Lys Asn Gln Val Ser Leu Ser Cys Ala Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Val Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Asp Tyr Lys Asp Asp
                485                 490                 495

Asp Asp Lys

<210> SEQ ID NO 104
<211> LENGTH: 519
<212> TYPE: PRT
<213> ORGANISM: Artificial sequence
<220> FEATURE:
<223> OTHER INFORMATION: An artificially synthesized peptide sequence

<400> SEQUENCE: 104

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Ser Gly Gly Gly Gly
            20                  25                  30

Ser Gly Gly Gly Gly Ser Gly Gly Gly Gly Ser Leu Ser Gly Arg Ser
        35                  40                  45

Asp Asn His Gly Gly Gly Ser Gln Val Gln Leu Val Glu Ser Gly Gly
    50                  55                  60

Gly Leu Val Gln Pro Gly Arg Ser Leu Arg Leu Ser Cys Ala Ala Ser
65                  70                  75                  80

Gly Phe Thr Phe Ser Asn Ala Trp Met His Trp Val Arg Gln Ala Pro
                85                  90                  95

Gly Lys Gly Leu Glu Trp Val Ala Gln Ile Lys Asp Lys Ala Asn Gly

```
                100             105             110
Tyr Asn Ala Tyr Tyr Ala Glu Ser Val Lys Gly Arg Phe Thr Ile Ser
            115             120             125

Arg Asp Asp Ser Lys Asn Ser Ile Tyr Leu Gln Met Asn Ser Leu Lys
130             135             140

Thr Glu Asp Thr Ala Val Tyr Tyr Cys Arg Tyr Val His Tyr Thr Thr
145             150             155             160

Tyr Ala Gly Phe Ser Tyr Lys Phe Gly Val Asp Ala Trp Gly Gln Gly
            165             170             175

Thr Thr Val Thr Val Ser Ser Ala Ser Thr Lys Gly Pro Ser Val Phe
            180             185             190

Pro Leu Ala Pro Ser Ser Lys Ser Thr Ser Gly Gly Thr Ala Ala Leu
            195             200             205

Gly Cys Leu Val Lys Asp Tyr Phe Pro Glu Pro Val Thr Val Ser Trp
            210             215             220

Asn Ser Gly Ala Leu Thr Ser Gly Val His Thr Phe Pro Ala Val Leu
225             230             235             240

Gln Ser Ser Gly Leu Tyr Ser Leu Ser Ser Val Val Thr Val Pro Ser
            245             250             255

Ser Ser Leu Gly Thr Gln Thr Tyr Ile Cys Asn Val Asn His Lys Pro
            260             265             270

Ser Asn Thr Lys Val Asp Lys Lys Val Glu Pro Lys Ser Cys Asp Lys
            275             280             285

Thr His Thr Cys Pro Pro Cys Pro Ala Pro Glu Ala Ala Gly Gly Pro
            290             295             300

Ser Val Phe Leu Phe Pro Pro Lys Pro Lys Asp Thr Leu Met Ile Ser
305             310             315             320

Arg Thr Pro Glu Val Thr Cys Val Val Val Asp Val Ser His Glu Asp
            325             330             335

Pro Glu Val Lys Phe Asn Trp Tyr Val Asp Gly Val Glu Val His Asn
            340             345             350

Ala Lys Thr Lys Pro Arg Glu Glu Gln Tyr Ala Ser Thr Tyr Arg Val
            355             360             365

Val Ser Val Leu Thr Val Leu His Gln Asp Trp Leu Asn Gly Lys Glu
            370             375             380

Tyr Lys Cys Lys Val Ser Asn Lys Ala Leu Pro Ala Pro Ile Glu Lys
385             390             395             400

Thr Ile Ser Lys Ala Lys Gly Gln Pro Arg Glu Pro Gln Val Tyr Thr
            405             410             415

Leu Pro Pro Ser Arg Cys Glu Leu Thr Lys Asn Gln Val Ser Leu Ser
            420             425             430

Cys Ala Val Lys Gly Phe Tyr Pro Ser Asp Ile Ala Val Glu Trp Glu
            435             440             445

Ser Asn Gly Gln Pro Glu Asn Asn Tyr Lys Thr Thr Pro Pro Val Leu
            450             455             460

Asp Ser Asp Gly Ser Phe Phe Leu Val Ser Lys Leu Thr Val Asp Lys
465             470             475             480

Ser Arg Trp Gln Gln Gly Asn Val Phe Ser Cys Ser Val Met His Glu
            485             490             495

Ala Leu His Asn His Tyr Thr Gln Lys Ser Leu Ser Leu Ser Pro Asp
            500             505             510

Tyr Lys Asp Asp Asp Asp Lys
            515
```

<210> SEQ ID NO 105
<211> LENGTH: 483
<212> TYPE: PRT
<213> ORGANISM: Artificial sequence
<220> FEATURE:
<223> OTHER INFORMATION: An artificially synthesized peptide sequence

<400> SEQUENCE: 105

```
Gln Asp Gly Asn Glu Gly Gly Gly Ser Pro Leu Gly Leu Ala Gly
1               5                   10                  15

Gly Gly Ser Gln Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Ser Asn Ala Trp Met His Trp Val Arg Gln Ala Pro Gly Lys Gly Leu
    50                  55                  60

Glu Trp Val Ala Gln Ile Lys Asp Lys Ala Asn Gly Tyr Asn Ala Tyr
65                  70                  75                  80

Tyr Ala Glu Ser Val Lys Gly Arg Phe Thr Ile Ser Arg Asp Asp Ser
                85                  90                  95

Lys Asn Ser Ile Tyr Leu Gln Met Asn Ser Leu Lys Thr Glu Asp Thr
            100                 105                 110

Ala Val Tyr Tyr Cys Arg Tyr Val His Tyr Thr Thr Tyr Ala Gly Phe
        115                 120                 125

Ser Tyr Lys Phe Gly Val Asp Ala Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Ala Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365
```

```
Ala Lys Gly Gln Pro Arg Glu Pro Gln Val Tyr Thr Leu Pro Pro Ser
    370                 375                 380

Arg Cys Glu Leu Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Asp Tyr Lys Asp Asp
465                 470                 475                 480

Asp Asp Lys

<210> SEQ ID NO 106
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 106

Pro Leu Gly Leu Ala Gly
1               5

<210> SEQ ID NO 107
<211> LENGTH: 105
<212> TYPE: PRT
<213> ORGANISM: Homo sapiens

<400> SEQUENCE: 107

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp
            100                 105

<210> SEQ ID NO 108
<211> LENGTH: 571
<212> TYPE: PRT
<213> ORGANISM: Artificial sequence
<220> FEATURE:
<223> OTHER INFORMATION: An artificially synthesized peptide sequence

<400> SEQUENCE: 108

Gln Asp Gly Asn Glu Glu Met Gly Gly Ile Thr Gln Thr Pro Tyr Lys
1               5                   10                  15
```

-continued

```
Val Ser Ile Ser Gly Thr Thr Val Ile Leu Thr Cys Pro Gln Tyr Pro
             20                  25                  30

Gly Ser Glu Ile Leu Trp Gln His Asn Asp Lys Asn Ile Gly Gly Asp
         35                  40                  45

Glu Asp Asp Lys Asn Ile Gly Ser Asp Glu Asp His Leu Ser Leu Lys
     50                  55                  60

Glu Phe Ser Glu Leu Glu Gln Ser Gly Tyr Tyr Val Cys Tyr Pro Arg
 65                  70                  75                  80

Gly Ser Lys Pro Glu Asp Ala Asn Phe Tyr Leu Tyr Leu Arg Ala Arg
                 85                  90                  95

Val Cys Glu Asn Cys Met Glu Met Asp Leu Ser Gly Arg Ser Asp Asn
                100                 105                 110

His Gln Val Gln Leu Val Glu Ser Gly Gly Val Gln Pro Gly
             115                 120                 125

Arg Ser Leu Arg Leu Ser Cys Ala Ala Ser Gly Phe Thr Phe Ser Asn
         130                 135                 140

Ala Trp Met His Trp Val Arg Gln Ala Pro Gly Lys Gly Leu Glu Trp
145                 150                 155                 160

Val Ala Gln Ile Lys Ala Lys Ser Asn Asn Tyr Ala Thr Tyr Tyr Ala
                165                 170                 175

Glu Ser Val Lys Gly Arg Phe Thr Ile Ser Arg Asp Asp Ser Lys Asn
             180                 185                 190

Ser Leu Tyr Leu Gln Met Asn Ser Leu Lys Thr Glu Asp Thr Ala Val
         195                 200                 205

Tyr Tyr Cys Arg Tyr Val His Tyr Gly Ala Tyr Gly Val Asp Ala
     210                 215                 220

Trp Gly Gln Gly Thr Thr Val Thr Val Ser Ser Ala Ser Thr Lys Gly
225                 230                 235                 240

Pro Ser Val Phe Pro Leu Ala Pro Ser Ser Lys Ser Thr Ser Gly Gly
                245                 250                 255

Thr Ala Ala Leu Gly Cys Leu Val Lys Asp Tyr Phe Pro Glu Pro Val
             260                 265                 270

Thr Val Ser Trp Asn Ser Gly Ala Leu Thr Ser Gly Val His Thr Phe
         275                 280                 285

Pro Ala Val Leu Gln Ser Ser Gly Leu Tyr Ser Leu Ser Ser Val Val
     290                 295                 300

Thr Val Pro Ser Ser Ser Leu Gly Thr Gln Thr Tyr Ile Cys Asn Val
305                 310                 315                 320

Asn His Lys Pro Ser Asn Thr Lys Val Asp Lys Lys Val Glu Pro Lys
                325                 330                 335

Ser Cys Asp Lys Thr His Thr Cys Pro Pro Cys Pro Ala Pro Glu Ala
             340                 345                 350

Ala Gly Gly Pro Ser Val Phe Leu Phe Pro Pro Lys Pro Lys Asp Thr
         355                 360                 365

Leu Met Ile Ser Arg Thr Pro Glu Val Thr Cys Val Val Val Asp Val
     370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Ala Ser
                405                 410                 415

Thr Tyr Arg Val Val Ser Val Leu Thr Val Leu His Gln Asp Trp Leu
             420                 425                 430

Asn Gly Lys Glu Tyr Lys Cys Lys Val Ser Asn Lys Ala Leu Pro Ala
```

```
              435                 440                 445
Pro Ile Glu Lys Thr Ile Ser Lys Ala Lys Gly Gln Pro Arg Glu Pro
450                 455                 460

Gln Val Tyr Thr Leu Pro Pro Ser Arg Cys Glu Leu Thr Lys Asn Gln
465                 470                 475                 480

Val Ser Leu Ser Cys Ala Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Val Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Asp Tyr Lys Asp Asp Asp Lys
                565                 570
```

<210> SEQ ID NO 109
<211> LENGTH: 590
<212> TYPE: PRT
<213> ORGANISM: Artificial sequence
<220> FEATURE:
<223> OTHER INFORMATION: An artificially synthesized peptide sequence

<400> SEQUENCE: 109

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Gly Gly Gly Ser Gly Gly
            100                 105                 110

Gly Gly Ser Gly Gly Gly Ser Leu Ser Gly Arg Ser Asp Asn His
        115                 120                 125

Gly Gly Gly Ser Gln Val Gln Leu Val Glu Ser Gly Gly Gly Val Val
    130                 135                 140

Gln Pro Gly Arg Ser Leu Arg Leu Ser Cys Ala Ala Ser Gly Phe Thr
145                 150                 155                 160

Phe Ser Asn Ala Trp Met His Trp Val Arg Gln Ala Pro Gly Lys Gly
                165                 170                 175

Leu Glu Trp Val Ala Gln Ile Lys Ala Lys Ser Asn Asn Tyr Ala Thr
            180                 185                 190

Tyr Tyr Ala Glu Ser Val Lys Gly Arg Phe Thr Ile Ser Arg Asp Asp
        195                 200                 205

Ser Lys Asn Ser Leu Tyr Leu Gln Met Asn Ser Leu Lys Thr Glu Asp
    210                 215                 220

Thr Ala Val Tyr Tyr Cys Arg Tyr Val His Tyr Gly Ala Tyr Tyr Gly
```

```
            225                 230                 235                 240
Val Asp Ala Trp Gly Gln Gly Thr Thr Val Thr Val Ser Ser Ala Ser
                245                 250                 255

Thr Lys Gly Pro Ser Val Phe Pro Leu Ala Pro Ser Ser Lys Ser Thr
            260                 265                 270

Ser Gly Gly Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Gln Thr Tyr Ile
                325                 330                 335

Cys Asn Val Asn His Lys Pro Ser Asn Thr Lys Val Asp Lys Lys Val
            340                 345                 350

Glu Pro Lys Ser Cys Asp Lys Thr His Thr Cys Pro Pro Cys Pro Ala
        355                 360                 365

Pro Glu Ala Ala Gly Gly Pro Ser Val Phe Leu Phe Pro Pro Lys Pro
    370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
            420                 425                 430

Tyr Ala Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Ala
    450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Cys Glu Leu Thr
                485                 490                 495

Lys Asn Gln Val Ser Leu Ser Cys Ala Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Val
    530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Asp Tyr Lys Asp Asp Asp Lys
            580                 585                 590

<210> SEQ ID NO 110
<211> LENGTH: 332
<212> TYPE: PRT
<213> ORGANISM: Artificial sequence
<220> FEATURE:
<223> OTHER INFORMATION: An artificially synthesized peptide sequence

<400> SEQUENCE: 110

Gln Asp Gly Asn Glu Glu Met Gly Gly Ile Thr Gln Thr Pro Tyr Lys
```

```
            1               5                   10                  15
        Val Ser Ile Ser Gly Thr Thr Val Ile Leu Thr Cys Pro Gln Tyr Pro
                        20                  25                  30

Gly Ser Glu Ile Leu Trp Gln His Asn Asp Lys Asn Ile Gly Gly Asp
                        35                  40                  45

Glu Asp Lys Asn Ile Gly Ser Asp Glu Asp His Leu Ser Leu Lys
                        50                  55                  60

Glu Phe Ser Glu Leu Glu Gln Ser Gly Tyr Tyr Val Cys Tyr Pro Arg
        65                      70                  75                  80

Gly Ser Lys Pro Glu Asp Ala Asn Phe Tyr Leu Tyr Leu Arg Ala Arg
                        85                  90                  95

Val Cys Glu Asn Cys Met Glu Met Asp Leu Ser Gly Arg Ser Asp Asn
                        100                 105                 110

His Asp Ile Val Met Thr Gln Ser Pro Leu Ser Leu Pro Val Thr Pro
                        115                 120                 125

Gly Glu Pro Ala Ser Ile Ser Cys Arg Ser Ser Gln Ser Leu Val His
                        130                 135                 140

Ser Asn Arg Asn Thr Tyr Leu His Trp Tyr Gln Gln Lys Pro Gly Gln
        145                     150                 155                 160

Ala Pro Arg Leu Leu Ile Tyr Lys Val Ser Asn Arg Phe Ser Gly Val
                        165                 170                 175

Pro Asp Arg Phe Ser Gly Ser Gly Ser Gly Thr Asp Phe Thr Leu Lys
                        180                 185                 190

Ile Ser Arg Val Glu Ala Glu Asp Val Gly Val Tyr Tyr Cys Gly Gln
                        195                 200                 205

Gly Thr Gln Val Pro Tyr Thr Phe Gly Gln Gly Thr Lys Leu Glu Ile
                        210                 215                 220

Lys Arg Thr Val Ala Ala Pro Ser Val Phe Ile Phe Pro Pro Ser Asp
        225                     230                 235                 240

Glu Gln Leu Lys Ser Gly Thr Ala Ser Val Val Cys Leu Leu Asn Asn
                        245                 250                 255

Phe Tyr Pro Arg Glu Ala Lys Val Gln Trp Lys Val Asp Asn Ala Leu
                        260                 265                 270

Gln Ser Gly Asn Ser Gln Glu Ser Val Thr Glu Gln Asp Ser Lys Asp
                        275                 280                 285

Ser Thr Tyr Ser Leu Ser Ser Thr Leu Thr Leu Ser Lys Ala Asp Tyr
                        290                 295                 300

Glu Lys His Lys Val Tyr Ala Cys Glu Val Thr His Gln Gly Leu Ser
        305                     310                 315                 320

Ser Pro Val Thr Lys Ser Phe Asn Arg Gly Glu Cys
                        325                 330

<210> SEQ ID NO 111
<211> LENGTH: 351
<212> TYPE: PRT
<213> ORGANISM: Artificial sequence
<220> FEATURE:
<223> OTHER INFORMATION: An artificially synthesized peptide sequence

<400> SEQUENCE: 111

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
```

```
                35                  40                  45
Glu Asp Asp Lys Asn Ile Gly Ser Asp Glu Asp His Leu Ser Leu Lys
 50                  55                  60
Glu Phe Ser Glu Leu Glu Gln Ser Gly Tyr Tyr Val Cys Tyr Pro Arg
 65                  70                  75                  80
Gly Ser Lys Pro Glu Asp Ala Asn Phe Tyr Leu Tyr Leu Arg Ala Arg
                 85                  90                  95
Val Cys Glu Asn Cys Met Glu Met Asp Gly Gly Gly Ser Gly Gly
            100                 105                 110
Gly Gly Ser Gly Gly Gly Gly Ser Leu Ser Gly Arg Ser Asp Asn His
            115                 120                 125
Gly Gly Gly Ser Asp Ile Val Met Thr Gln Ser Pro Leu Ser Leu Pro
130                 135                 140
Val Thr Pro Gly Glu Pro Ala Ser Ile Ser Cys Arg Ser Ser Gln Ser
145                 150                 155                 160
Leu Val His Ser Asn Arg Asn Thr Tyr Leu His Trp Tyr Gln Gln Lys
                165                 170                 175
Pro Gly Gln Ala Pro Arg Leu Leu Ile Tyr Lys Val Ser Asn Arg Phe
            180                 185                 190
Ser Gly Val Pro Asp Arg Phe Ser Gly Ser Gly Ser Gly Thr Asp Phe
            195                 200                 205
Thr Leu Lys Ile Ser Arg Val Glu Ala Glu Asp Val Gly Val Tyr Tyr
210                 215                 220
Cys Gly Gln Gly Thr Gln Val Pro Tyr Thr Phe Gly Gln Gly Thr Lys
225                 230                 235                 240
Leu Glu Ile Lys Arg Thr Val Ala Ala Pro Ser Val Phe Ile Phe Pro
                245                 250                 255
Pro Ser Asp Glu Gln Leu Lys Ser Gly Thr Ala Ser Val Val Cys Leu
            260                 265                 270
Leu Asn Asn Phe Tyr Pro Arg Glu Ala Lys Val Gln Trp Lys Val Asp
            275                 280                 285
Asn Ala Leu Gln Ser Gly Asn Ser Gln Glu Ser Val Thr Glu Gln Asp
290                 295                 300
Ser Lys Asp Ser Thr Tyr Ser Leu Ser Ser Thr Leu Thr Leu Ser Lys
305                 310                 315                 320
Ala Asp Tyr Glu Lys His Lys Val Tyr Ala Cys Glu Val Thr His Gln
                325                 330                 335
Gly Leu Ser Ser Pro Val Thr Lys Ser Phe Asn Arg Gly Glu Cys
            340                 345                 350

<210> SEQ ID NO 112
<211> LENGTH: 443
<212> TYPE: PRT
<213> ORGANISM: Artificial sequence
<220> FEATURE:
<223> OTHER INFORMATION: An artificially synthesized peptide sequence

<400> SEQUENCE: 112

Gln Val Gln Leu Val Gln Ser Gly Ala Glu Val Lys Lys Pro Gly Ala
 1               5                  10                  15
Ser Val Thr Val Ser Cys Lys Ala Ser Gly Tyr Thr Phe Thr Asp Tyr
                 20                  25                  30
Glu Met His Trp Ile Arg Gln Pro Pro Gly Glu Gly Leu Glu Trp Ile
             35                  40                  45
Gly Ala Ile Asp Gly Pro Thr Pro Asp Thr Ala Tyr Ser Glu Lys Phe
```

```
            50                  55                  60
Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                     85                  90                  95

Thr Arg Phe Tyr Ser Tyr Thr Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Tyr Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440

<210> SEQ ID NO 113
<211> LENGTH: 219
<212> TYPE: PRT
<213> ORGANISM: Artificial sequence
```

<220> FEATURE:
<223> OTHER INFORMATION: An artificially synthesized peptide sequence

<400> SEQUENCE: 113

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 114
<211> LENGTH: 129
<212> TYPE: PRT
<213> ORGANISM: Artificial sequence
<220> FEATURE:
<223> OTHER INFORMATION: An artificially synthesized peptide sequence

<400> SEQUENCE: 114

Gln Asp Gly Asn Glu Gly Gly Gly Ser Gly Gly Ser Gly Gly Gly
1               5                   10                  15

Ser Asp Val Val Met Thr Gln Thr Pro Val Ser Met Ser Val Ser Leu
            20                  25                  30

Gly Gly Gln Val Ser Ile Ser Cys Arg Ser Ser Gln Ser Leu Val His
        35                  40                  45

Asn Asn Gly Asn Thr Tyr Val Ser Trp Tyr Ile Gln Lys Pro Ser Gln
    50                  55                  60

Ser Pro Gln Leu Leu Ile Tyr Lys Val Ser Asn Arg Phe Ser Gly Ile
65                  70                  75                  80

Ser Asp Arg Phe Ser Gly Ser Gly Ser Gly Thr Asp Phe Thr Leu Lys
                85                  90                  95

Ile Ser Arg Val Glu Pro Asp Leu Gly Val Tyr Tyr Cys Gly Gln
            100                 105                 110

Gly Thr Gln Asp Pro Tyr Thr Phe Gly Ala Gly Thr Lys Leu Glu Leu

Lys

<210> SEQ ID NO 115
<211> LENGTH: 143
<212> TYPE: PRT
<213> ORGANISM: Artificial sequence
<220> FEATURE:
<223> OTHER INFORMATION: An artificially synthesized peptide sequence

<400> SEQUENCE: 115

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Ser Asp
            20                  25                  30

Val Val Met Thr Gln Thr Pro Val Ser Met Ser Val Ser Leu Gly Gly
        35                  40                  45

Gln Val Ser Ile Ser Cys Arg Ser Ser Gln Ser Leu Val His Asn Asn
    50                  55                  60

Gly Asn Thr Tyr Val Ser Trp Tyr Ile Gln Lys Pro Ser Gln Ser Pro
65                  70                  75                  80

Gln Leu Leu Ile Tyr Lys Val Ser Asn Arg Phe Ser Gly Ile Ser Asp
                85                  90                  95

Arg Phe Ser Gly Ser Gly Ser Gly Thr Asp Phe Thr Leu Lys Ile Ser
            100                 105                 110

Arg Val Glu Pro Asp Asp Leu Gly Val Tyr Tyr Cys Gly Gln Gly Thr
        115                 120                 125

Gln Asp Pro Tyr Thr Phe Gly Ala Gly Thr Lys Leu Glu Leu Lys
    130                 135                 140

<210> SEQ ID NO 116
<211> LENGTH: 463
<212> TYPE: PRT
<213> ORGANISM: Artificial sequence
<220> FEATURE:
<223> OTHER INFORMATION: An artificially synthesized peptide sequence

<400> SEQUENCE: 116

Gln Asp Gly Asn Glu Gly Gly Ser Gly Gly Gly Ser Gln Val Gln
1               5                   10                  15

Leu Val Glu Ser Gly Gly Gly Val Val Gln Pro Gly Arg Ser Leu Arg
            20                  25                  30

Leu Ser Cys Ala Ala Ser Gly Phe Thr Phe Ser Asn Ala Trp Met His
        35                  40                  45

Trp Val Arg Gln Ala Pro Gly Lys Gly Leu Glu Trp Val Ala Gln Ile
    50                  55                  60

Lys Ala Lys Ser Asn Asn Tyr Ala Thr Tyr Tyr Ala Glu Ser Val Lys
65                  70                  75                  80

Gly Arg Phe Thr Ile Ser Arg Asp Asp Ser Lys Asn Ser Leu Tyr Leu
                85                  90                  95

Gln Met Asn Ser Leu Lys Thr Glu Asp Thr Ala Val Tyr Tyr Cys Arg
            100                 105                 110

Tyr Val His Tyr Gly Ala Tyr Tyr Gly Val Asp Ala Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu

```
                145                 150                 155                 160
Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
                195                 200                 205

Ser Ser Leu Gly Thr Gln Thr Tyr Ile Cys Asn Val Asn His Lys Pro
            210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Arg Gly Gly Pro
                245                 250                 255

Lys Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
                275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Lys Glu Met Thr Lys Asn Gln Val Ser Leu Thr
            370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Tyr Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
                435                 440                 445

Ala Leu His Asn His Tyr Thr Gln Lys Ser Leu Ser Leu Ser Pro
            450                 455                 460

<210> SEQ ID NO 117
<211> LENGTH: 481
<212> TYPE: PRT
<213> ORGANISM: Artificial sequence
<220> FEATURE:
<223> OTHER INFORMATION: An artificially synthesized peptide sequence

<400> SEQUENCE: 117

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Gln
                20                  25                  30

Val Gln Leu Val Glu Ser Gly Gly Gly Val Val Gln Pro Gly Arg Ser
                35                  40                  45

Leu Arg Leu Ser Cys Ala Ala Ser Gly Phe Thr Phe Ser Asn Ala Trp
```

```
                50                  55                  60
Met His Trp Val Arg Gln Ala Pro Gly Lys Gly Leu Glu Trp Val Ala
 65                      70                  75                  80

Gln Ile Lys Ala Lys Ser Asn Asn Tyr Ala Thr Tyr Tyr Ala Glu Ser
                     85                  90                  95

Val Lys Gly Arg Phe Thr Ile Ser Arg Asp Asp Ser Lys Asn Ser Leu
                    100                 105                 110

Tyr Leu Gln Met Asn Ser Leu Lys Thr Glu Asp Thr Ala Val Tyr Tyr
                115                 120                 125

Cys Arg Tyr Val His Tyr Gly Ala Tyr Gly Val Asp Ala Trp Gly
    130                 135                 140

Gln Gly Thr Thr Val Thr Val Ser Ser Ala Ser Thr Lys Gly Pro Ser
145                     150                 155                 160

Val Phe Pro Leu Ala Pro Ser Ser Lys Ser Thr Ser Gly Gly Thr Ala
                    165                 170                 175

Ala Leu Gly Cys Leu Val Lys Asp Tyr Phe Pro Glu Pro Val Thr Val
                180                 185                 190

Ser Trp Asn Ser Gly Ala Leu Thr Ser Gly Val His Thr Phe Pro Ala
                195                 200                 205

Val Leu Gln Ser Ser Gly Leu Tyr Ser Leu Ser Ser Val Val Thr Val
                210                 215                 220

Pro Ser Ser Ser Leu Gly Thr Gln Thr Tyr Ile Cys Asn Val Asn His
225                     230                 235                 240

Lys Pro Ser Asn Thr Lys Val Asp Lys Lys Val Glu Pro Lys Ser Cys
                    245                 250                 255

Asp Lys Thr His Thr Cys Pro Pro Cys Pro Ala Pro Glu Leu Arg Gly
                260                 265                 270

Gly Pro Lys Val Phe Leu Phe Pro Pro Lys Pro Lys Asp Thr Leu Met
                275                 280                 285

Ile Ser Arg Thr Pro Glu Val Thr Cys Val Val Val Asp Val Ser His
                290                 295                 300

Glu Asp Pro Glu Val Lys Phe Asn Trp Tyr Val Asp Gly Val Glu Val
305                     310                 315                 320

His Asn Ala Lys Thr Lys Pro Arg Glu Glu Gln Tyr Ala Ser Thr Tyr
                    325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Gln Val
                370                 375                 380

Tyr Thr Leu Pro Pro Ser Arg Lys Glu Met Thr Lys Asn Gln Val Ser
385                     390                 395                 400

Leu Thr Cys Leu Val Lys Gly Phe Tyr Pro Ser Asp Ile Ala Val Glu
                    405                 410                 415

Trp Glu Ser Asn Gly Gln Pro Glu Asn Asn Tyr Lys Thr Thr Pro Pro
                420                 425                 430

Tyr Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                     470                 475                 480
```

Pro

<210> SEQ ID NO 118
<211> LENGTH: 482
<212> TYPE: PRT
<213> ORGANISM: Artificial sequence
<220> FEATURE:
<223> OTHER INFORMATION: An artificially synthesized peptide sequence

<400> SEQUENCE: 118

```
Gln Asp Gly Asn Glu Glu Met Gly Gly Ile Thr Gln Thr Pro Tyr Lys
1               5                   10                  15

Val Ser Ile Ser Leu Ser Gly Arg Ser Asp Asn His Gly Gly Gly Ser
            20                  25                  30

Gln Val Gln Leu Val Glu Ser Gly Gly Val Val Gln Pro Gly Arg
        35                  40                  45

Ser Leu Arg Leu Ser Cys Ala Ala Ser Gly Phe Thr Phe Ser Asn Ala
    50                  55                  60

Trp Met His Trp Val Arg Gln Ala Pro Gly Lys Gly Leu Glu Trp Val
65                  70                  75                  80

Ala Gln Ile Lys Ala Lys Ser Asn Asn Tyr Ala Thr Tyr Tyr Ala Glu
                85                  90                  95

Ser Val Lys Gly Arg Phe Thr Ile Ser Arg Asp Asp Ser Lys Asn Ser
            100                 105                 110

Leu Tyr Leu Gln Met Asn Ser Leu Lys Thr Glu Asp Thr Ala Val Tyr
        115                 120                 125

Tyr Cys Arg Tyr Val His Tyr Gly Ala Tyr Tyr Gly Val Asp Ala Trp
    130                 135                 140

Gly Gln Gly Thr Thr Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Arg
            260                 265                 270

Gly Gly Pro Lys Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Ala Ser Thr
                325                 330                 335

Tyr Arg Val Val Ser Val Leu Thr Val Leu His Gln Asp Trp Leu Asn
            340                 345                 350
```

```
Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Lys Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
    420                 425                 430

Pro Tyr Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro

<210> SEQ ID NO 119
<211> LENGTH: 485
<212> TYPE: PRT
<213> ORGANISM: Artificial sequence
<220> FEATURE:
<223> OTHER INFORMATION: An artificially synthesized peptide sequence

<400> SEQUENCE: 119

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30

Asp Asn His Gln Val Gln Leu Val Glu Ser Gly Gly Gly Val Val Gln
        35                  40                  45

Pro Gly Arg Ser Leu Arg Leu Ser Cys Ala Ala Ser Gly Phe Thr Phe
    50                  55                  60

Ser Asn Ala Trp Met His Trp Val Arg Gln Ala Pro Gly Lys Gly Leu
65                  70                  75                  80

Glu Trp Val Ala Gln Ile Lys Ala Lys Ser Asn Asn Tyr Ala Thr Tyr
            85                  90                  95

Tyr Ala Glu Ser Val Lys Gly Arg Phe Thr Ile Ser Arg Asp Asp Ser
            100                 105                 110

Lys Asn Ser Leu Tyr Leu Gln Met Asn Ser Leu Lys Thr Glu Asp Thr
        115                 120                 125

Ala Val Tyr Tyr Cys Arg Tyr Val His Tyr Gly Ala Tyr Tyr Gly Val
    130                 135                 140

Asp Ala Trp Gly Gln Gly Thr Thr Val Thr Val Ser Ser Ala Ser Thr
145                 150                 155                 160

Lys Gly Pro Ser Val Phe Pro Leu Ala Pro Ser Ser Lys Ser Thr Ser
            165                 170                 175

Gly Gly Thr Ala Ala Leu Gly Cys Leu Val Lys Asp Tyr Phe Pro Glu
        180                 185                 190

Pro Val Thr Val Ser Trp Asn Ser Gly Ala Leu Thr Ser Gly Val His
    195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
```

```
                225                 230                 235                 240
Asn Val Asn His Lys Pro Ser Asn Thr Lys Val Asp Lys Lys Val Glu
                    245                 250                 255
Pro Lys Ser Cys Asp Lys Thr His Thr Cys Pro Pro Cys Pro Ala Pro
                    260                 265                 270
Glu Leu Arg Gly Gly Pro Lys Val Phe Leu Phe Pro Pro Lys Pro Lys
                    275                 280                 285
Asp Thr Leu Met Ile Ser Arg Thr Pro Glu Val Thr Cys Val Val Val
                    290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                    325                 330                 335
Ala Ser Thr Tyr Arg Val Val Ser Val Leu Thr Val Leu His Gln Asp
                    340                 345                 350
Trp Leu Asn Gly Lys Glu Tyr Lys Cys Lys Val Ser Asn Lys Ala Leu
                    355                 360                 365
Pro Ala Pro Ile Glu Lys Thr Ile Ser Lys Ala Lys Gly Gln Pro Arg
                    370                 375                 380
Glu Pro Gln Val Tyr Thr Leu Pro Pro Ser Arg Lys Glu Met Thr Lys
385                 390                 395                 400
Asn Gln Val Ser Leu Thr Cys Leu Val Lys Gly Phe Tyr Pro Ser Asp
                    405                 410                 415
Ile Ala Val Glu Trp Glu Ser Asn Gly Gln Pro Glu Asn Asn Tyr Lys
                    420                 425                 430
Thr Thr Pro Pro Tyr Leu Asp Ser Asp Gly Ser Phe Phe Leu Tyr Ser
                    435                 440                 445
Lys Leu Thr Val Asp Lys Ser Arg Trp Gln Gln Gly Asn Val Phe Ser
                    450                 455                 460
Cys Ser Val Met His Glu Ala Leu His Asn His Tyr Thr Gln Lys Ser
465                 470                 475                 480
Leu Ser Leu Ser Pro
                485

<210> SEQ ID NO 120
<211> LENGTH: 469
<212> TYPE: PRT
<213> ORGANISM: Artificial sequence
<220> FEATURE:
<223> OTHER INFORMATION: An artificially synthesized peptide sequence

<400> SEQUENCE: 120

Gln Asp Gly Asn Glu Gly Gly Ser Gly Gly Gly Ser Gln Val Gln
1                   5                   10                  15
Leu Val Glu Ser Gly Gly Gly Leu Val Gln Pro Gly Arg Ser Leu Arg
                    20                  25                  30
Leu Ser Cys Ala Ala Ser Gly Phe Thr Phe Ser Asn Ala Trp Met His
                    35                  40                  45
Trp Val Arg Gln Ala Pro Gly Lys Gly Leu Glu Trp Val Ala Gln Ile
                    50                  55                  60
Lys Asp Lys Ala Asn Gly Tyr Asn Ala Tyr Ala Glu Ser Val Lys
65                  70                  75                  80
Gly Arg Phe Thr Ile Ser Arg Asp Asp Ser Lys Asn Ser Ile Tyr Leu
                    85                  90                  95
Gln Met Asn Ser Leu Lys Thr Glu Asp Thr Ala Val Tyr Tyr Cys Arg
```

```
                  100                 105                 110
Tyr Val His Tyr Thr Thr Tyr Ala Gly Phe Ser Tyr Lys Phe Gly Val
            115                 120                 125
Asp Ala Trp Gly Gln Gly Thr Thr Val Thr Val Ser Ser Ala Ser Thr
130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Leu Gly Thr Gln Thr Tyr Ile Cys
            210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Arg Gly Gly Pro Lys Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
            290                 295                 300
Gly Val Glu Val His Asn Ala Lys Thr Lys Pro Arg Glu Glu Gln Tyr
305                 310                 315                 320
Ala Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Lys Glu Met Thr Lys
            370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Tyr Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
            450                 455                 460
Leu Ser Leu Ser Pro
465

<210> SEQ ID NO 121
<211> LENGTH: 487
<212> TYPE: PRT
<213> ORGANISM: Artificial sequence
<220> FEATURE:
<223> OTHER INFORMATION: An artificially synthesized peptide sequence
```

<400> SEQUENCE: 121

```
Gln Asp Gly Asn Glu Glu Met Gly Gly Gly Ser Gly Gly Gly Ser Gly
1               5                   10                  15
Gly Gly Ser Leu Ser Gly Arg Ser Asp Asn His Gly Gly Gly Ser Gln
            20                  25                  30
Val Gln Leu Val Glu Ser Gly Gly Leu Val Gln Pro Gly Arg Ser
        35                  40                  45
Leu Arg Leu Ser Cys Ala Ala Ser Gly Phe Thr Phe Ser Asn Ala Trp
    50                  55                  60
Met His Trp Val Arg Gln Ala Pro Gly Lys Gly Leu Glu Trp Val Ala
65                  70                  75                  80
Gln Ile Lys Asp Lys Ala Asn Gly Tyr Asn Ala Tyr Ala Glu Ser
                85                  90                  95
Val Lys Gly Arg Phe Thr Ile Ser Arg Asp Asp Ser Lys Asn Ser Ile
            100                 105                 110
Tyr Leu Gln Met Asn Ser Leu Lys Thr Glu Asp Thr Ala Val Tyr Tyr
        115                 120                 125
Cys Arg Tyr Val His Tyr Thr Thr Tyr Ala Gly Phe Ser Tyr Lys Phe
130                 135                 140
Gly Val Asp Ala Trp Gly Gln Gly Thr Thr Val Thr Val Ser Ser Ala
145                 150                 155                 160
Ser Thr Lys Gly Pro Ser Val Phe Pro Leu Ala Pro Ser Ser Lys Ser
                165                 170                 175
Thr Ser Gly Gly Thr Ala Ala Leu Gly Cys Leu Val Lys Asp Tyr Phe
            180                 185                 190
Pro Glu Pro Val Thr Val Ser Trp Asn Ser Gly Ala Leu Thr Ser Gly
        195                 200                 205
Val His Thr Phe Pro Ala Val Leu Gln Ser Ser Gly Leu Tyr Ser Leu
    210                 215                 220
Ser Ser Val Val Thr Val Pro Ser Ser Ser Leu Gly Thr Gln Thr Tyr
225                 230                 235                 240
Ile Cys Asn Val Asn His Lys Pro Ser Asn Thr Lys Val Asp Lys Lys
                245                 250                 255
Val Glu Pro Lys Ser Cys Asp Lys Thr His Thr Cys Pro Pro Cys Pro
            260                 265                 270
Ala Pro Glu Leu Arg Gly Gly Pro Lys Val Phe Leu Phe Pro Pro Lys
        275                 280                 285
Pro Lys Asp Thr Leu Met Ile Ser Arg Thr Pro Glu Val Thr Cys Val
    290                 295                 300
Val Val Asp Val Ser His Glu Asp Pro Glu Val Lys Phe Asn Trp Tyr
305                 310                 315                 320
Val Asp Gly Val Glu Val His Asn Ala Lys Thr Lys Pro Arg Glu Glu
                325                 330                 335
Gln Tyr Ala Ser Thr Tyr Arg Val Val Ser Val Leu Thr Val Leu His
            340                 345                 350
Gln Asp Trp Leu Asn Gly Lys Glu Tyr Lys Cys Lys Val Ser Asn Lys
        355                 360                 365
Ala Leu Pro Ala Pro Ile Glu Lys Thr Ile Ser Lys Ala Lys Gly Gln
    370                 375                 380
Pro Arg Glu Pro Gln Val Tyr Thr Leu Pro Pro Ser Arg Lys Glu Met
385                 390                 395                 400
Thr Lys Asn Gln Val Ser Leu Thr Cys Leu Val Lys Gly Phe Tyr Pro
                405                 410                 415
```

```
Ser Asp Ile Ala Val Glu Trp Glu Ser Asn Gly Gln Pro Glu Asn Asn
            420                 425                 430

Tyr Lys Thr Thr Pro Pro Tyr Leu Asp Ser Asp Gly Ser Phe Phe Leu
            435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro
                485

<210> SEQ ID NO 122
<211> LENGTH: 488
<212> TYPE: PRT
<213> ORGANISM: Artificial sequence
<220> FEATURE:
<223> OTHER INFORMATION: An artificially synthesized peptide sequence

<400> SEQUENCE: 122

Gln Asp Gly Asn Glu Glu Met Gly Gly Ile Thr Gln Thr Pro Tyr Lys
1               5                   10                  15

Val Ser Ile Ser Leu Ser Gly Arg Ser Asp Asn His Gly Gly Gly Ser
                20                  25                  30

Gln Val Gln Leu Val Glu Ser Gly Gly Gly Leu Val Gln Pro Gly Arg
            35                  40                  45

Ser Leu Arg Leu Ser Cys Ala Ala Ser Gly Phe Thr Phe Ser Asn Ala
        50                  55                  60

Trp Met His Trp Val Arg Gln Ala Pro Gly Lys Gly Leu Glu Trp Val
65                  70                  75                  80

Ala Gln Ile Lys Asp Lys Ala Asn Gly Tyr Asn Ala Tyr Tyr Ala Glu
                85                  90                  95

Ser Val Lys Gly Arg Phe Thr Ile Ser Arg Asp Asp Ser Lys Asn Ser
                100                 105                 110

Ile Tyr Leu Gln Met Asn Ser Leu Lys Thr Glu Asp Thr Ala Val Tyr
            115                 120                 125

Tyr Cys Arg Tyr Val His Tyr Thr Thr Tyr Ala Gly Phe Ser Tyr Lys
        130                 135                 140

Phe Gly Val Asp Ala Trp Gly Gln Gly Thr Thr Val Thr Val Ser Ser
145                 150                 155                 160

Ala Ser Thr Lys Gly Pro Ser Val Phe Pro Leu Ala Pro Ser Ser Lys
                165                 170                 175

Ser Thr Ser Gly Gly Thr Ala Ala Leu Gly Cys Leu Val Lys Asp Tyr
            180                 185                 190

Phe Pro Glu Pro Val Thr Val Ser Trp Asn Ser Gly Ala Leu Thr Ser
        195                 200                 205

Gly Val His Thr Phe Pro Ala Val Leu Gln Ser Ser Gly Leu Tyr Ser
    210                 215                 220

Leu Ser Ser Val Val Thr Val Pro Ser Ser Ser Leu Gly Thr Gln Thr
225                 230                 235                 240

Tyr Ile Cys Asn Val Asn His Lys Pro Ser Asn Thr Lys Val Asp Lys
                245                 250                 255

Lys Val Glu Pro Lys Ser Cys Asp Lys Thr His Thr Cys Pro Pro Cys
            260                 265                 270

Pro Ala Pro Glu Leu Arg Gly Gly Pro Lys Val Phe Leu Phe Pro Pro
        275                 280                 285
```

```
Lys Pro Lys Asp Thr Leu Met Ile Ser Arg Thr Pro Glu Val Thr Cys
            290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Ala Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
            370                 375                 380

Gln Pro Arg Glu Pro Gln Val Tyr Thr Leu Pro Pro Ser Arg Lys Glu
385                 390                 395                 400

Met Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
                420                 425                 430

Asn Tyr Lys Thr Thr Pro Pro Tyr Leu Asp Ser Asp Gly Ser Phe Phe
            435                 440                 445

Leu Tyr Ser Lys Leu Thr Val Asp Lys Ser Arg Trp Gln Gln Gly Asn
450                 455                 460

Val Phe Ser Cys Ser Val Met His Glu Ala Leu His Asn His Tyr Thr
465                 470                 475                 480

Gln Lys Ser Leu Ser Leu Ser Pro
            485

<210> SEQ ID NO 123
<211> LENGTH: 491
<212> TYPE: PRT
<213> ORGANISM: Artificial sequence
<220> FEATURE:
<223> OTHER INFORMATION: An artificially synthesized peptide sequence

<400> SEQUENCE: 123

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Leu Ser Gly Arg Ser
            20                  25                  30

Asp Asn His Gln Val Gln Leu Val Glu Ser Gly Gly Gly Leu Val Gln
            35                  40                  45

Pro Gly Arg Ser Leu Arg Leu Ser Cys Ala Ala Ser Gly Phe Thr Phe
50                  55                  60

Ser Asn Ala Trp Met His Trp Val Arg Gln Ala Pro Gly Lys Gly Leu
65                  70                  75                  80

Glu Trp Val Ala Gln Ile Lys Asp Lys Ala Asn Gly Tyr Asn Ala Tyr
                85                  90                  95

Tyr Ala Glu Ser Val Lys Gly Arg Phe Thr Ile Ser Arg Asp Asp Ser
            100                 105                 110

Lys Asn Ser Ile Tyr Leu Gln Met Asn Ser Leu Lys Thr Glu Asp Thr
            115                 120                 125

Ala Val Tyr Tyr Cys Arg Tyr Val His Tyr Thr Thr Tyr Ala Gly Phe
            130                 135                 140

Ser Tyr Lys Phe Gly Val Asp Ala Trp Gly Gln Gly Thr Thr Val Thr
145                 150                 155                 160
```

Val Ser Ser Ala Ser Thr Lys Gly Pro Ser Val Phe Pro Leu Ala Pro
            165                 170                 175

Ser Ser Lys Ser Thr Ser Gly Gly Thr Ala Ala Leu Gly Cys Leu Val
            180                 185                 190

Lys Asp Tyr Phe Pro Glu Pro Val Thr Val Ser Trp Asn Ser Gly Ala
            195                 200                 205

Leu Thr Ser Gly Val His Thr Phe Pro Ala Val Leu Gln Ser Ser Gly
            210                 215                 220

Leu Tyr Ser Leu Ser Ser Val Val Thr Val Pro Ser Ser Ser Leu Gly
225                 230                 235                 240

Thr Gln Thr Tyr Ile Cys Asn Val Asn His Lys Pro Ser Asn Thr Lys
            245                 250                 255

Val Asp Lys Lys Val Glu Pro Lys Ser Cys Asp Lys Thr His Thr Cys
            260                 265                 270

Pro Pro Cys Pro Ala Pro Glu Leu Arg Gly Gly Pro Lys Val Phe Leu
            275                 280                 285

Phe Pro Pro Lys Pro Lys Asp Thr Leu Met Ile Ser Arg Thr Pro Glu
            290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
            325                 330                 335

Pro Arg Glu Glu Gln Tyr Ala Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Ala Leu Pro Ala Pro Ile Glu Lys Thr Ile Ser Lys
            370                 375                 380

Ala Lys Gly Gln Pro Arg Glu Pro Gln Val Tyr Thr Leu Pro Pro Ser
385                 390                 395                 400

Arg Lys Glu Met Thr Lys Asn Gln Val Ser Leu Thr Cys Leu Val Lys
            405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Tyr Leu Asp Ser Asp Gly
            435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro
            485                 490

<210> SEQ ID NO 124
<211> LENGTH: 497
<212> TYPE: PRT
<213> ORGANISM: Artificial sequence
<220> FEATURE:
<223> OTHER INFORMATION: An artificially synthesized peptide sequence

<400> SEQUENCE: 124

Gln Asp Gly Asn Glu Glu Met Gly Gly Ile Thr Gln Thr Pro Tyr Lys
1               5                   10                  15

Val Ser Ile Ser Gly Gly Gly Gly Ser Gly Gly Gly Gly Ser Gly Gly
            20                  25                  30

```
Gly Gly Ser Leu Ser Gly Arg Ser Asp Asn His Gly Gly Gly Ser Gln
        35                  40                  45

Val Gln Leu Val Glu Ser Gly Gly Val Val Gln Pro Gly Arg Ser
 50                  55                  60

Leu Arg Leu Ser Cys Ala Ala Ser Gly Phe Thr Phe Ser Asn Ala Trp
 65                  70                  75                  80

Met His Trp Val Arg Gln Ala Pro Gly Lys Gly Leu Glu Trp Val Ala
                 85                  90                  95

Gln Ile Lys Ala Lys Ser Asn Asn Tyr Ala Thr Tyr Tyr Ala Glu Ser
                100                 105                 110

Val Lys Gly Arg Phe Thr Ile Ser Arg Asp Asp Ser Lys Asn Ser Leu
                115                 120                 125

Tyr Leu Gln Met Asn Ser Leu Lys Thr Glu Asp Thr Ala Val Tyr Tyr
            130                 135                 140

Cys Arg Tyr Val His Tyr Gly Ala Tyr Gly Val Asp Ala Trp Gly
145                 150                 155                 160

Gln Gly Thr Thr Val Thr Val Ser Ser Ala Ser Thr Lys Gly Pro Ser
                165                 170                 175

Val Phe Pro Leu Ala Pro Ser Ser Lys Ser Thr Ser Gly Gly Thr Ala
            180                 185                 190

Ala Leu Gly Cys Leu Val Lys Asp Tyr Phe Pro Glu Pro Val Thr Val
        195                 200                 205

Ser Trp Asn Ser Gly Ala Leu Thr Ser Gly Val His Thr Phe Pro Ala
        210                 215                 220

Val Leu Gln Ser Ser Gly Leu Tyr Ser Leu Ser Ser Val Val Thr Val
225                 230                 235                 240

Pro Ser Ser Ser Leu Gly Thr Gln Thr Tyr Ile Cys Asn Val Asn His
                245                 250                 255

Lys Pro Ser Asn Thr Lys Val Asp Lys Lys Val Glu Pro Lys Ser Cys
                260                 265                 270

Asp Lys Thr His Thr Cys Pro Pro Cys Pro Ala Pro Glu Leu Arg Gly
            275                 280                 285

Gly Pro Lys Val Phe Leu Phe Pro Pro Lys Pro Lys Asp Thr Leu Met
        290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Ala Ser Thr Tyr
                340                 345                 350

Arg Val Val Ser Val Leu Thr Val Leu His Gln Asp Trp Leu Asn Gly
            355                 360                 365

Lys Glu Tyr Lys Cys Lys Val Ser Asn Lys Ala Leu Pro Ala Pro Ile
        370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Lys Glu Met Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445
```

```
Tyr Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro

<210> SEQ ID NO 125
<211> LENGTH: 503
<212> TYPE: PRT
<213> ORGANISM: Artificial sequence
<220> FEATURE:
<223> OTHER INFORMATION: An artificially synthesized peptide sequence

<400> SEQUENCE: 125

Gln Asp Gly Asn Glu Glu Met Gly Gly Ile Thr Gln Thr Pro Tyr Lys
1               5                   10                  15

Val Ser Ile Ser Gly Gly Gly Ser Gly Gly Gly Ser Gly Gly
            20                  25                  30

Gly Gly Ser Leu Ser Gly Arg Ser Asp Asn His Gly Gly Ser Gln
                35                  40                  45

Val Gln Leu Val Glu Ser Gly Gly Leu Val Gln Pro Gly Arg Ser
    50                  55                  60

Leu Arg Leu Ser Cys Ala Ala Ser Gly Phe Thr Phe Ser Asn Ala Trp
65                  70                  75                  80

Met His Trp Val Arg Gln Ala Pro Gly Lys Gly Leu Glu Trp Val Ala
                85                  90                  95

Gln Ile Lys Asp Lys Ala Asn Gly Tyr Asn Ala Tyr Tyr Ala Glu Ser
                100                 105                 110

Val Lys Gly Arg Phe Thr Ile Ser Arg Asp Asp Ser Lys Asn Ser Ile
            115                 120                 125

Tyr Leu Gln Met Asn Ser Leu Lys Thr Glu Asp Thr Ala Val Tyr Tyr
    130                 135                 140

Cys Arg Tyr Val His Tyr Thr Thr Tyr Ala Gly Phe Ser Tyr Lys Phe
145                 150                 155                 160

Gly Val Asp Ala Trp Gly Gln Gly Thr Thr Val Thr Val Ser Ser Ala
                165                 170                 175

Ser Thr Lys Gly Pro Ser Val Phe Pro Leu Ala Pro Ser Ser Lys Ser
                180                 185                 190

Thr Ser Gly Gly Thr Ala Ala Leu Gly Cys Leu Val Lys Asp Tyr Phe
            195                 200                 205

Pro Glu Pro Val Thr Val Ser Trp Asn Ser Gly Ala Leu Thr Ser Gly
    210                 215                 220

Val His Thr Phe Pro Ala Val Leu Gln Ser Ser Gly Leu Tyr Ser Leu
225                 230                 235                 240

Ser Ser Val Val Thr Val Pro Ser Ser Ser Leu Gly Thr Gln Thr Tyr
                245                 250                 255

Ile Cys Asn Val Asn His Lys Pro Ser Asn Thr Lys Val Asp Lys Lys
                260                 265                 270

Val Glu Pro Lys Ser Cys Asp Lys Thr His Thr Cys Pro Pro Cys Pro
            275                 280                 285

Ala Pro Glu Leu Arg Gly Gly Pro Lys Val Phe Leu Phe Pro Pro Lys
    290                 295                 300

Pro Lys Asp Thr Leu Met Ile Ser Arg Thr Pro Glu Val Thr Cys Val
```

```
                305                 310                 315                 320
Val Val Asp Val Ser His Glu Asp Pro Glu Val Lys Phe Asn Trp Tyr
                    325                 330                 335
Val Asp Gly Val Glu Val His Asn Ala Lys Thr Lys Pro Arg Glu Glu
                    340                 345                 350
Gln Tyr Ala Ser Thr Tyr Arg Val Val Ser Val Leu Thr Val Leu His
                    355                 360                 365
Gln Asp Trp Leu Asn Gly Lys Glu Tyr Lys Cys Lys Val Ser Asn Lys
                    370                 375                 380
Ala Leu Pro Ala Pro Ile Glu Lys Thr Ile Ser Lys Ala Lys Gly Gln
385                 390                 395                 400
Pro Arg Glu Pro Gln Val Tyr Thr Leu Pro Pro Ser Arg Lys Glu Met
                    405                 410                 415
Thr Lys Asn Gln Val Ser Leu Thr Cys Leu Val Lys Gly Phe Tyr Pro
                    420                 425                 430
Ser Asp Ile Ala Val Glu Trp Glu Ser Asn Gly Gln Pro Glu Asn Asn
                    435                 440                 445
Tyr Lys Thr Thr Pro Pro Tyr Leu Asp Ser Asp Gly Ser Phe Phe Leu
                    450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                    485                 490                 495
Lys Ser Leu Ser Leu Ser Pro
                    500

<210> SEQ ID NO 126
<211> LENGTH: 236
<212> TYPE: PRT
<213> ORGANISM: Artificial sequence
<220> FEATURE:
<223> OTHER INFORMATION: An artificially synthesized peptide sequence

<400> SEQUENCE: 126

Gln Asp Gly Asn Glu Gly Gly Ser Gly Gly Gly Ser Gly Gly Gly
1               5                   10                  15

Ser Asp Val Val Met Thr Gln Thr Pro Val Ser Met Ser Val Ser Leu
                20                  25                  30

Gly Gly Gln Val Ser Ile Ser Cys Arg Ser Ser Gln Ser Leu Val His
                35                  40                  45

Asn Asn Gly Asn Thr Tyr Val Ser Trp Tyr Ile Gln Lys Pro Ser Gln
        50                  55                  60

Ser Pro Gln Leu Leu Ile Tyr Lys Val Ser Asn Arg Phe Ser Gly Ile
65                  70                  75                  80

Ser Asp Arg Phe Ser Gly Ser Gly Ser Gly Thr Asp Phe Thr Leu Lys
                85                  90                  95

Ile Ser Arg Val Glu Pro Asp Asp Leu Gly Val Tyr Tyr Cys Gly Gln
                100                 105                 110

Gly Thr Gln Asp Pro Tyr Thr Phe Gly Ala Gly Thr Lys Leu Glu Leu
                115                 120                 125

Lys Arg Thr Val Ala Ala Pro Ser Val Phe Ile Phe Pro Pro Ser Asp
                130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
```

```
                165                 170                 175
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 127
<211> LENGTH: 250
<212> TYPE: PRT
<213> ORGANISM: Artificial sequence
<220> FEATURE:
<223> OTHER INFORMATION: An artificially synthesized peptide sequence

<400> SEQUENCE: 127

Gln Asp Gly Asn Glu Glu Met Gly Gly Gly Ser Gly Gly Gly Ser Gly
1               5                   10                  15

Gly Gly Ser Leu Ser Gly Arg Ser Asp Asn His Gly Gly Gly Ser Asp
            20                  25                  30

Val Val Met Thr Gln Thr Pro Val Ser Met Ser Val Ser Leu Gly Gly
        35                  40                  45

Gln Val Ser Ile Ser Cys Arg Ser Ser Gln Ser Leu Val His Asn Asn
    50                  55                  60

Gly Asn Thr Tyr Val Ser Trp Tyr Ile Gln Lys Pro Ser Gln Ser Pro
65                  70                  75                  80

Gln Leu Leu Ile Tyr Lys Val Ser Asn Arg Phe Ser Gly Ile Ser Asp
                85                  90                  95

Arg Phe Ser Gly Ser Gly Ser Gly Thr Asp Phe Thr Leu Lys Ile Ser
            100                 105                 110

Arg Val Glu Pro Asp Asp Leu Gly Val Tyr Tyr Cys Gly Gln Gly Thr
        115                 120                 125

Gln Asp Pro Tyr Thr Phe Gly Ala Gly Thr Lys Leu Glu Leu Lys Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250

<210> SEQ ID NO 128
<211> LENGTH: 207
<212> TYPE: PRT
<213> ORGANISM: Homo sapiens

<400> SEQUENCE: 128
```

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Ile Thr
            20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
    50                  55                      60

Asn Ile Gly Gly Asp Glu Asp Asp Lys Asn Ile Gly Ser Asp Glu Asp
65                      70                  75                  80

His Leu Ser Leu Lys Glu Phe Ser Glu Leu Glu Gln Ser Gly Tyr Tyr
                    85                  90                  95

Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                     140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Ile
            195                 200                 205
```

<210> SEQ ID NO 129
<211> LENGTH: 198
<212> TYPE: PRT
<213> ORGANISM: Macaca fascicularis

<400> SEQUENCE: 129

```
Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
                35                  40                  45

Cys Ser Gln His Leu Gly Ser Glu Ala Gln Trp Gln His Asn Gly Lys
    50                  55                      60

Asn Lys Glu Asp Ser Gly Asp Arg Leu Phe Leu Pro Glu Phe Ser Glu
65                      70                  75                  80

Met Glu Gln Ser Gly Tyr Tyr Val Cys Tyr Pro Arg Gly Ser Asn Pro
                    85                  90                  95

Glu Asp Ala Ser His His Leu Tyr Leu Lys Ala Arg Val Cys Glu Asn
                100                 105                 110

Cys Met Glu Met Asp Val Met Ala Val Ala Thr Ile Val Ile Val Asp
            115                 120                 125

Ile Cys Ile Thr Leu Gly Leu Leu Leu Val Tyr Tyr Trp Ser Lys
130                 135                     140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Pro Val Pro Asn
```

```
                165                 170                 175
Pro Asp Tyr Glu Pro Ile Arg Lys Gly Gln Gln Asp Leu Tyr Ser Gly
            180                 185                 190

Leu Asn Gln Arg Arg Ile
        195
```

<210> SEQ ID NO 130
<211> LENGTH: 28
<212> TYPE: PRT
<213> ORGANISM: Artificial sequence
<220> FEATURE:
<223> OTHER INFORMATION: An artificially synthesized peptide sequence

<400> SEQUENCE: 130

```
Ser Gly Gly Gly Gly Ser Gly Gly Gly Ser Gly Gly Gly Gly Ser
1               5                   10                  15

Leu Ser Gly Arg Ser Asp Asn His Gly Gly Gly Ser
            20                  25
```

<210> SEQ ID NO 131
<211> LENGTH: 8
<212> TYPE: PRT
<213> ORGANISM: Artificial sequence
<220> FEATURE:
<223> OTHER INFORMATION: An artificially synthesized peptide sequence
<220> FEATURE:
<221> NAME/KEY: Xaa
<222> LOCATION: (1)..(1)
<223> OTHER INFORMATION: is LEU, TYR, TRP, PHE, MET, ALA, GLN, ASN, GLU,
      LYS
<220> FEATURE:
<221> NAME/KEY: Xaa
<222> LOCATION: (2)..(2)
<223> OTHER INFORMATION: is SER, TRP, PHE, ALA, PRO, GLN, GLU, ASP
<220> FEATURE:
<221> NAME/KEY: XAA
<222> LOCATION: (3)..(3)
<223> OTHER INFORMATION: is GLY, TYR, TRP, PHE, ILE, LEU, MET, PRO, THR,
      GLN, ASN, HIS, CIS
<220> FEATURE:
<221> NAME/KEY: Xaa
<222> LOCATION: (4)..(4)
<223> OTHER INFORMATION: is ARG, TYR, TRP, PHE, ILE, MET, PRO, GLN, ASN,
      GLU, ASP, LYS
<220> FEATURE:
<221> NAME/KEY: Xaa
<222> LOCATION: (5)..(5)
<223> OTHER INFORMATION: is SER, TRP, ILE, LEU, MET, ALA, GLY, GLN, ASN.
      GLU, ASP, LYS, ARG, HIS
<220> FEATURE:
<221> NAME/KEY: Xaa
<222> LOCATION: (6)..(6)
<223> OTHER INFORMATION: is ASP, TRP, PHE, MET, PRO, SER, GLN, LYS, ARG,
      CIS
<220> FEATURE:
<221> NAME/KEY: Xaa
<222> LOCATION: (7)..(7)
<223> OTHER INFORMATION: is ASN, TYR, TRP, PHE, LEU, VAL, MET, ALA, GLY,
      PRO, CIS
<220> FEATURE:
<221> NAME/KEY: Xaa
<222> LOCATION: (8)..(8)
<223> OTHER INFORMATION: is HIS, TRP, PHE, ILE, ALA, GLY, PRO, THR, GLN,
      GLU, ASP, LYS, CIS

<400> SEQUENCE: 131

```
Xaa Xaa Xaa Xaa Xaa Xaa Xaa Xaa
1               5
```